US007053117B2

(12) United States Patent
Cai

(10) Patent No.: US 7,053,117 B2
(45) Date of Patent: May 30, 2006

(54) SUBSTITUTED 4H-CHROMENES AND ANALOGS AS ACTIVATORS OF CASPASES AND INDUCERS OF APOPTOSIS AND THE USE THEREOF

(75) Inventor: Sui Xiong Cai, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 158 days.

(21) Appl. No.: 10/146,138

(22) Filed: May 16, 2002

(65) Prior Publication Data

US 2003/0065018 A1 Apr. 3, 2003

Related U.S. Application Data

(60) Provisional application No. 60/290,997, filed on May 16, 2001.

(51) Int. Cl.
C07D 311/58 (2006.01)
A61K 31/35 (2006.01)

(52) U.S. Cl. .................................. 514/456; 549/404
(58) Field of Classification Search ................ 544/151, 544/309, 310, 376; 546/282.7; 548/525; 549/404; 514/233.5, 274, 254.11, 337, 422, 514/456
See application file for complete search history.

(56) References Cited

U.S. PATENT DOCUMENTS

| 4,698,345 | A | 10/1987 | Dicker et al. | |
|---|---|---|---|---|
| 5,281,619 | A | 1/1994 | Dell et al. | 514/454 |
| 5,284,868 | A | 2/1994 | Dell et al. | |
| 5,434,160 | A | 7/1995 | Dell et al. | |
| 5,514,706 | A | 5/1996 | Ambler et al. | |
| 5,571,818 | A | 11/1996 | Williams | |
| 5,574,034 | A | 11/1996 | Williams | |
| 5,576,325 | A | 11/1996 | Williams | |
| 5,624,953 | A | 4/1997 | Ambler et al. | |
| 5,637,589 | A | 6/1997 | Lee et al. | |
| 5,726,204 | A | 3/1998 | Lee et al. | |
| 5,847,165 | A | 12/1998 | Lee et al. | |
| 6,160,010 | A | 12/2000 | Uckun et al. | 514/521 |
| 6,221,900 | B1 | 4/2001 | Uckun et al. | 514/457 |
| 6,258,824 | B1 | 7/2001 | Yang | 514/312 |
| 6,294,575 | B1 | 9/2001 | Uckun et al. | 514/521 |
| 6,303,652 | B1 | 10/2001 | Uckun et al. | 514/521 |
| 6,365,626 | B1 | 4/2002 | Uckun et al. | 514/521 |
| 6,388,092 | B1 | 5/2002 | Yang | 548/333.5 |
| 2002/0076733 | A1* | 6/2002 | Kasibhatla et al. | 435/7.21 |

FOREIGN PATENT DOCUMENTS

| EP | 0 537 949 A1 | 4/1993 |
|---|---|---|
| EP | 0 599 514 A2 | 6/1994 |
| EP | 0 618 206 A1 | 10/1994 |
| EP | 0 619 314 A1 | 10/1994 |
| WO | WO 96/20721 A1 | 7/1996 |
| WO | WO 98/24427 A2 | 6/1998 |
| WO | WO 99/54286 | 10/1999 |
| WO | WO 99/54286 A2 | 10/1999 |
| WO | WO 00/04901 | 2/2000 |
| WO | WO 01/34591 A2 | 5/2001 |
| WO | WO 03/096982 A2 | 11/2003 |
| WO | WO 03/097806 A2 | 11/2003 |

OTHER PUBLICATIONS

Al-Mousawi et al., CAPLUS Abstract 131: 199593, 1999.*
Klokol et al., CAPLUS Abstract 108:5822, 1988.*
Simone, Oncology: Introduction, Cecil Textbook of Medicine, 20th Edition, vol. 1, pp. 1004-1010, 1996.*
Wachlin et al., IL-1beta, IFN-gamma and TNF-alpha increase vulnerability of pancreatic beta cells to autoimmune destruction, Journal of Autoimmunity, 20, pp. 303-312, 2003.*
Elgert, Immunology—Understanding the Immune System, pp. 315-331, 1996.*
Robinson, Medical Therapy of Inflammatory Bowel Disease for the 21st Century, Eur. J. Surg. Suppl. 582: 90-98, 1998.*
Shevach, Animal Models for Autoimmune and Inflammatory Disease, Current Protocols in Immunology, Suppl. 52, 15.0.1-15.0.6, 2002.*
Singh et al., Immune Therapy in Inflammatory bowel disease and models of colitis, British Journal of Surgery, 88, pp. 1558-1569, 2001.*
Bremner et al., Therapy of Crohn's Disease in childhood, Expert Opin. Pharmacother. 3(7):809-825, 2002.*

(Continued)

Primary Examiner—Deepak Rao
(74) Attorney, Agent, or Firm—Sterne, Kessler, Goldstein & Fox P.L.L.C.

(57) ABSTRACT

The present invention is directed to substituted 4H-chromenes and analogs thereof, represented by the general Formula I:

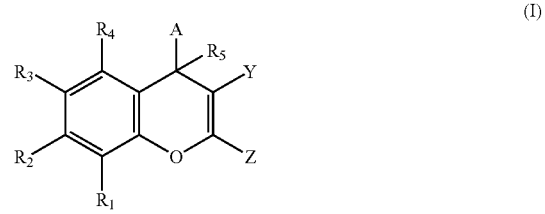

(I)

wherein $R_1$–$R_5$, A, Y and Z are defined herein. The present invention also relates to the discovery that compounds having Formula I are activators of caspases and inducers of apoptosis. Therefore, the activators of caspases and inducers of apoptosis of this invention can be used to induce cell death in a variety of clinical conditions in which uncontrolled growth and spread of abnormal cells occurs.

11 Claims, No Drawings

OTHER PUBLICATIONS

Thornberry, N. A., et al., "A Combinatorial Approach Defines Specificities of Members of the Caspase Family and Granzyme B. Functional Relationships Established for Key Mediators of Apoptosis," *J. Biol. Chem.* 272:17907-17911, The American Society for Biochemistry and Molecular Biology, Inc. (1997).

Batteux, F., et al., "Gene Therapy of Experimental Autoimmune Thyroiditis by In Vivo Administration of Plasmid DNA Coding for Fas Ligand," *J. Immunol.* 162:603-608, The American Association of Immunologists (1999).

Birch, K.A., et al., "LY290181, an Inhibitor oF Diabetes-Induced Vascular Dysfunction, Blocks Protein Kinase C-Stimulated Transcriptional Activation Through Inhibition of Transcription Factor Binding to a Phorbol Response Element," *Diabetes* 45 :642-650, American Diabetes Association (1996).

Boirivant, M., et al., "Lamina Propria T Cells in Crohn's Disease and Other Gastrointestinal Inflammation Show Defective CD2 Pathway-Induced Apoptosis," *Gastroenterology 116*: 557-565, The American Gastroenterological Association (1999).

Coven, T. R., et al., "PUVA-induced lymphocyte apoptosis: Mechanism of action in psoriasis," *Photodermatol. Photoimmunol. Photomed.* 15:22-27, Munksgaard (1999).

Ellis, R.E., et al., "Mechanisms and Functions of Cell Death," *Ann. Rev. Cell Biol.* 7:663-698, Annual Reviews, Inc. (1991).

Friesen, C., et al., "Involvement of the CD95 (APO-1/Fas) receptor/ligand system in drug-induced apoptosis in leukemia cells," *Nat. Med.* 2:574-577, Nature Publishing Co. (1996).

Greenwald, R.B., et al., "Drug Delivery Systems Employing 1, 4- or 1,6- Elimination: Poly (ethylene glycol) Prodrugs of Amine-Containing Compounds," *J. Med. Chem.* 42 :3657-3667, American Chemical Society (1999).

Heenen, M., et al., "Methotrexate induces apoptotic cell death in human keratinocytes," *Arch. Dermatol. Res.* 290 : 240-245, Springer-Verlag (1998).

Infante, A.J., et al., "The clinical spectrum in a large kindred with autoimmune lymphoproliferative syndrome caused by a Fas mutation that impairs lymphocyte apoptosis," *J. Pediatr.* 133 : 629-633, Mosby, Inc. (1998).

Leu, Y. -L., et al., "Design and Synthesis of Water-Soluble Glucuronide Derivatives of Camptothecin for Cancer Prodrug Monotherapy and Antibody-Directed Enzyme Prodrug Therapy (ADEPT) ," *J. Med. Chem.* 42:3623-3628, American Chemical Society (1999).

López-Hoyos, M., et al., "Regulation of B cell apoptosis by Bcl-2 and Bcl-$X_L$ and its role in the development of autoimmune diseases (Review) ," *Int. J. Mol. Med.* 1: 475-483, D.A. Spandidos (1998).

Los, M., et al., "Cross-Resistance of CD95- and Drug-Induced Apoptosis as a Consequence of Deficient Activation of Caspases (ICE/Ced-3 Proteases) ," *Blood 90*:3118-3129, W.B. Saunders Co. (1997).

O'Reilly, L.A., and Strasser, A., "Apoptosis and autoimmune disease," *Inflamm. Res.* 48: 5-21, Birkhäuser Verlag (1999).

Ohsako, S., and Elkon, K.B., "Apoptosis in the effector phase of autoimmune diabetes, multiple sclerosis and thyroiditis," *Cell Death Differ.* 6:13-21, Stockton Press (1999).

Orrenius, S., "Apoptosis: molecular mechanisms and implications for human disease," *J. Internal Med.* 237:529-536, Blackwell Science Ltd. (1995).

Ozawa, M., et al., "312-nanometer Ultraviolet B Light (Narrow-Band UVB) Induces Apoptosis of T Cells within Psoriatic Lesions," *J. Exp. Med.* 189:711-718, The Rockefeller University Press (1999).

Panda, D., et al., "Suppression of Microtubule Dynamics by LY290181: A Potential Mechanism for Its Antiproliferative Action," *J. Biol. Chem.* 272: 7681-7687, The American Society for Biochemistry and Molecular Biology, Inc. (1997).

Savill, J., "Apoptosis in resolution of inflammation," *J. Leukoc. Biol.* 61 : 375-380, The Society for Leukocyte Biology (1997).

Schmitt, E., et al., "The Bcl-xL and BAX-α control points: modulation of apoptosis induced by cancer chemotherapy and relation to TPCK-sensitive protease and caspase activation," *Biochem. Cell Biol.* 75:301-314, National Research Council of Canada (1997).

Smith, C.W., "The Anti-rheumatic Potential of a Series of 2, 4-Di-substituted-4H-naphtho [1,2-b] pyran-3-carbonitriles," *Bioorg. Med. Chem. Lett.* 5:2783-2788, Elsevier Science Ltd. (1995).

Thornberry, N.A., "The caspase family of cysteine proteases," *Brit. Med. Bull.* 53:478-490, Oxford University Press (1997).

Thornberry, N.A., "Caspases: key mediators of apoptosis," *Chem. Biol.* 5:R97-R103, Current Biology Ltd. (1998).

Vaishnaw, A.K., et al., "The molecular basis for apoptotic defects in patients with CD95 (Fas/Apo-1) mutations," *J. Clin. Invest.* 103:355-363, The American Society for Clinical Investigation (1999).

Wakisaka, S., et al., "Modulation by proinflammatory cytokines of Fas/Fas ligand-mediated apoptotic cell death of synovial cells in patients with rheumatoid arthritis (RA) ," *Clin. Exp. Immunol.* 114 : 119-128, Blackwell Science (1998).

Wood, D.L., "Inhibition of Mitosis and Microtubule Function through Direct Tubulin Binding by a Novel Antiproliferative Naphthopyran LY290181," *Mol. Pharmacol.* 52:437-444, The American Society for Pharmacology and Experimental Therapeutics (1997).

Wyllie, A.H., et al., "Cell Death: The Significance of Apoptosis," *Int. Rev. Cyt.* 68:251-306, Academic Press, Inc. (1980).

Wyllie, A.H., "Cell death: a new classification separating apoptosis from necrosis," in *Cell death in biology and pathology*, Bowen and Lockshin, eds., Chapman and Hall, London, England, pp. 9-34 (1981).

Zhou, T., et al., "Bisindolylmalcimide VIII facilitates Fas-mediated apoptosis and inhibits T cell-mediated autoimmune diseases," *Nat. Med.* 5:42-48, Nature Publishing Co. (1999).

Pending U.S. Appl. No. 09/705,840, Cai et al., filed Nov. 6, 2000 (Not Published).

Pending U.S. Appl. No. 10/146,136, Cai et al., filed May 16, 2002 (Not Published).

Pending U.S. Appl. No. 10/146,139, Cai et al., filed May 16, 2002 (Not Published).

Al-Mousawi, S.M. et al., "Synthesis of New Condensed 2-Amino-4H-pyran-3-carbonitriles and of 2-Aminoquinoline-3-carbonitriles," *Organic Preparations and Procedures Int.* 31:305-313, Organic Preparations and Procedures Inc. (1999).

Bloxham, J. et al., "Preparation of Some New Benzylidenemalono-nitriles by an $S_NAr$ Reaction: Application to Naphtho[1,2-b]pyran Synthesis," *Heterocycles* 38:399-408, The Japanese Institute of Heterocyclic Chemistry (1994).

Chandrasekhar, S. et al., "Identification of a Novel Chemical Series That Blocks Interleukin-1-Stimulated Metalloprotease Activity in Chondrocytes," *J. Pharmacol. Exper. Ther.* 273:1519-1528, The American Society for Pharmacology and Experimental Therapeutics (1995).

Elagamey, A.G.A. et al., "Nitriles In Heterocyclic Synthesis: Novel Syntheses of Benzo[b]pyrans, Naphtho[1,2-b]pyrans, Naphtho[2,1-b]pyrans, Pyrano[3,2-h]quinolines and Pyrano[3,2-c]quinolines," *Collection Czechoslovak Chem. Commun.* 53:1534-1538, Czechoslovak Academy of Sciences (1988).

Elagamey, A.G.A. and El-Taweel, F.M.A.A., "Nitriles in heterocyclic synthesis: Synthesis of condensed pyrans," *Indian J. Chem.* 29B:885-886, The Council of Scientific & Industrial Research, New Delhi (1990).

Gourdeau, H. et al., "Antivascular and antitumor evaluation of 2-amino-4-(3-bromo-4,5-dimethoxy-phenyl)-3-cyano-4H-chromenes, a novel series of anticancer agents," *Mol. Cancer Ther.* 3:1375-1383, American Association for Cancer Research (2004).

Kasibhatla, S. et al., "Discovery and mechanism of action of a novel series of apoptosis inducers with potential vascular targeting activity," *Mol. Cancer Ther.* 3:1365-1373, American Association for Cancer Research (2004).

Kemnitzer, W. et al., "Discovery of 4-Aryl-4H-chromenes as a New Series of Apoptosis Inducers Using a Cell- and Caspase-based High-Throughput Screening Assay. 1. Structure-Activity Relationships of the 4-Aryl Group," *J. Med. Chem.* 47:6299-6310, American Chemical Society (2004).

Klokol, G.V. et al., "Cyclization of Nitriles. XXIII. Addition of Active Phenols to Electron-Deficient Ethylenes, Accompanied by Cyclization to 2-Amino-4H-benzo[b]pyrans. Crystal Structure of 2-Amino-4-(2-fluorophenyl)-3-ethoxycarbonyl-4H-naphtho[2,1-b]pyran," *J. Organic Chem. of USSR* 23:369-377, Plenum Publishing Corporation (1987).

Klokol, G.V. et al., "Cyclization of nitriles. XXIII. Addition of active phenols to electron-deficient ethylenes with cyclization to 2-amino-4H-benzo[b]pyrans. Crystal structure of 2-amino-4-(2-fluorophenyl)-3-(ethoxycarbonyl)4H-naphtho[2,1-b]pyran," *Chem. Abstr.* 108:5822c, Chemical Abstracts Service (1988).

Radwan, S.M. et al., "Synthesis and Some Reactions of New Benzo[b]pyran Derivatives," *Phosphorus, Sulfur, and Silicon* 101:207-211, Overseas Publishers Associate (1995).

Ram, Vishnu J. and Verma, M., "Synthesis of 4H-benzopyrans, benzopyrano [2-3-d]pyrimidines and related compounds as biodynamic agents," *Indian J. Chem.* 33B:908-911, The Council of Scientific & Industrial Research, New Delhi (1994).

Sharanin, Y.A. and Klokol, G.V., "Synthesis of 2-amino-4H-chromenes," *Chem. Abstr.* 99:212393z, Chemical Abstracts Service (1983).

Sharanin, Y.A. and Klokol, G.V., "Synthesis of 2-Amino-4H-chromenes," *J. Organic Chem. of USSR* 19:1582-1583, Plenum Publishing Corporation (1984).

Wiernicki, T.R. et al., "Inhibition of Vascular Smooth Muscle Cell Proliferation and Arterial Intimal Thickening by a Novel Antiproliferative Naphthopyran," *J. Pharmacol. Exper. Ther.* 278:1452-1459, The American Society for Pharmacology and Experimental Therapeutics (1996).

* cited by examiner

ACTIVATORS OF CASPASES
AND INDUCERS OF APOPTOSIS AND THE
USE THEREOF

CROSS-REFERENCE TO RELATED APPLICATIONS

This application claims priority benefit under 35 U.S.C. § 119(e) of U.S. Provisional Application No. 60/290,997, filed May 16, 2001, the contents of which are entirely incorporated by reference herein.

BACKGROUND OF THE INVENTION

1. Field of the Invention

This invention is in the field of medicinal chemistry. In particular, the invention relates to substituted 4H-chromenes and analogs, and the discovery that these compounds are activators of caspases and inducers of apoptosis.

The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development, as well as in tissue homeostasis and aging (Glucksmann, A., Biol. Rev. Cambridge Philos. Soc. 26:59–86 (1951); Glucksmann, A., Archives de Biologie 76:419–437 (1965); Ellis, et al., Dev. 112:591–603 (1991); Vaux, et al., Cell 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., J. Internal Medicine 237:529–536 (1995)).

Apoptosis is achieved through an endogenous mechanism of cellular suicide (Wyllie, A. H., in Cell Death in Biology and Pathology, Bowen and Lockshin, eds., Chapman and Hall (1981), pp. 9–34). A cell activates its internally encoded suicide program as a result of either internal or external signals. The suicide program is executed through the activation of a carefully regulated genetic program (Wyllie, et al., Int. Rev. Cyt. 68.251 (1980); Ellis, et al., Ann. Rev. Cell Bio. 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., J. Internal Medicine 237:529–536 (1995)).

It has been found that a group of proteases are a key element in apoptosis (see, e.g., Thornberry, Chemistry and Biology 5:R97–R103 (1998); Thornberry, British Med. Bull. 53:478–490 (1996)). Genetic studies in the nematode Caenorhabditis elegans revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (Apoptosis and Cancer Chemotherapy, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal and cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., Biochem. Cell. Biol. 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., Blood 90:3118–3129 (1997); Friesen, et al., Nat. Med. 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis, occurs in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g., colon cancers, exist primarily in the $G_o$ phase, whereas rapidly proliferating normal tissues, e.g., bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., Goodman and Gilman's The Pharmacological Basis of Therapeutics, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP537949 discloses derivatives of 4H-naphthol[1,2-b] pyran as antiproliferatives:

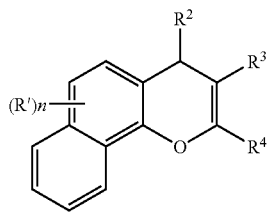

wherein,
each $R^1$ is independently halo, trifluoromethyl, $C_{1-4}$ alkoxy, hydroxy, nitro, $C_{1-4}$ alkyl, $C_{1-4}$ alkylthio, hydroxy-$C_{1-4}$alkyl, hydroxy-$C_{1-4}$ alkoxy, trifluoromethoxy, carboxy, —COOR$^5$ where $R^5$ is an ester group, —CONR$^6$R$^7$ or —NR$^6$R$^7$ where $R^6$ and $R^7$ are each hydrogen or $C_{1-4}$ alkyl;
$R^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or $R^2$ is furanyl optionally substituted with $C_{1-4}$ alkyl;
$R^3$ is nitrile, carboxy, —COOR$^8$ where $R^8$ is an ester group, —CONR$^9$R$^{10}$ where $R^9$ and $R^{10}$ are each hydrogen or $C_{1-4}$ alkyl or $R^{11}SO_2$ where $R^{11}$ is $C_{1-4}$ alkyl or optionally substituted phenyl;
$R^4$ is —NR$^{12}$R$^{13}$, —NHCOR$^2$, —N(COR$^{12}$)$_2$ or —N=CHOCH$_2$R$^{12}$ where $R^{12}$ and $R^{13}$ are each hydrogen or $C_{1-4}$ alkyl optionally substituted with carboxy, or $R^4$ is

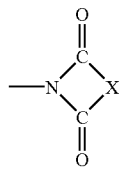

where X is $C_{2-4}$ alkylene, or $R^4$ is —NHSO$_2$R$^{14}$ where $R^{14}$ is $C_{1-4}$ alkyl or optionally substituted phenyl; and
n is 0–2.

U.S. Pat. No. 5,281,619 discloses naphthopyrans for therapy of diabetic complications:

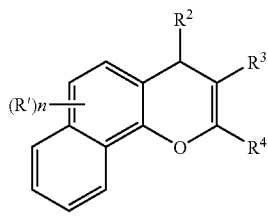

wherein,
$R^1$ is $C_{1-4}$ alkoxy, OH or COOH;
$R^2$ is optionally substituted phenyl;
$R^3$ is nitrile, or $R^3$ is carboxy or —COOR$^8$ when $R^2$ is phenyl substituted with 3-nitro or 3-trifluoromethyl and $R^8$ is an ester group;
$R^4$ is NR$^{12}$R$^{13}$, —NHCOR$^2$, —N(COR$^2$)$_2$ or —N=CHOCH$_2$R$^{12}$, wherein $R^{12}$ and $R^{13}$ are each H or $C_{1-4}$ alkyl; and
n is 0–2.

EP599514 discloses the preparation of pyranoquinoline derivatives as inhibitors of cell proliferation:

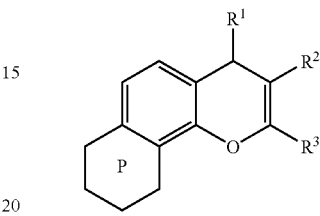

wherein $R^1$ is optionally substituted phenyl or optionally substituted heteroaryl selected from thienyl, pyridyl, benzothienyl, quinolinyl, benzofuranyl or benzimidazolyl, or $R^1$ is furanyl optionally substituted with $C_{1-4}$ alkyl;
$R^2$ is nitrile, carboxy, —CO$_2$R$^4$ wherein $R^4$ is an ester group, —CON(R$^5$)R$^6$ where $R^5$ and $R^6$ are independently H or $C_{1-4}$ alkyl, or $R^7SO_2$ where $R^7$ is $C_{1-4}$ alkyl or optionally substituted phenyl;
$R^3$ is —NR$^8$R$^9$, —NHCOR$^8$, —N(CO$_2$R$^8$)$_2$, —N=CHOR$^8$ where $R^8$ and $R^9$ are independently H or $C_{1-4}$ alkyl, or —NHSO$^2$R$^{10}$ where $R^{10}$ is $C_{1-4}$ alkyl or optionally substituted phenyl, or

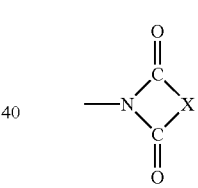

where X is $C_{2-4}$ alkylene; and
the ring P represents a pyridine fused to the benzopyran nucleus.

EP618206 discloses the preparation of naphthopyran and pyranoquinoline as immunosuppressants and cell proliferation inhibitors:

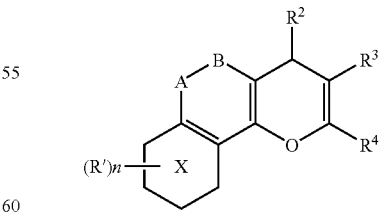

wherein,
A-B is CH$_2$CH$_2$ or CH=CH;
each $R^1$ is independently halo, carboxy, trifluoromethyl, hydroxy, $C_{1-4}$ alkyl, $C_{1-4}$ alkoxy, $C_{1-4}$ alkylthio, hydroxy-$C_{1-4}$alkyl, hydroxy-$C_{1-4}$alkoxy, nitrogen-containing heterocyclyl, nitro, trifluoromethoxy, —COOR$^5$ where R$^5$ is an ester group, —COR$^6$, —CONR$^6$R$^7$ or —NR$^6$R$^7$ where R$^6$ and R$^7$ are each hydrogen or C$_{1-4}$ alkyl;

R$^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or R$^2$ is furanyl optionally substituted with C$_{1-4}$ alkyl;

R$^3$ is nitrile, carboxy, —COOR$^8$ where R$^8$ is an ester group, —CONR$^9$R$^{10}$ where R$^9$ and R$^{10}$ are each hydrogen or C$_{1-4}$ alkyl, or —SO$_2$R$^{11}$ where R$^{11}$ is C$_{1-4}$ alkyl or optionally substituted phenyl-C$_{1-4}$ alkyl;

R$^4$ is 1-pyrrolyl, 1-imidazolyl or 1-pyrazolyl, each of which is optionally substituted by one or two C$_{1-4}$ alkyl, carboxyl, hydroxyl-C$_{1-4}$ alkyl or —CHO groups, or R$^4$ is 1-(1,2,4-triazolyl), 1-(1,3,4-triazolyl) or 2-(1,2,3-triazolyl), each of which is optionally substituted by a C$_{1-4}$ alkyl or C$_{1-4}$ perfluoroalkyl group, or R$^4$ is 1-tetrazolyl optionally substituted by C$_{1-4}$ alkyl;

X is a pyridine or a benzene ring; and
n is 0–2.

EP619314 discloses the preparation of 4-phenyl-4H-naphtho(2,1-b)pyran derivatives:

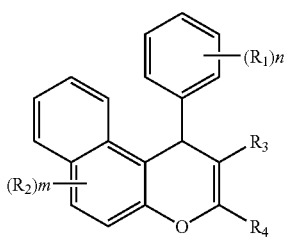

wherein,

R$^1$ and R$_2$ are independently halo, trifluoromethyl, C$_1$–C$_4$ alkoxy, hydroxy, nitro, C$_1$–C$_4$ alkyl, C$_1$–C$_4$ alkylthio, hydroxy-C$_1$–C$_4$ alkyl, hydroxy-C$_1$–C$_4$alkoxy, trifluoromethoxy, carboxy, —COOR$_8$ where R$_8$ is an ester group, —COR$_9$, —CONR$_9$R$_{10}$ or —NR$_9$R$_{10}$ where R$_9$ and R$_{10}$ are each hydrogen or C$_1$–C$_4$ alkyl;

R$_3$ is nitrile, carboxy or —CO$_2$R$_{11}$ wherein R$_{11}$ is an ester group;

R$_4$ is —NR$_{12}$R$_{13}$, —NR$_{12}$COR$_{13}$, —N(COR$_{12}$)$_2$ or —N=CHOCH$_2$R$_{12}$ where R$_{12}$ and R$_{13}$ are each hydrogen or C$_{1-4}$ alkyl, or R$_4$ is

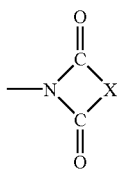

where X is C$_2$–C$_4$ alkylene, or R$_4$ is optionally substituted 1-pyrrolyl; and
m and n are each independently 0–2.

The compounds are said to be useful for the treatment of restenosis, immune disease, and diabetic complications.

Smith, et al., (*Bioorg. Med. Chem. Lett.* 5:2783–2788 (1995)) reported the anti-rheumatic potential of a series of 2,4-di-substituted-4H-naphtho[1,2-b]pyran-3-carbonitriles. They reported that 4-(3-nitrophenyl)-2-(N-succinimido)-4H-naphtho[1,2-b]pyran-3-carbonitrile has proved to be acid stable and still retains biological activity:

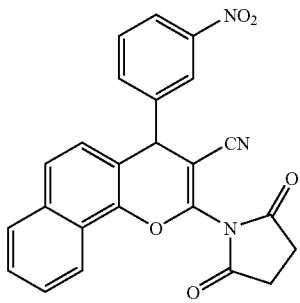

Birch, et al., (*Diabetes* 45:642–650 (1996)) reported that LY290181, an inhibitor of diabetes-induced vascular dysfunction, blocks protein kinase C-stimulated transcriptional activation through inhibition of transcription factor binding to a phorbol response element:

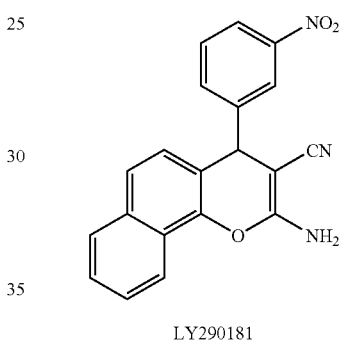

LY290181

Panda, et al., (*J. Biol. Chem.* 272: 7681–7687 (1997)) reported the suppression of microtubule dynamics by LY290181, which might be the potential mechanism for its antiproliferative action.

Wood, et al., (*Mol. Pharmacol.* 52: 437–444 (1997)) reported that LY290181 inhibited mitosis and microtubule function through direct tubulin binding.

PCT published patent application WO9824427 disclosed antimicrotubule compositions and methods for treating or preventing inflammatory diseases. LY290181 was listed as an antimicrotubule agent.

SUMMARY OF THE INVENTION

The present invention is related to the discovery that substituted 4H-chromene and analogs, as represented in Formula I, are activators of the caspase cascade and inducers of apoptosis. Thus, an aspect of the present invention is directed to the use of compounds of Formula I as inducers of apoptosis.

A second aspect of the present invention is to provide a method for treating, preventing or ameliorating neoplasia and cancer by administering a compound of Formula I to a mammal in need of such treatment.

Many of compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

DETAILED DESCRIPTION OF THE INVENTION

The present invention arises out of the discovery that substituted 4H-chromene and analogs, as represented in Formula I, are potent and highly efficacious activators of the caspase cascade and inducers of apoptosis. Therefore, compounds of Formula I are useful for treating disorders responsive to induction of apoptosis.

Specifically, compounds useful in this aspect of the present invention are represented by Formula I:

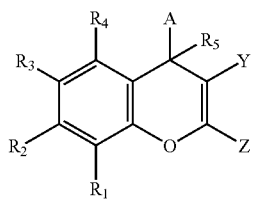

(I)

or pharmaceutically acceptable salts or prodrugs thereof, wherein:

$R_1-R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached form an aryl, heteroaryl, partially saturated carbocyclic or partially saturated heterocyclic group, wherein said group is optionally substituted;

$R_5$ is hydrogen or $C_{1-10}$ alkyl;

A is optionally substituted and is aryl, heteroaryl, saturated carbocyclic, partially saturated carbocylic, saturated heterocyclic, partially saturated heterocyclic or arylalkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle; and Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle.

Preferably $R_1$ and $R_2$ are taken together with the atoms to which they are attached form an aryl, heteroaryl, partially saturated carbocyclic or partially saturated heterocyclic group, wherein said group is optionally substituted.

Preferred are compounds of Formula I, wherein $R_1$ and $R_2$ are taken together form a structure selected from the group consisting of —OCH$_2$O—, —(CH$_2$)$_3$—, —(CH$_2$)$_4$—, —OCH$_2$CH$_2$O—, —CH$_2$N(V)CH$_2$—, —CH$_2$CH$_2$N(V)CH$_2$—, —CH$_2$N(V)CH$_2$CH$_2$—, —N(V)—CH=CH—, —CH=CH—N(V)—, —O—CH=CH—, —CH=CH—O—, —S—CH=CH—, —CH=CH—S— and —N=CH—CH=N—, wherein V is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferred compounds falling within the scope of Formula I include compounds wherein $R_3$ and $R_4$ are each hydrogen; more preferably $R_3$, $R_4$ and $R_5$ are each hydrogen. Preferred compounds of Formula I include compounds wherein A is phenyl, naphthyl, pyridyl, quinolyl, isoquinolyl, thienyl, furyl, pyrrolyl, indolyl, 2-phenylethyl, dihydrophenyl, tetrahydrophenyl or cyclohexyl, any of which is optionally substituted. More preferably, A is optionally substituted phenyl or optionally substituted pyridyl. Preferably, $R_5$ is hydrogen. Preferably, Z is NH$_2$. Preferably, Y is CN.

Another preferred embodiment is represented by Formula II:

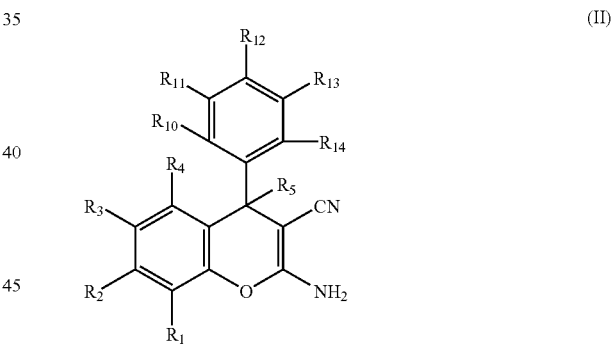

(II)

or pharmaceutically acceptable salts or prodrugs thereof, wherein $R_1$–$R_5$ are as defined previously with respect to Formula I; and $R_{10}$–$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached form an aryl, heteroaryl, partially saturated carbocyclic or partially saturated heterocyclic group, wherein said group is optionally substituted.

Preferred are compounds of Formula II, wherein $R_{10}$ and $R_{11}$, or $R_{11}$ and $R_{12}$, taken together form a structure selected from the group consisting of —OCH$_2$O—, —(CH$_2$)$_3$—, —(CH$_2$)$_4$—, —OCH$_2$CH$_2$O—, —CH$_2$N(V)CH$_2$—, —CH₂CH₂N(V)CH₂—, —CH₂N(V)CH₂CH₂—, —CH=CH—CH=CH—, —N(V)—CH=CH—, —CH=CH—N(V)—, —O—CH=CH—, —CH=CH—O—, —S—CH=CH—, —CH=CH—S—, —N=CH—CH=CH—, —CH=N—CH=CH—, —CH=CH—N=CH—, —CH=CH—CH=N— and —N=CH—CH=N—, wherein V is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferred compounds falling within the scope of Formula II include compounds wherein $R_1$–$R_2$ are independently hydrogen, halogen, hydroxy, $C_{1-10}$ alkyl, hydroxyalkyl, aminoalkyl, carboxyalkyl, amino, acylamido, acyloxy, alkoxy, methylenedioxy or alkylthiol. Preferably $R_5$ is hydrogen.

Another preferred embodiment is represented by Formula III:

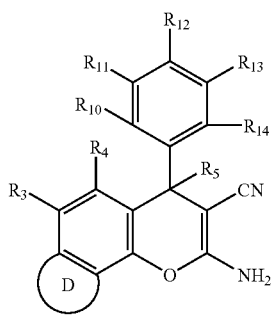

(III)

or pharmaceutically acceptable salts or prodrugs thereof, wherein;

$R_3$–$R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

$R_{10}$–$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached form an aryl, heteroaryl, partially saturated carbocyclic or partially saturated heterocyclic group, wherein the group is optionally substituted; and D is an optionally substituted aromatic or heteroaromatic ring.

Preferred compounds falling within the scope of Formula III include compounds wherein $R_3$–$R_4$ are hydrogen. Preferably $R_5$ is hydrogen. Another group of preferred compounds are those wherein $R_{10}$ and $R_{14}$ are hydrogen. Preferably D is an optionally substituted aromatic or heteroaromatic ring selected from the group consisting of benzo, pyrido, furo, thieno, pyrrolo, imidazo and pyrazo.

Exemplary preferred compounds that may be employed in the method of the invention include, without limitation:

2-Amino-3-cyano-7-hydroxy-4-(3-bromo-4,5-dimethoxyphenyl)-4H-chromene;
2-Amino-3-cyano-7-ethylamino-4-(3-bromo-4,5-dimethoxyphenyl)-4H-chromene;
2-Amino-3-cyano-7-hydroxy-4-(3-cyanophenyl)-4H-chromene;
2-Amino-3-cyano-7,8-dihydroxy-4-(3-bromo-4,5-dimethoxyphenyl)-4H-chromene;
2-Amino-3-cyano-7-amino-4-(3,5-dichlorophenyl)-4H-chromene;
2-Amino-3-cyano-7-methoxy-4-(3,5-dichlorophenyl)-4H-chromene;
2-Amino-3-cyano-4-(3,5-dichlorophenyl)-4H-indolo[4,5-b]pyran;
2-Amino-3-cyano-4-(3-chlorophenyl)-4H-indolo[4,5-b]pyran;
2-Amino-3-cyano-7-amino-8-methyl-4-(3-bromo-4,5-dimethoxyphenyl)-4H-chromene;
2-Amino-3-cyano-7-hydroxy-8-amino-4-(3-bromo-4,5-dimethoxyphenyl)-4H-chromene;
2-Amino-3-cyano-7-methoxy-4-(3,5-difluorophenyl)-4H-chromene;
2-Amino-3-cyano-4-(3,5-difluorophenyl)-4H-indolo[4,5-b]pyran;
2-Amino-3-cyano-4-(3-fluorophenyl)-4H-indolo[4,5-b]pyran;
2-Amino-3-cyano-7-amino-4-(3-fluorophenyl)-4H-chromene;
2-Amino-3-cyano-7-methoxy-4-(3-fluorophenyl)-4H-chromene;
2-Amino-3-cyano-7-amino-4-(3,5-difluorophenyl)-4H-chromene;
2-Amino-3-cyano-7-methoxy-4-(3,4,5-trimethoxyphenyl)-4H-chromene;
2-Amino-3-cyano-7-methoxy-4-(3-methoxyphenyl)-4H-chromene;
2-Amino-3-cyano-7-methoxy-4-(3-cyanophenyl)-4H-chromene;
2-Amino-3-cyano-7-methoxy-4-(3-bromophenyl)-4H-chromene;
2-Amino-3-cyano-7-ethylamino-4-(3-bromophenyl)-4H-chromene;
2-Amino-3-cyano-7-ethylamino-4-(3-chlorophenyl)-4H-chromene;
2-Amino-3-cyano-7-ethylamino-4-(3-nitrophenyl)-4H-chromene;
2-Amino-3-cyano-7-methoxy-4-(3-chlorophenyl)-4H-chromene;
2-Amino-3-cyano-7-methoxy-4-(3-nitrophenyl)-4H-chromene;
2-Amino-3-cyano-7-methoxy-4-(3,5-dimethoxyphenyl)-4H-chromene;
2-Amino-3-cyano-7-ethylamino-4-(3,4,5-trimethoxyphenyl)-4H-chromene;
2-Amino-3-cyano-7-ethylamino-4-(3,5-dimethoxyphenyl)-4H-chromene;
2-Amino-3-cyano-7-ethylamino-4-(3-methoxyphenyl)-4H-chromene;
2-Amino-3-cyano-7-ethylamino-4-(3-cyanophenyl)-4H-chromene;
2-Amino-3-cyano-7-methoxy-4-(3-pyridyl)-4H-chromene;
2-Amino-3-cyano-4-(3-pyridyl)-4H-indolo[4,5-b]pyran;
2,7-Diamino-3-cyano-4-(3-bromophenyl)-4H-chromene;

2,7-Diamino-3-cyano-4-(3-cyanophenyl)-4H-chromene;
2,7-Diamino-3-cyano-4-(3-methoxyphenyl)-4H-chromene;
2,7-Diamino-3-cyano-4-(3-chlorophenyl)-4H-chromene;
2,7-Diamino-3-cyano-4-(3-methylphenyl)-4H-chromene;
2,7-Diamino-3-cyano-4-(3-pyridyl)-4H-chromene;
2,7-Diamino-3-cyano-4-(3-nitrophenyl)-4H-chromene;
2-Amino-3-cyano-7-methoxy-4-phenyl-4H-chromene;
2-Amino-3-cyano-7-methoxy-4-(2,4-dimethoxypyrimidinyl)-4H-chromene;
2-Amino-3-cyano-7-methoxy-4-(1,2,3,6-tetrahydrophenyl)-4H-chromene;
2-Amino-3-cyano-7-methoxy-4-(5-methyl-3-pyridyl)-4H-chromene;
2-Amino-3-cyano-7-ethylamino-4-(5-methyl-3-pyridyl)-4H-chromene;
2-Amino-3-cyano-4-(5-bromo-3-pyridyl)-7-ethylamino-4H-chromene;
2-Amino-3-cyano-4-(5-bromo-3-pyridyl)-7-methoxy-4H-chromene;
2,7-Diamino-3-cyano-4-(5-methyl-3-pyridyl)-4H-chromene;
2-Amino-3-cyano-4-(5-methyl-3-pyridyl)-4H-indolo[4,5-b]pyran;
2-Amino-3-cyano-4-(5-bromo-3-pyridyl)-4H-indolo[4,5-b]pyran;
2,7-Diamino-3-cyano-4-(5-bromo-3-pyridyl)-4H-chromene;
2,7-Diamino-3-cyano-4-(5-methoxy-3-pyridyl)-4H-chromene;
2-Amino-3-cyano-7-methoxy-4-(5-methoxy-pyridin-3-yl)-4H-chromene;
2-Amino-3-cyano-4-(5-methoxy-pyridin-3-yl)-4H-indolo[4,5-b]pyran;
2-Amino-3-cyano-4-(3-bromo-4,5-dimethoxyphenyl)-4H-indolo[7,6-b]pyran;
2-Amino-3-cyano-4-(3-methoxyphenyl)-4H-indolo[7,6-b]pyran;
3-Cyano-2,7,8-triamino-4-(3-methoxyphenyl)-4H-chromene;
3-Cyano-2,7,8-triamino-4-(3-bromo-4,5-dimethoxyphenyl)-4H-chromene;
2-Amino-3-cyano-4-(3-methoxyphenyl)-4H-indolo[4,5-b]pyran;
2-Amino-6-chloro-3-cyano-7-methyl-4-phenyl-4H-chromene;
2-Amino-4-(3-bromo-4-hydroxy-5-methoxyphenyl)-3-cyano-7-dimethylamino-4H-chromene;
3-Cyano-4-(3-bromo-4-hydroxy-5-methoxyphenyl)-2,7-diamino-4H-chromene;
2-Amino-4-(3-bromo-4-hydroxy-5-methoxyphenyl)-3-cyano-4H-indolo[4,5-b]pyran;
2-Amino-4-(3-bromo-4-hydroxy-5-methoxyphenyl)-3-cyano-4H-indolo[7,6-b]pyran;
2-Amino-3-cyano-4-(3,5-dimethoxyphenyl)-4H-indolo[7,6-b]pyran;
2-Amino-3-cyano-4-(3-cyano-phenyl)-4H-indolo[7,6-b]pyran;
2-Amino-3-cyano-4-(3-trifluromethyl-phenyl)-4H-indolo[7,6-b]pyran;
2-Amino-3-cyano-4-(5-methyl-pyridin-3-yl)-4H-indolo[7,6-b]pyran;
2-Amino-3-cyano-4-(5-cyano-pyridin-3-yl)-4H-indolo[4,5-b]pyran;
2-Amino-3-cyano-4-(6-methyl-pyrazin-2-yl)-4H-indolo[4,5-b]pyran;
2-Amino-3-cyano-4-(quinoxalin-2-yl)-4H-indolo[4,5-b]pyran;
2-Amino-3-cyano-4-(5-cyano-pyridin-3-yl)-4H-indolo[7,6-b]pyran;
2-Amino-3-cyano-4-(6-methyl-pyrazin-2-yl)-4H-indolo[7,6-b]pyran;
2-Amino-7-bromo-4-(3-bromo-4,5-dimethoxy-phenyl)-3-cyano-4H-chromene;
2-Amino-4-(3-bromo-4,5-dimethoxy-phenyl)-7-chloro-3-cyano-4H-chromene;
2-Amino-3-cyano-4-(3-bromo-4,5-dimethoxyphenyl)-4H-imidazo[4,5-h]chromene;
2-Amino-3-cyano-4-(3-bromo-4,5-dimethoxy-phenyl)-8-methyl-4H-imidazo[4,5-h]chromene
2-Amino-3-cyano-7-pyrrolidine-4-(3-bromo-4,5-dimethoxyphenyl)-4H-chromene;
2-Amino-3-cyano-7-piperazine-4-(3-bromo-4,5-dimethoxyphenyl)-4H-chromene;
2-Amino-3-cyano-7-N-morpholine-4-(3-bromo-4,5-dimethoxyphenyl)-4H-chromene;
2-Amino-3-cyano-7-pyrrole-4-(3-bromo-4,5-dimethoxyphenyl)-4H-chromene;
2-Amino-3-cyano-7-dimethylamino-4-(3-bromo-4,5-dimethoxyphenyl-4-methylchromene;
2-Amino-3-cyano-4-phenyl-4-methylchromene;
2-Amino-3-cyano-4-(3-bromo-4-phosphoric acid-di piperidine salt-5-methoxyphenyl)-4H-indolo[4,5-b]pyran;
2-Amino-3-cyano-7-methoxy-4-(3-methoxyphenyl)-4H-thiochromene;
2-Amino-3-cyano-4-phenyl-1,4-dihydroquinoline;
2-Amino-3-ethoxycarboxyl-4-(3-bromo-4,5-dimethoxyphenyl)-4H-indolo[4,5-b]pyran;
2-Amino-3-methylcarboxyl-4-(3-bromo-4,5-dimethoxyphenyl)-4H-indolo[4,5-b]pyran;
2-Amino-3-cyano-7-amino-8-hydroxy-4-(3-bromo-4,5-dimethoxyphenyl)-4H-chromene;
2-Amino-4-(3-bromo-4,5-dimethoxyphenyl)-3-cyano-9-methyl-4H-imidazo[4,5-h]chromene;
3-Cyano-4-(3-bromo-4,5-dimethoxyphenyl)-2-methylamino-9-methyl-4H-pyrrolo[3,2-h]chromene;
2-Amino-4-(3-bromo-4,5-dimethoxyphenyl)-3-cyano-9-methyl-4H-pyrrolo[3,2-h]chromene;
2-Amino-3-cyano-4-(3-methoxyphenyl)-4H-pyrazino[2,3-h]chromene;
2-Amino-3-cyano-4-(3-bromo-4,5-dimethoxyphenyl)-4H-pyrazino[2,3-h]chromene;
2-Amino-3-cyano-4-(3-bromo-4,5-dimethoxyphenyl)-8-oxo-4,7,8,9-tetrahydroimidazo[4,5-h]chromene;
2-Amino-3-cyano-4-(3,4,5-trimethoxyphenyl)-4H-indolo[7,6-b]pyran;
2-Amino-3-cyano-4-(3-methoxyphenyl)-4H-indolo[7,6-b]pyran;
2-Amino-3-cyano-7,8-methylenedioxy-4-(3-bromo-4,5-dimethoxyphenyl)-4H-chromene;
2-Amino-3-cyano-7,8-methylenedioxy-4-(3-methoxyphenyl)-4H-chromene;
2-Amino-3-cyano-4-(3-methoxyphenyl)-4H-imidazo[4,5-h]chromene;
2-Amino-3-cyano-4-(3-bromo-4,5-dimethoxyphenyl)-4H-furo[2,3-h]chromene;
2-Amino-3-cyano-4-(3-methoxyphenyl)-4H-furo[2,3-h]chromen;
2-Amino-3-cyano-4-(3-bromo-4,5-dimethoxyphenyl)-4H-thieno[2,3-h]chromene;
2-Amino-3-cyano-4-(3-methoxyphenyl)-4H-pyrazo[2,3-h]chromene;
2-Amino-3-cyano-4-(3-bromo-4,5-dimethoxyphenyl)-4H-pyrazo[2,3-h]chromene;
2,7-Diamino-3-cyano-4-phenyl-4H-chromene;

2,7-Diamino-3-cyano-4-(3-iodophenyl)-4H-chromene;
2,7-Diamino-3-cyano-4-(3,4,5-trimethoxyphenyl)-4H-chromene;
2-Amino-3-cyano-7-hydroxy-4-(3,4,5-trimethoxyphenyl)-4H-chromene;
2-Amino-3-cyano-7-(2-methylbutanoylamino)-4-(3-bromo-4,5-dimethoxyphenyl)-4H-chromene;
2-Amino-3-cyano-7-dimethylamino-4-(3-(2-phenylbutanoyloxy)phenyl)-4H-chromene;
2-Amino-3-cyano-7-dimethylamino-4-(3-(2-methylbutanoyloxy)phenyl)-4H-chromene;
2-Amino-3-cyano-4-(3-bromo-4,5-dimethoxyphenyl)-4H-chromene;
2-Amino-3-cyano-4-(3-methoxyphenyl)-8-oxo-4,7,8,9-tetrahydroimidazo[4,5-h]chromene;
2-Amino-3-cyano-4-(3-methoxyphenyl)-4,7,8,9,10-pentahydro-8,9-dioxypyrazine[2,3-h]chromene;
2-Amino-3-cyano-4-(3-bromo-4,5-dimethoxy-phenyl)-4,7,8,9,10-pentahydro-8,9-dioxypyrazine[2,3-h]chromene.

and pharmaceutically acceptable salts or prodrugs thereof.

The present invention is also directed to novel compounds within the scope of Formulae I–III:

2-Amino-3-cyano-7-hydroxy-4-(3-bromo-4,5-dimethoxyphenyl)-4H-chromene;
2-Amino-3-cyano-7-ethylamino-4-(3-bromo-4,5-dimethoxyphenyl)-4H-chromene;
2-Amino-3-cyano-7-hydroxy-4-(3-cyanophenyl)-4H-chromene;
2-Amino-3-cyano-7,8-dihydroxy-4-(3-bromo-4,5-dimethoxyphenyl)-4H-chromene;
2-Amino-3-cyano-7-amino-4-(3,5-dichlorophenyl)-4H-chromene;
2-Amino-3-cyano-7-methoxy-4-(3,5-dichlorophenyl)-4H-chromene;
2-Amino-3-cyano-4-(3,5-dichlorophenyl)-4H-indolo[4,5-b]pyran;
2-Amino-3-cyano-4-(3-chlorophenyl)-4H-indolo[4,5-b]pyran;
2-Amino-3-cyano-7-amino-8-methyl-4-(3-bromo-4,5-dimethoxyphenyl)-4H-chromene;
2-Amino-3-cyano-7-hydroxy-8-amino-4-(3-bromo-4,5-dimethoxyphenyl)-4H-chromene;
2-Amino-3-cyano-7-methoxy-4-(3,5-difluorophenyl)-4H-chromene;
2-Amino-3-cyano-4-(3,5-difluorophenyl)-4H-indolo[4,5-b]pyran;
2-Amino-3-cyano-4-(3-fluorophenyl)-4H-indolo[4,5-b]pyran;
2-Amino-3-cyano-7-amino-4-(3-fluorophenyl)-4H-chromene;
2-Amino-3-cyano-7-methoxy-4-(3-fluorophenyl)-4H-chromene;
2-Amino-3-cyano-7-amino-4-(3,5-difluorophenyl)-4H-chromene;
2-Amino-3-cyano-7-methoxy-4-(3,4,5-trimethoxyphenyl)-4H-chromene;
2-Amino-3-cyano-7-methoxy-4-(3-methoxyphenyl)-4H-chromene;
2-Amino-3-cyano-7-methoxy-4-(3-cyanophenyl)-4H-chromene;
2-Amino-3-cyano-7-methoxy-4-(3-bromophenyl)-4H-chromene;
2-Amino-3-cyano-7-ethylamino-4-(3-bromophenyl)-4H-chromene;
2-Amino-3-cyano-7-ethylamino-4-(3-chlorophenyl)-4H-chromene;
2-Amino-3-cyano-7-ethylamino-4-(3-nitrophenyl)-4H-chromene;
2-Amino-3-cyano-7-methoxy-4-(3-chlorophenyl)-4H-chromene;
2-Amino-3-cyano-7-methoxy-4-(3-nitrophenyl)-4H-chromene;
2-Amino-3-cyano-7-methoxy-4-(3,5-dimethoxyphenyl)-4H-chromene;
2-Amino-3-cyano-7-ethylamino-4-(3,4,5-trimethoxyphenyl)-4H-chromene;
2-Amino-3-cyano-7-ethylamino-4-(3,5-dimethoxyphenyl)-4H-chromene;
2-Amino-3-cyano-7-ethylamino-4-(3-methoxyphenyl)-4H-chromene;
2-Amino-3-cyano-7-ethylamino-4-(3-cyanophenyl)-4H-chromene;
2-Amino-3-cyano-7-methoxy-4-(3-pyridyl)-4H-chromene;
2-Amino-3-cyano-4-(3-pyridyl)-4H-indolo[4,5-b]pyran;
2,7-Diamino-3-cyano-4-(3-bromophenyl)-4H-chromene;
2,7-Diamino-3-cyano-4-(3-cyanophenyl)-4H-chromene;
2,7-Diamino-3-cyano-4-(3-methoxyphenyl)-4H-chromene;
2,7-Diamino-3-cyano-4-(3-chlorophenyl)-4H-chromene;
2,7-Diamino-3-cyano-4-(3-methylphenyl)-4H-chromene;
2,7-Diamino-3-cyano-4-(3-pyridyl)-4H-chromene;
2,7-Diamino-3-cyano-4-(3-nitrophenyl)-4H-chromene;
2-Amino-3-cyano-7-methoxy-4-phenyl-4H-chromene;
2-Amino-3-cyano-7-methoxy-4-(2,4-dimethoxypyrimidinyl)-4H-chromene;
2-Amino-3-cyano-7-methoxy-4-(1,2,3,6-tetrahydrophenyl)-4H-chromene;
2-Amino-3-cyano-7-methoxy-4-(5-methyl-3-pyridyl)-4H-chromene;
2-Amino-3-cyano-7-ethylamino-4-(5-methyl-3-pyridyl)-4H-chromene;
2-Amino-3-cyano-4-(5-bromo-3-pyridyl)-7-ethylamino-4H-chromene;
2-Amino-3-cyano-4-(5-bromo-3-pyridyl)-7-methoxy-4H-chromene;
2,7-Diamino-3-cyano-4-(5-methyl-3-pyridyl)-4H-chromene;
2-Amino-3-cyano-4-(5-methyl-3-pyridyl)-4H-indolo[4,5-b]pyran;
2-Amino-3-cyano-4-(5-bromo-3-pyridyl)-4H-indolo[4,5-b]pyran;
2,7-Diamino-3-cyano-4-(5-bromo-3-pyridyl)-4H-chromene;
2,7-Diamino-3-cyano-4-(5-methoxy-3-pyridyl)-4H-chromene;
2-Amino-3-cyano-7-methoxy-4-(5-methoxy-pyridin-3-yl)-4H-chromene;
2-Amino-3-cyano-4-(5-methoxy-pyridin-3-yl)-4H-indolo[4,5-b]pyran;
2-Amino-3-cyano-4-(3-bromo-4,5-dimethoxyphenyl)-4H-indolo[7,6-b]pyran;
2-Amino-3-cyano-4-(3-methoxyphenyl)-4H-indolo[7,6-b]pyran;
3-Cyano-2,7,8-triamino-4-(3-methoxyphenyl)-4H-chromene;
3-Cyano-2,7,8-triamino-4-(3-bromo-4,5-dimethoxyphenyl)-4H-chromene;
2-Amino-3-cyano-4-(3-methoxyphenyl)-4H-indolo[4,5-b]pyran;
2-Amino-6-chloro-3-cyano-7-methyl-4-phenyl-4H-chromene;
2-Amino-4-(3-bromo-4-hydroxy-5-methoxyphenyl)-3-cyano-7-dimethylamino-4H-chromene;

3-Cyano-4-(3-bromo-4-hydroxy-5-methoxyphenyl)-2,7-diamino-4H-chromene;
2-Amino-4-(3-bromo-4-hydroxy-5-methoxyphenyl)-3-cyano-4H-indolo[4,5-b]pyran;
2-Amino-4-(3-bromo-4-hydroxy-5-methoxyphenyl)-3-cyano-4H-indolo[7,6-b]pyran;
2-Amino-3-cyano-4-(3,5-dimethoxyphenyl)-4H-indolo[7,6-b]pyran;
2-Amino-3-cyano-4-(3-cyano-phenyl)-4H-indolo[7,6-b]pyran;
2-Amino-3-cyano-4-(3-trifluromethyl-phenyl)-4H-indolo[7,6-b]pyran;
2-Amino-3-cyano-4-(5-methyl-pyridin-3-yl)-4H-indolo[7,6-b]pyran;
2-Amino-3-cyano-4-(5-cyano-pyridin-3-yl)-4H-indolo[4,5-b]pyran;
2-Amino-3-cyano-4-(6-methyl-pyrazin-2-yl)-4H-indolo[4,5-b]pyran;
2-Amino-3-cyano-4-(quinoxalin-2-yl)-4H-indolo[4,5-b]pyran;
2-Amino-3-cyano-4-(5-cyano-pyridin-3-yl)-4H-indolo[7,6-b]pyran;
2-Amino-3-cyano-4-(6-methyl-pyrazin-2-yl)-4H-indolo[7,6-b]pyran;
2-Amino-7-bromo-4-(3-bromo-4,5-dimethoxy-phenyl)-3-cyano-4H-chromene;
2-Amino-4-(3-bromo-4,5-dimethoxy-phenyl)-7-chloro-3-cyano-4H-chromene;
2-Amino-3-cyano-4-(3-bromo-4,5-dimethoxyphenyl)-4H-imidazo[4,5-h]chromene;
2-Amino-3-cyano-4-(3-bromo-4,5-dimethoxy-phenyl)-8-methyl-4H-imidazo[4,5-h]chromene
2-Amino-3-cyano-7-pyrrolidine-4-(3-bromo-4,5-dimethoxyphenyl)-4H-chromene;
2-Amino-3-cyano-7-piperazine-4-(3-bromo-4,5-dimethoxyphenyl)-4H-chromene;
2-Amino-3-cyano-7-N-morpholine-4-(3-bromo-4,5-dimethoxyphenyl)-4H-chromene;
2-Amino-3-cyano-7-pyrrole-4-(3-bromo-4,5-dimethoxyphenyl)-4H-chromene;
2-Amino-3-cyano-7-dimethylamino-4-(3-bromo-4,5-dimethoxyphenyl-4-methylchromene;
2-Amino-3-cyano-4-phenyl-4-methylchromene;
2-Amino-3-cyano-4-(3-bromo-4-phosphoric acid-di piperidine salt-5-methoxyphenyl)-4H-indolo[4,5-b]pyran;
2-Amino-3-cyano-7-methoxy-4-(3-methoxyphenyl)-4H-thiochromene;
2-Amino-3-cyano-4-phenyl-1,4-dihydroquinoline;
2-Amino-3-ethoxycarboxyl-4-(3-bromo-4,5-dimethoxyphenyl)-4H-indolo[4,5-b]pyran;
2-Amino-3-methylcarboxyl-4-(3-bromo-4,5-dimethoxyphenyl)-4H-indolo[4,5-b]pyran;
2-Amino-3-cyano-7-amino-8-hydroxy-4-(3-bromo-4,5-dimethoxyphenyl)-4H-chromene;
2-Amino-4-(3-bromo-4,5-dimethoxyphenyl)-3-cyano-9-methyl-4H-imidazo[4,5-h]chromene;
3-Cyano-4-(3-bromo-4,5-dimethoxyphenyl)-2-methylamino-9-methyl-4H-pyrrolo[3,2-h]chromene;
2-Amino-4-(3-bromo-4,5-dimethoxyphenyl)-3-cyano-9-methyl-4H-pyrrolo[3,2-h]chromene;
2-Amino-3-cyano-4-(3-methoxyphenyl)-4H-pyrazino[2,3-h]chromene;
2-Amino-3-cyano-4-(3-bromo-4,5-dimethoxy-phenyl)-4H-pyrazino[2,3-h]chromene;
2-Amino-3-cyano-4-(3-bromo-4,5-dimethoxy-phenyl)-8-oxo-4,7,8,9-tetrahydroimidazo[4,5-h]chromene;
2-Amino-3-cyano-4-(3,4,5-trimethoxyphenyl)-4H-indolo[7,6-b]pyran;
2-Amino-3-cyano-4-(3-methoxyphenyl)-4H-indolo[7,6-b]pyran;
2-Amino-3-cyano-7,8-methylenedioxy-4-(3-bromo-4,5-dimethoxyphenyl)-4H-chromene;
2-Amino-3-cyano-7,8-methylenedioxy-4-(3-methoxyphenyl)-4H-chromene;
2-Amino-3-cyano-4-(3-methoxyphenyl)-4H-imidazo[4,5-h]chromene;
2-Amino-3-cyano-4-(3-bromo-4,5-dimethoxyphenyl)-4H-furo[2,3-h]chromene;
2-Amino-3-cyano-4-(3-methoxyphenyl)-4H-furo[2,3-h]chromen;
2-Amino-3-cyano-4-(3-bromo-4,5-dimethoxyphenyl)-4H-thieno[2,3-h]chromene;
2-Amino-3-cyano-4-(3-methoxyphenyl)-4H-pyrazo[2,3-h]chromene;
2-Amino-3-cyano-4-(3-bromo-4,5-dimethoxyphenyl)-4H-pyrazo[2,3-h]chromene;
2,7-Diamino-3-cyano-4-phenyl-4H-chromene;
2,7-Diamino-3-cyano-4-(3-iodophenyl)-4H-chromene;
2,7-Diamino-3-cyano-4-(3,4,5-trimethoxyphenyl)-4H-chromene;
2-Amino-3-cyano-7-hydroxy-4-(3,4,5-trimethoxyphenyl)-4H-chromene;
2-Amino-3-cyano-7-(2-methylbutanoylamino)-4-(3-bromo-4,5-dimethoxyphenyl)-4H-chromene;
2-Amino-3-cyano-7-dimethylamino-4-(3-(2-phenylbutanoyloxy)-phenyl)-4H-chromene;
2-Amino-3-cyano-7-dimethylamino-4-(3-(2-methylbutanoyloxy)-phenyl)-4H-chromene;
2-Amino-3-cyano-4-(3-bromo-4,5-dimethoxyphenyl)-4H-chromene;
2-Amino-3-cyano-4-(3-methoxyphenyl)-8-oxo-4,7,8,9-tetrahydroimidazo[4,5-h]chromene;
2-Amino-3-cyano-4-(3-methoxyphenyl)-4,7,8,9,10-pentahydro-8,9-dioxypyrazine[2,3-h]chromene;
2-Amino-3-cyano-4-(3-bromo-4,5-dimethoxy-phenyl)-4,7,8,9,10-pentahydro-8,9-dioxypyrazine[2,3-h]chromene.

and pharmaceutically acceptable salts or prodrugs thereof.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group can be optionally substituted.

Optional substituents on the alkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl($C_2$–$C_6$) alkynyl, saturated and unsaturated heterocyclic or heteroaryl. Optional substituents on the aryl, aralkyl and heteroaryl groups include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylalkyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Certain of the compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623–3628 (1999)) and Greenwald, et. al., (*J. Med. Chem.* 42:3657–3667 (1999)); acetals and ketals of alcohol containing compounds (e.g., those obtained by condensation with chloromethyl methyl ether or chloromethyl ethyl ether according to methods known in the art); and phosphonato and phosphono compounds (e.g., those obtained by condensation with a phosphate ester, phosphoryl chloride, or phosphoric acid), which include pharmaceutically acceptable mono-basic and di-basic addition salts of the phosphono group, e.g., organic bases, such as amine bases, which include ammonia, piperidine and morpholine.

The compounds of this invention may be prepared using methods known to those skilled in the art, or the novel methods of this invention. Specifically, the compounds of this invention with Formulae I–III can be prepared as illustrated by exemplary reaction in Scheme 1. Reaction of a phenol with a benzaldehyde and malononitrile in the presence a base such as piperidine or N,N-diisopropylethylamine produced the substituted chromene. The reaction also can be run by reacting an aldehyde with malononitrile in the presence a base such as piperidine first, the intermediate was then treated with a phenol and cyclized to yield the final product as shown by exemplary reactions in Scheme 2. Reaction of 3-aminophenol with a benzaldehyde and malononitrile in the presence a base, such as piperidine produced the substituted chromene as shown by exemplary reaction in Scheme 3.

SCHEME 1

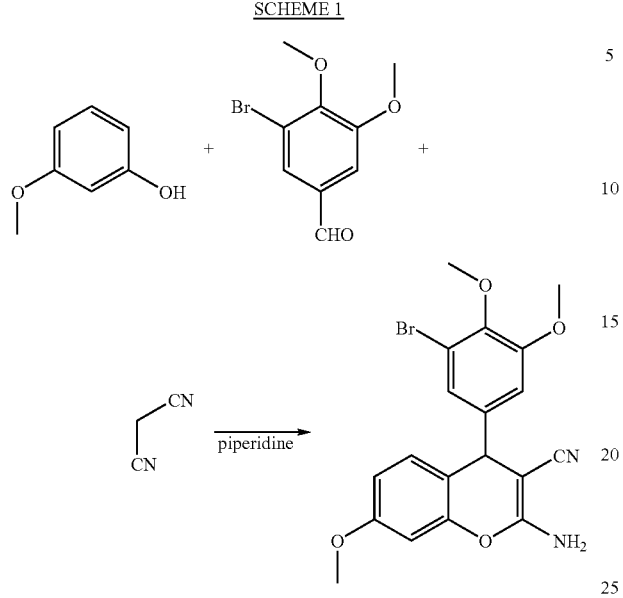

SCHEME 2

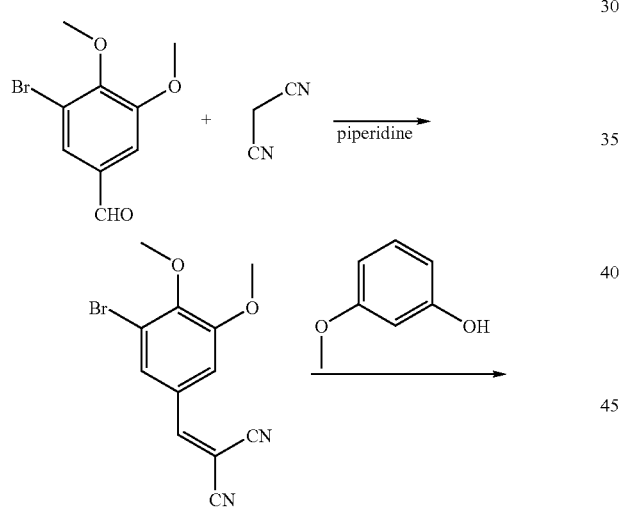

SCHEME 3

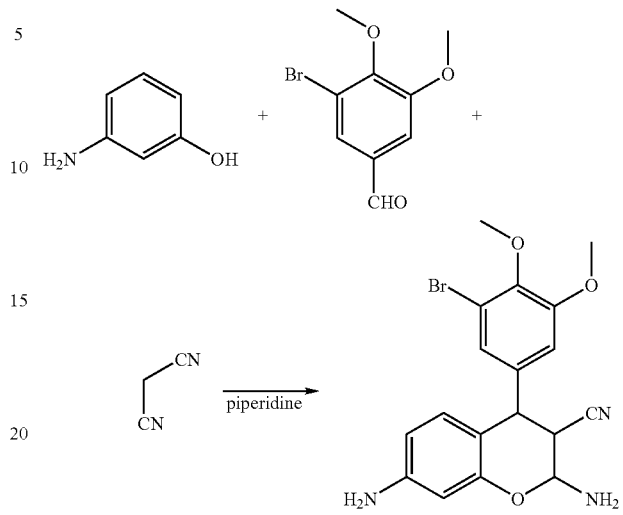

Compounds of this invention with Formulae I–III can also be prepared as illustrated by exemplary reaction in Scheme 4. Reaction of a substituted phenol, such as 2,3-methylenedioxyphenol with a substituted benzaldehyde, such as 3-methoxybenzaldehyde and malononitrile in the presence a base, such as piperidine or N,N-diisopropylethylamine, produced the 7,8-fused chromene.

SCHEME 4

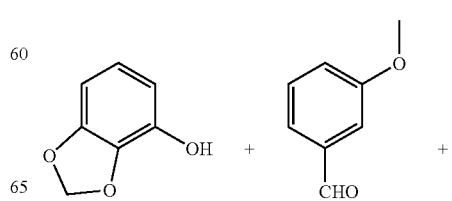

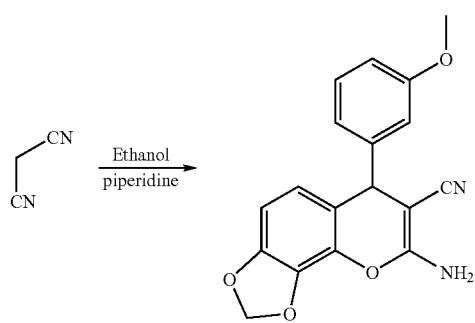

Similarly, other 7,8-fused chromenes can be prepared as shown in Scheme 5.

SCHEME 5

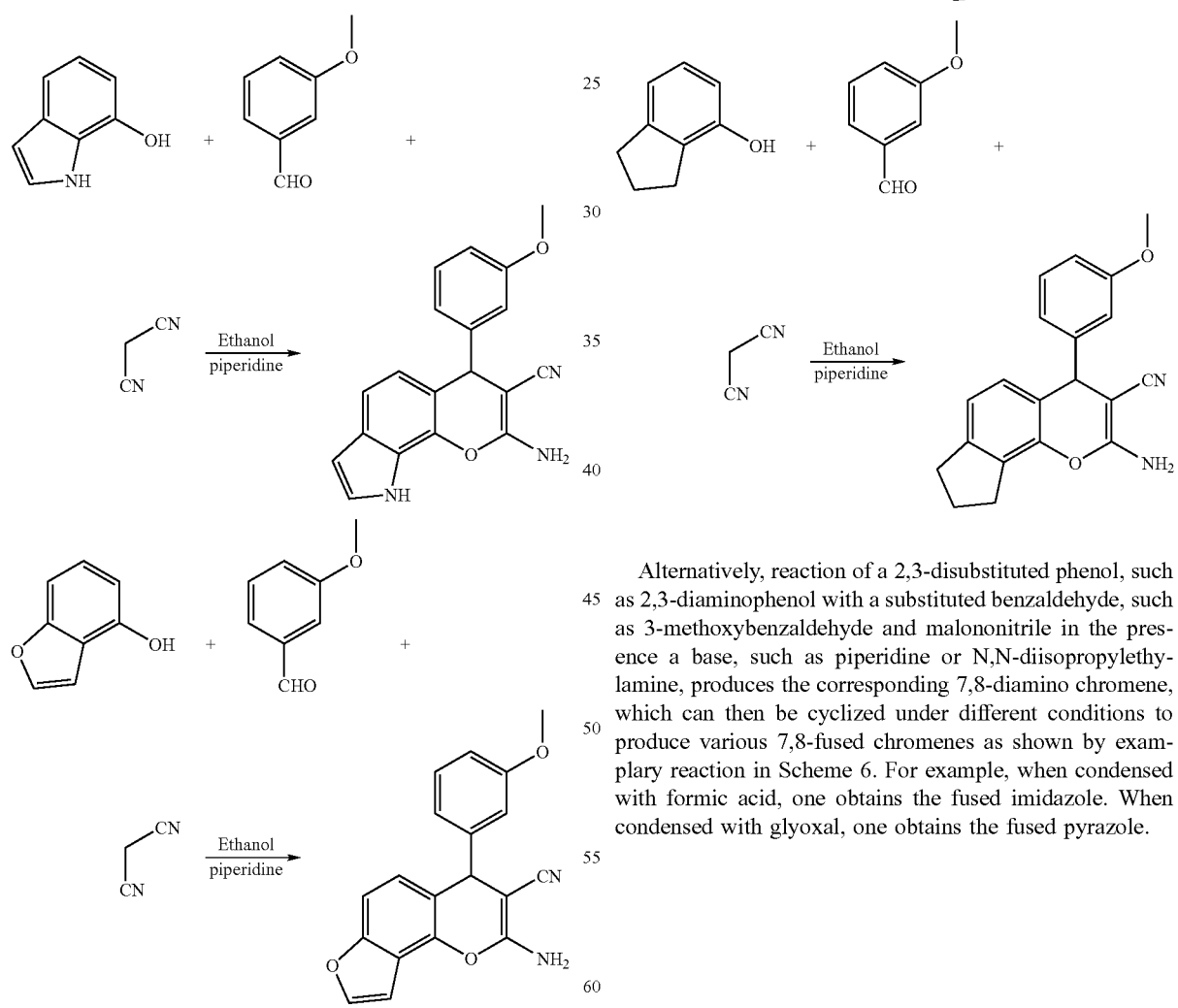

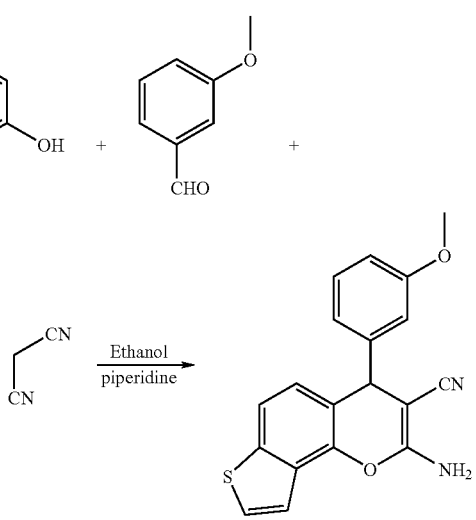

Alternatively, reaction of a 2,3-disubstituted phenol, such as 2,3-diaminophenol with a substituted benzaldehyde, such as 3-methoxybenzaldehyde and malononitrile in the presence a base, such as piperidine or N,N-diisopropylethylamine, produces the corresponding 7,8-diamino chromene, which can then be cyclized under different conditions to produce various 7,8-fused chromenes as shown by exemplary reaction in Scheme 6. For example, when condensed with formic acid, one obtains the fused imidazole. When condensed with glyoxal, one obtains the fused pyrazole.

SCHEME 6

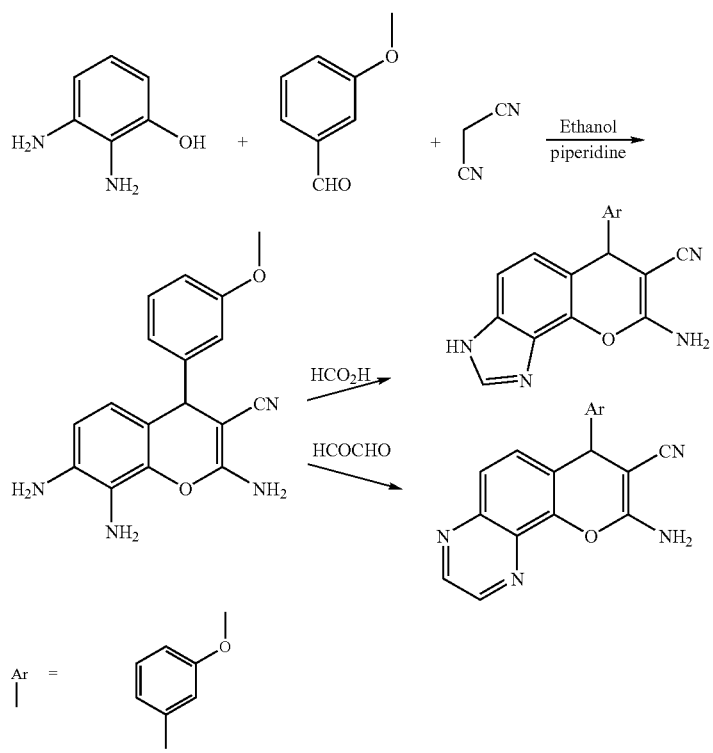

The compound 2-amino-3-cyan-4-phenyl-4H-chromene can be prepared as shown in Scheme 7.

SCHEME 7

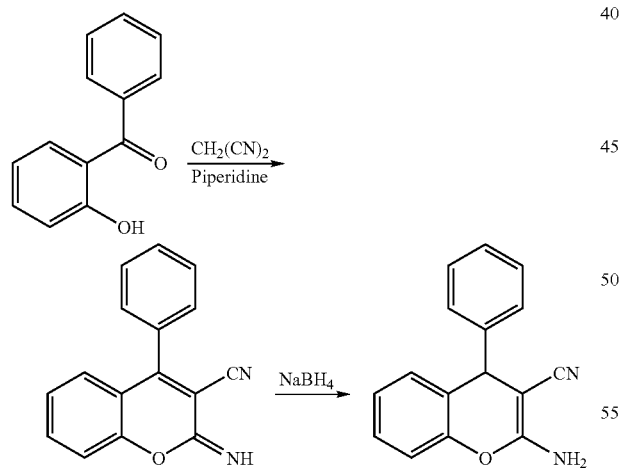

Substituted chromenes with electron withdrawing groups, such as Br or Cl, can be prepared as illustrated by exemplary reaction in Scheme 8. Oxidation of a substituted 2-amino-4H-chromene, such as 4-(3-bromo-4,5-dimethoxy-phenyl)-3-cyano-2,7-diamino-4H-chromene by an oxidation agent, such as 2,3-dichloro-5,6-dicyano-1,4-benzoquinone (DDQ), produced the substituted 7-amino-2-imino-2H-chromene. Diazotization of the amino group in the 7-position in the presence of $CuBr_2$ converted the amino group into a Br group. Reduction of the substituted 2-imino-2H-chromene by a reducing agent, such as $NaBH_4$ converted the substituted 2-imino-2H-chromene back to a substituted 2-amino-4H-chromene, produced 7-bromo-4-(3-bromo-4,5-dimethoxy-phenyl)-3-cyano-2-amino-4H-chromene.

SCHEME 8

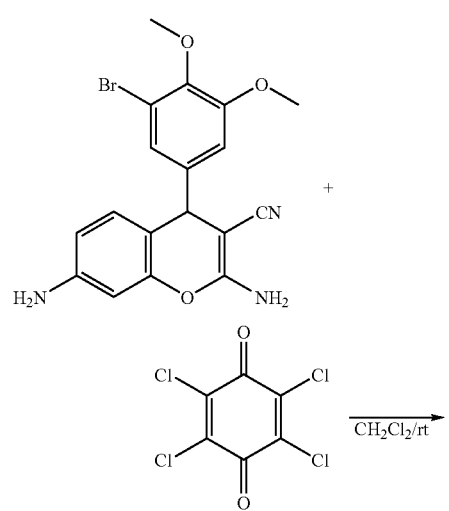

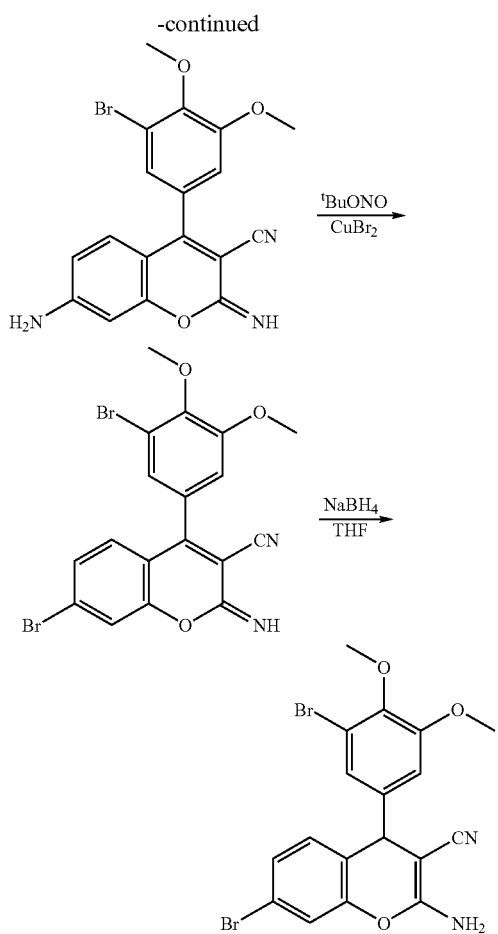
Some of the 3-substituted phenols can be prepared as illustrated by exemplary reactions in Scheme 9.
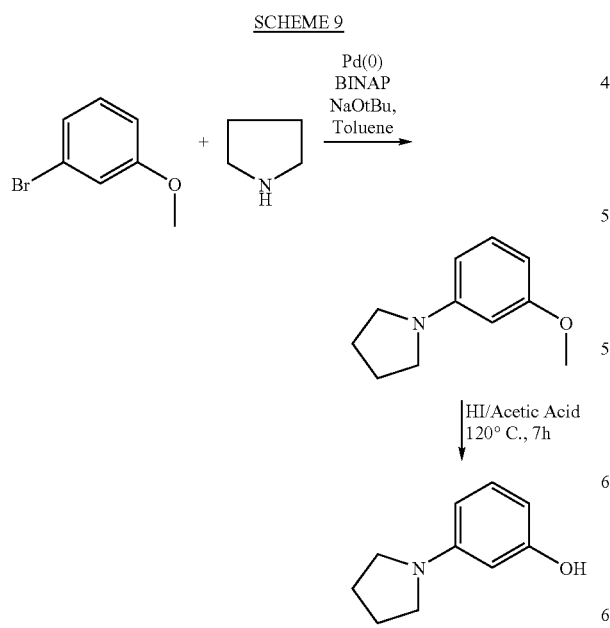
Chromenes with a pyrrole substituted in the 7-position can be prepared as illustrated by exemplary reaction in Scheme 10.
SCHEME 10
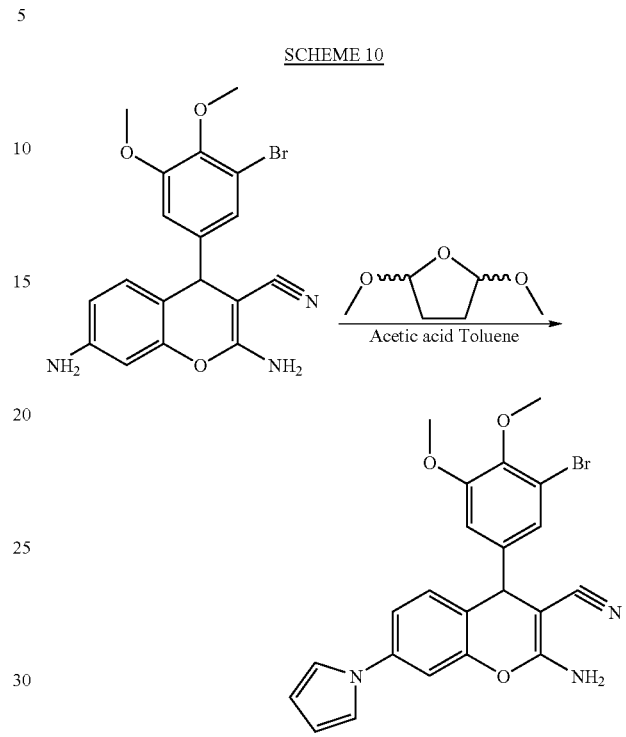
Chromemes with a methyl susbtituted in the 4-position can be prepared as illustrated by exemplary reactions in Scheme 11.
SCHEME 11
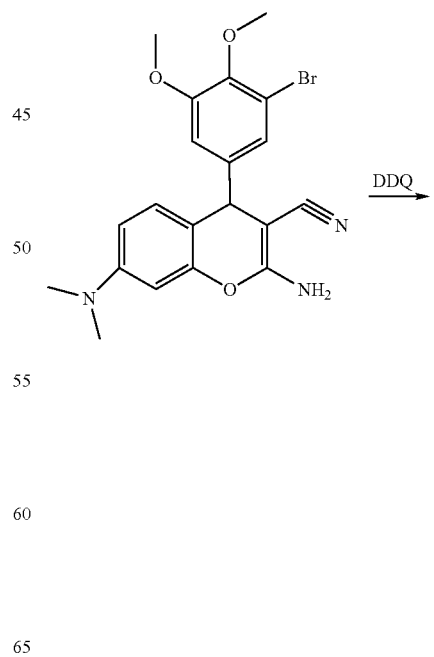

-continued
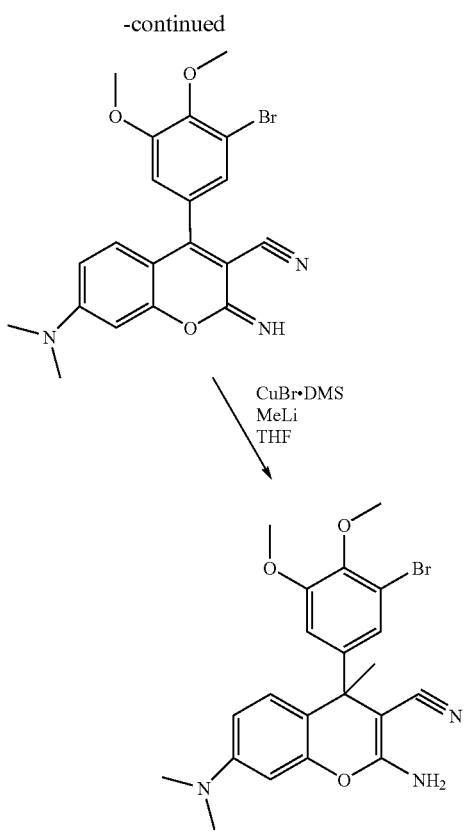
Chromenes with a phosphoric acid group susbtituted in the 4-phenyl group can be prepared as illustrated by exemplary reactions in Scheme 12.
SCHEME 12
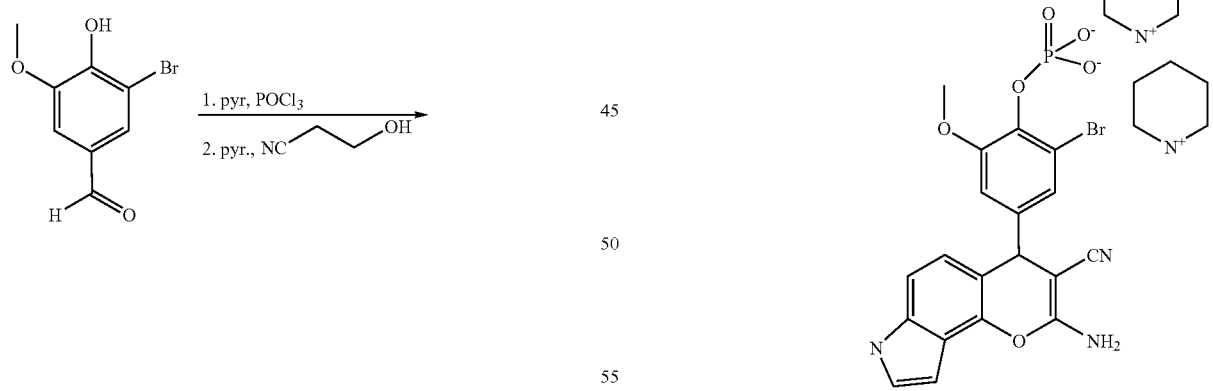
-continued
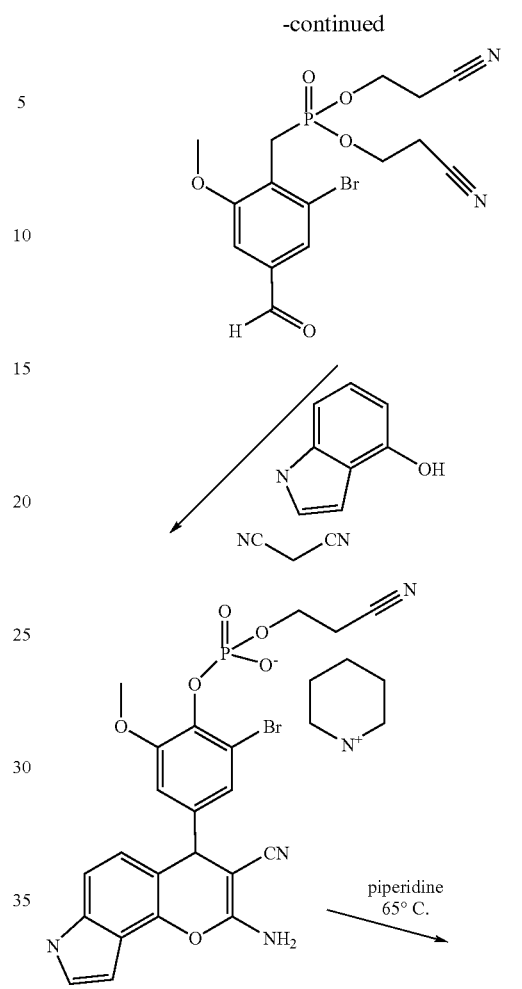
4H-Thiochromenes can be prepared as illustrated by exemplary reactions in Scheme 13.

SCHEME 13
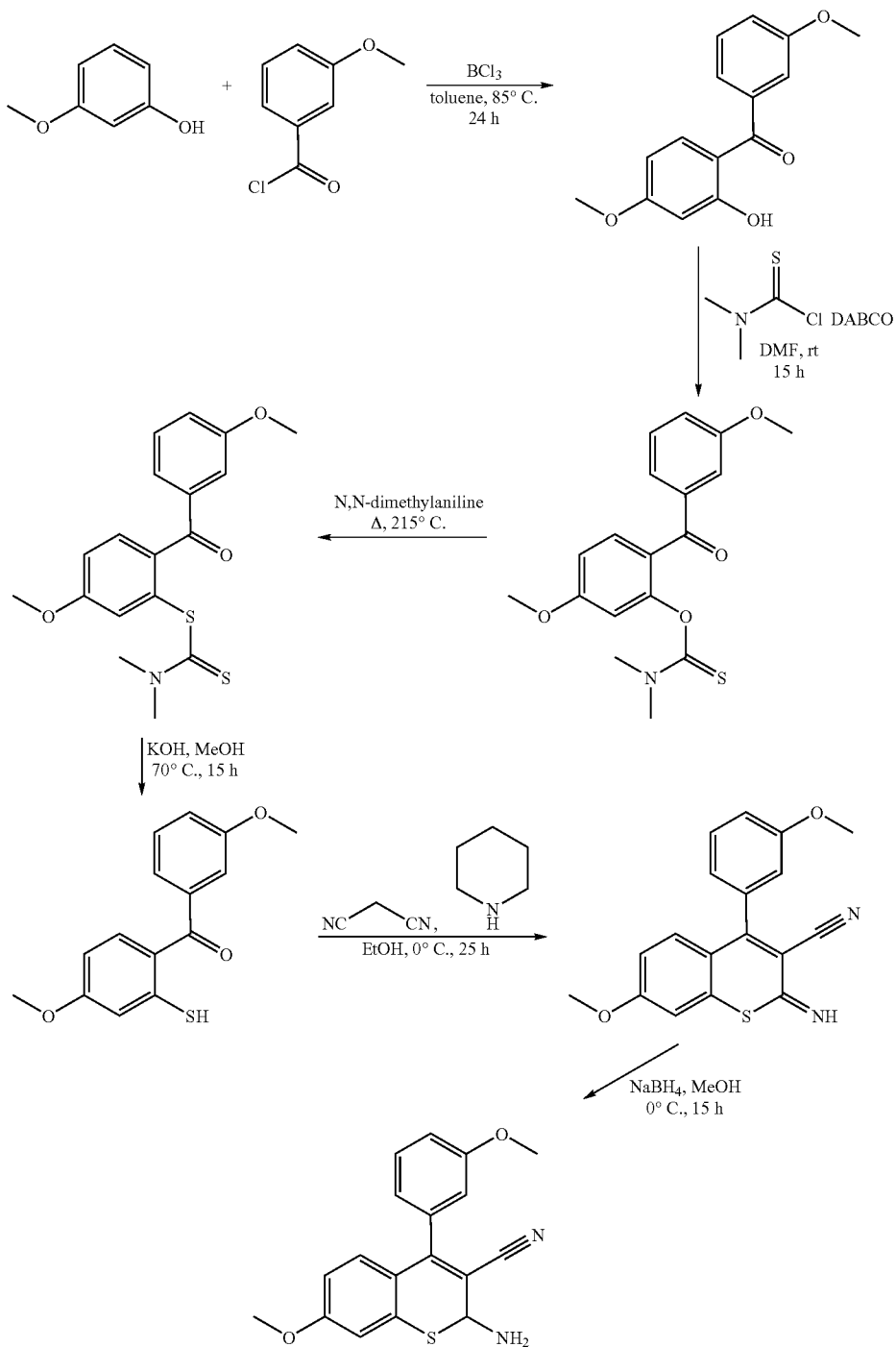
1,4-Dihydroquinolines can be prepared as illustrated by exemplary reactions in Scheme 14.

SCHEME 14

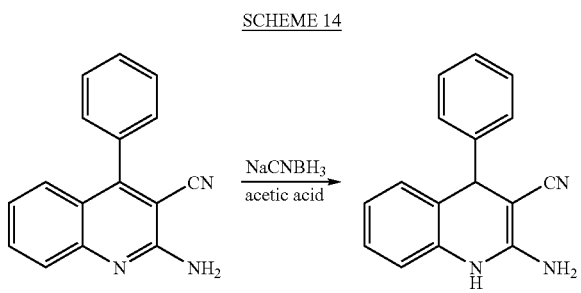

Chromenes with an ester group in the 3-positions can be prepared as illustrated by exemplary reaction in Scheme 15.

SCHEME 15

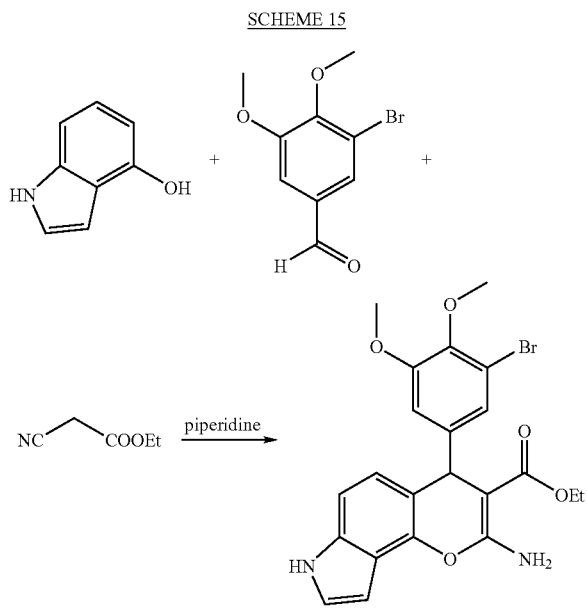

An important aspect of the present invention is the discovery that compounds having Formulae I–III are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I–III are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I–III, which functions as a caspase cascade activator and inducer of apoptosis.

The present invention also include a therapeutic method comprising administering to an animal an effective amount of a compound, or a pharmaceutically acceptable salt or prodrug of said compound of Formulae I–III, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphotic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinomas, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms In another embodiment, a pharmaceutical composition comprising a compound, or a pharmaceutically acceptable salt of said compound of Formulae I–III, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I–III, which functions as a caspase cascade activator and inducer of apoptosis, in combination with at least one known cancer chemotherapeutic agent, or a pharmaceutically acceptable salt of said agent. Examples of known anti-cancer agents, which can be used for combination therapy include, but are not limit to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from the at least one known cancer chemotherapeutic agent. In one embodiment, the compound of the invention and the at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I–III, which functions as a caspase cascade activator and inducer of apoptosis, in bioconjugation with at least one known therapeutically useful antibodies, such as Herceptin® or Rituxan®, growth factors such as DGF, NGF, cytokines such as IL-2, IL-4, or any molecule that binds to cell surface. The antibodies and other molecules will deliver compound of Formulae I–III to its targets and make them effective anticancer agents. The bioconjugates also could enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of said compound of Formulae I–III, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–III, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13–21 (1999)).

Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629–633 (1998) and Vaishnaw, A. K., et al., *J. Clin. Invest.* 103:355–363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475–483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42–48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I–III, which functions as a caspase cascade activator and inducer of apoptosis, is an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed.* 15:22–27 (1999), reported that lymphocytes treated with psoralen 8-MOP or TMP plus UVA displayed DNA degradation patterns typical of apoptotic cell death. Ozawa, et al., *J. Exp. Med.* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of the compound of Formulae I–III, which functions as a caspase cascade activator and inducer of apoptosis, is an effective treatment for hyperproliferative diseases, such as psoriasis.

Synovial cell hyperplasia is a characteristic of patients with rheumatoid arthritis (RA). Excessive proliferation of RA synovial cells, as well as defective in synovial cell death, might be responsible for the synovial cell hyperplasia. Wakisaka, et al., *Clin. Exp. Immunol.* 114:119–128 (1998), found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I–III, which functions as a caspase cascade activator and inducer of apoptosis, is an effective treatment for rheumatoid arthritis.

There have been accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375–380 (1997)). Boirivant, et al., *Gastroenterology* 116: 557–565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I–III, which functions as a caspase cascade activator and inducer of apoptosis, is an effective treatment for inflammation and inflammatory bowel disease.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day, of the body weight of the mammal being treated for apoptosis-mediated disorders. Preferably, approximately 0.01 to approximately 10 mg/kg is orally administered to treat or prevent such disorders. For intramuscular injection, the dose is generally approximately one-half of the oral dose. For example, a suitable intramuscular dose would be approximately 0.0025 to approximately 25 mg/kg, and most preferably, from approximately 0.01 to approximately 5 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

The unit oral dose may be comprised of approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations, which can be administered orally and that can be used for the preferred type of administration, such as tablets, dragees, and capsules, and also preparations which can be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400) or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers.

Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil such as almond oil with warm soft paraffin, and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

2-Amino-3-cyano-7-hydroxy-4-(3-bromo-4,5-dimethoxyphenyl)-4H-chromene

To a mixture of 3,4-dimethoxy-5-bromobenzylidenemalononitrile (293 mg, 1 mmol) and resorcinol (110 mg, 1 mmol) in ethanol (2 mL) was added piperidine (0.1 mL, 1 mmol). The mixture was refluxed for 2 h. The solvent was evaporated, the residue was purified by chromatography on silica gel with EtOAc and hexane (1:2) as eluant, yielding 240 mg (59.5%) of the title compound. $^1$H NMR (DMSO-$d_6$): 9.77 (brs, 1H), 6.96–6.86 (m, 5H), 6.52 (d, J=8.1, 1H), 6.41 (s, 1H), 4.65 (s, 1H), 3.80 (s, 3H), 3.70 (s, 3H).

EXAMPLE 2A

2-Amino-3-cyano-7-ethylamino-4-(3-bromo-4,5-dimethoxyphenyl)-4H-chromene

To a mixture of 5-bromoveratraldehyde (245 mg, 1 mmol) and malononitrile (66 mg, 1 mmol) in ethanol (2 mL) was added piperidine (0.1 ml, 1 mmol) and 3-ethylaminephenol (140 mg, 1 mmol). The mixture was stirred at room temperature overnight. The solvent was evaporated, the residue was purified by chromatography on silica gel with EtOAc and hexane (1:2) as eluant, yielding (330 mg, 76.7%) title compound. $^1$H NMR (CDCl$_3$): 6.88 (d, J=0.9 Hz, 1H), 6.71 (d, J=8.4 Hz, 2H), 6.32 (dd, J=2.1 Hz, 1H), 6.19 (d, J=2.1 Hz, 1H), 4.59 (s, 2H), 4.54 (s, 1H), 3.83 (d, J=0.6 Hz, 3H), 3.82 (d, J=0.9 Hz, 1H), 3.68 (brs, 1H), 3.12 (q, J=7.2 Hz, 2H), 1.28–1.23 (m, 3H).

The following compounds were prepared by a procedure similar to that described in Example 2A.

EXAMPLE 2B

2-Amino-3-cyano-7-hydroxy-4-(3-cyanophenyl)-4H-chromene $^1$H NMR (DMSO-d$_6$): 7.70–7.65 (m, 2H), 7.55–7.47 (m, 2H), 6.99 (brs, 2H), 6.79 (d, J=8.9 Hz, 1H), 6.48 (dd, J=2.5, 8.4 Hz, 1H), 6.40 (d, J=2.5 Hz, 1H), 4.76 (s, 1H) ppm.

EXAMPLE 2C

2-Amino-3-cyano-7,8-dihydroxy-4-(3-bromo-4,5-dimethoxyphenyl)-4H-chromene $^1$H NMR (CDCl$_3$): 6.88 (d, J=1.6 Hz, 1H), 6.80 (d, J=1.6 Hz, 1H), 6.54 (d, J=8.5 Hz, 1H), 6.30 (d, J=8.5 Hz, 1H), 4.95 (brs, 4H), 4.58 (s, 1H), 3.78 (s, 3H), 3.74 (s, 3H).

EXAMPLE 2D

2-Amino-3-cyano-7-amino-4-(3,5-dichlorophenyl)-4H-chromene $^1$H NMR (Acetone-d$_6$): 7.34 (t, J=1.8 Hz, 1H), 7.24 (d, J=2.0 Hz, 2H), 6.76 (d, J=8.4 Hz, 1H), 6.44 (dd, J=8.3, 2.2 Hz, 1H), 6.37 (d, J=2.2 Hz, 1H), 6.21 (brs, 2H), 4.92–4.90 (m, 2H), 4.70 (s, 1H).

EXAMPLE 2E

2-Amino-3-cyano-7-methoxy-4-(3,5-dichlorophenyl)-4H-chromene $^1$H NMR (CDCl$_3$): 7.24–7.23 (m, 1H), 7.07–7.06 (m, 2H), 6.83 (d, J=8.6 Hz, 1H), 6.65 (dd, J=2.2, 8.6 Hz, 1H), 6.55 (d, J=2.6 Hz, 1H), 4.65 (s, 1H), 4.64 (s, 2H), 3.79 (s, 3H).

EXAMPLE 2F

2-Amino-3-cyano-4-(3,5-dichlorophenyl)-4H-indolo[4,5-b]pyran $^1$H NMR (Acetone-d$_6$): 10.45 (brs, 1H), 7.38 (t, J=2.7 Hz, 1H), 7.34 (t, J=2.0 Hz, 1H), 7.29 (d, J=1.8 Hz, 2H), 7.20 (dd, J=8.4, 1.0 Hz, 1H), 6.78 (d, J=8.4 Hz, 1H), 6.57–6.56 (m, 1H), 6.36 (brs, 2H), 4.94 (s, 1H).

EXAMPLE 2G

2-Amino-3-cyano-4-(3-chlorophenyl)-4H-indolo[4,5-b]pyran $^1$H NMR (CDCl$_3$): 8.26 (brs, 1H), 7.23–7.14 (m, 6H), 7.10 (d, J=8.4 Hz, 1H), 6.72 (d, J=8.4 Hz, 1H), 6.66–6.65 (m, 1H), 4.82 (s, 1H), 4.69 (brs, 2H).

EXAMPLE 2H

2-Amino-3-cyano-7-amino-8-methyl-4-(3-bromo-4,5-dimethoxyphenyl)-4H-chromene $^1$H NMR (CDCl$_3$): 6.85 (d, J=1.6 Hz, 1H), 6.80 (d, J=1.6 Hz, 1H), 6.59 (d, J=8.5 Hz, 1H), 6.49 (d, J=8.4 Hz, 1H), 4.55 (s, 1H), 3.81 (s, 3H), 3.76 (s, 3H), 2.14 (s, 3H).

EXAMPLE 2I

2-Amino-3-cyano-7-hydroxy-8-amino-4-(3-bromo-4,5-dimethoxyphenyl)-4H-chromene $^1$H NMR (CD$_3$OD): 6.87 (d, J=1.8 Hz, 1H), 6.80 (d, J=1.8 Hz, 1H), 6.47 (d, J=8.4 Hz, 1H,), 6.20 (d, J=8.4 Hz, 1H), 4.56 (s, 1H), 3.79 (s, 3H), 3.75 (s, 3H).

EXAMPLE 2J

2-Amino-3-cyano-7-methoxy-4-(3,5-difluorophenyl)-4H-chromene $^1$H NMR (CDCl$_3$): 6.86 (d, J=8.6 Hz, 1H), 6.74–6.64 (m, 4H), 6.55 (d, J=2.3 Hz, 1H), 4.67 (s, 1H), 4.63 (brs, 2H), 3.86 (s, 3H).

EXAMPLE 2K

2-Amino-3-cyano-4-(3,5-difluorophenyl)-4H-indolo[4,5-b]pyran $^1$H NMR (Acetone-d$_6$): 7.38–7.37 (m, 1H), 7.19 (d, 1H), 6.96–6.91 (m, 2H), 6.86 (tt, J=2.3, 9.0 Hz, 1H), 6.79 (d, J=8.4 Hz, 1H), 6.56 (d, J=2.3 Hz, 1H), 6.33 (brs, 1H), 4.93 (s, 1H).

EXAMPLE 2L

2-Amino-3-cyano-4-(3-fluorophenyl)-4H-indolo[4,5-b]pyran $^1$H NMR (Acetone-d$_6$): 10.47 (brs, 1H), 7.37–7.32 (m, 2H), 7.17 (dd, J=1.0, 8.4 Hz, 1H), 7.12 (dt, J=1.2, 7.6 Hz, 1H), 7.04–6.94 (m, 2H), 6.76 (d, J=8.4 Hz, 1H), 6.58–6.56 (m, 1H), 6.26 (brs, 2H), 4.89 (s, 1H).

EXAMPLE 2M

2-Amino-3-cyano-7-amino-4-(3-fluorophenyl)-4H-chromene $^1$H NMR (Acetone-d$_6$): 7.38–7.32 (m, 1H), 7.08 (d, J=7.8 Hz, 1H), 6.99–6.95 (m, 2H), 6.73 (d, J=8.2 Hz, 1H), 6.41 (dd, J=2.3, 8.4 Hz, 1H), 6.35 (d, J=2.3 Hz, 1H), 6.10 (brs, 1H), 4.85 (dd, J=8.8 Hz, 1H), 4.64 (s, 1H).

EXAMPLE 2N

2-Amino-3-cyano-7-methoxy-4-(3-fluorophenyl)-4H-chromene $^1$H NMR (Acetone-d$_6$): 7.40–7.34 (m, 1H), 7.12–7.10 (m, 1H), 7.02–6.97 (m, 3H), 6.69 (dd, J=2.5, 8.6 Hz, 1H), 6.59 (d, J=2.5 Hz, 1H), 6.22 (brs, 1H), 4.77 (s, 1H), 3.79 (s, 3H).

EXAMPLE 2O

2-Amino-3-cyano-7-amino-4-(3,5-difluorophenyl)-4H-chromene $^1$H NMR (Acetone-d$_6$): 6.91–6.83 (m, 3H), 6.77 (d, J=8.4 Hz, 1H), 6.43 (dd, J=2.2, 8.3 Hz, 1H), 6.36 (d, J=2.2 Hz, 1H), 6.17 (brs, 1H), 4.89 (bd, J=7.6 Hz, 1H), 4.70 (s, 1H).

EXAMPLE 3

2-Amino-3-cyano-7-methoxy-4-(3,4,5-trimethoxyphenyl)-4H-chromene

The title compound was prepared from 3-methoxyphenol and 3,4,5-trimethoxybenzaldehyde by a procedure similar to that described in Example 2A in 7% yield. $^1$H NMR (CDCl$_3$): 6.90 (d, J=9.6 Hz, 1H), 6.64 (dd, J=2.7 Hz, 1H), 6.55 (d, J=2.4 Hz, 1H), 6.37 (s, 2H), 4.62 (s, 1H), 4.59 (s, 2H), 3.82–3.79 (m, 12H).

EXAMPLE 4

2-Amino-3-cyano-7-methoxy-4-(3-methoxyphenyl)-4H-chromene

The title compound was prepared from 3-methoxyphenol and 3-methoxybenzaldehyde by a procedure similar to that described in Example 2A in 12% yield. $^1$H NMR (CDCl$_3$): 7.21 (d, J=7.8 Hz, 1H), 6.89 (d, J=8.4 Hz, 1H), 6.80–6.75 (m, 2H), 6.72 (d, J=1.8 Hz, 1H), 6.61 (dd, J=2.4 Hz, 1H), 6.54 (d, J=2.4 Hz, 1H), 4.65 (s, 1H), 4.57 (s, 2H), 3.78 (s, 6H).

EXAMPLE 5

2-Amino-3-cyano-7-methoxy-4-(3-cyanophenyl)-4H-chromene

The title compound was prepared from 3-methoxyphenol and 3-cyanobenzaldehyde by a procedure similar to that described in Example 2A in 24% yield. $^1$H NMR (CDCl$_3$): 7.55–7.41 (m, 4H), 6.80 (d, J=8.7 Hz, 1H), 6.64 (dd, J=2.7 Hz, 1H), 6.58 (d, J=2.7 Hz, 1H), 4.74 (s, 1H), 4.68 (s, 2H), 3.80 (s, 3H).

EXAMPLE 6

2-Amino-3-cyano-7-methoxy-4-(3-bromophenyl)-4H-chromene

The title compound was prepared from 3-methoxyphenol and 3-bromobenzaldehyde by a procedure similar to that described in Example 2A in 27% yield. $^1$H NMR (CDCl$_3$): 7.39–7.35 (m, 1H), 7.29–7.28 (m, 1H), 7.22–7.14 (m, 2H), 6.85 (d, J=8.7 Hz, 1H), 6.63 (dd, J=2.7 Hz, 1H), 6.55 (d, J=2.7 Hz, 1H), 4.65 (s, 1H), 4.62 (s, 2H), 3.79 (s, 3H).

EXAMPLE 7

2-Amino-3-cyano-7-ethylamino-4-(3-bromophenyl)-4H-chromene

The title compound was prepared from 3-ethylaminophenol and 3-bromobenzaldehyde by a procedure similar to that described in Example 2A in 46% yield. $^1$H NMR (CDCl$_3$): 7.36–7.33 (m, 1H), 7.29–7.28 (m, 1H), 7.20–7.14 (m, 2H), 6.69 (d, J=8.7 Hz, 1H), 6.30 (dd, J=2.4 Hz, 1H), 6.20 (d, J=2.4 Hz, 1H), 4.59–4.57 (m, 3H), 3.67 (brs, 1H), 3.12 (q, J=7.2 Hz, 2H), 1.25 (t, J=7.2 Hz, 3H).

EXAMPLE 8

2-Amino-3-cyano-7-ethylamino-4-(3-chlorophenyl)-4H-chromene

The title compound was prepared from 3-ethylaminophenol and 3-chlorobenzaldehyde by a procedure similar to that described in Example 2A in 17% yield. $^1$H NMR (CDCl$_3$): 7.24–7.10 (m, 4H), 6.70 (d, J=8.4 Hz, 1H), 6.30 (dd, J=2.4 Hz, 1H), 6.20 (d, J=2.4 Hz, 1H), 4.60 (s, 1H), 4.56 (s, 2H), 3.67 (brs, 1H), 3.12 (q, J=6.9 Hz, 2H), 1.25 (t, J=7.2 Hz, 3H).

EXAMPLE 9

2-Amino-3-cyano-7-ethylamino-4-(3-nitrophenyl)-4H-chromene

The title compound was prepared from 3-ethylaminophenol and 3-nitrobenzaldehyde by a procedure similar to that described in Example 2A in 42% yield. $^1$H NMR (CDCl$_3$): 8.11–8.08 (m, 1H), 8.02 (s, 1H), 7.59 (d, J=7.5 Hz, 1H), 7.50 (t, J=7.8 Hz, 1H), 6.66 (d, J=8.4 Hz, 1H), 6.30 (dd, J=2.4 Hz, 1H), 6.22 (d, J=2.1 Hz, 1H), 4.77 (s, 1H), 4.64 (brs, 2H), 3.71 (brs, 1H), 3.13 (m, 2H), 1.25 (t, J=7.2 Hz, 3H).

EXAMPLE 10

2-Amino-3-cyano-7-methoxy-4-(3-chlorophenyl)-4H-chromene

The title compound was prepared from 3-methoxyphenol and 3-chlorobenzaldehyde by a procedure similar to that described in Example 2A in 15% yield. $^1$H NMR (CDCl$_3$): 7.28–7.19 (m, 2H), 7.13–7.10 (m, 2H), 6.85 (d, J=8.7 Hz, 1H), 6.63 (dd, J=2.4 Hz, 1H), 6.55 (d, J=2.7 Hz, 1H), 4.67 (s, 1H), 4.63 (brs, 2H), 3.79 (s, 3H).

EXAMPLE 11

2-Amino-3-cyano-7-methoxy-4-(3-nitrophenyl)-4H-chromene

The title compound was prepared from 3-methoxyphenol and 3-nitrobenzaldehyde by a procedure similar to that described in Example 2A in 18% yield. $^1$H NMR (CDCl$_3$): 8.13–8.10 (m, 1H), 8.02 (t, J=2.1 Hz, 1H), 7.60–7.57 (m, 1H), 7.51 (t, J=7.8 Hz, 1H), 6.82 (d, J=8.4 Hz, 1H), 6.64 (dd, J=2.4 Hz, 1H), 6.59 (d, J=2.4 Hz, 1H), 4.84 (s, 1H), 4.70 (brs, 2H), 3.80 (s, 3H).

EXAMPLE 12

2-Amino-3-cyano-7-methoxy-4-(3,5-dimethoxyphenyl)-4H-chromene

The title compound was prepared from 3-methoxyphenol and 3,5-dimethoxybenzaldehyde by a procedure similar to that described in Example 2A in 15% yield. $^1$H NMR (CDCl$_3$): 6.91 (d, J=9.0 Hz, 1H), 6.62 (dd, J=2.4 Hz, 1H), 6.53 (d, J=2.7 Hz, 1H), 6.33 (s, 3H), 4.60 (s, 1H), 4.57 (brs, 2H), 3.78–3.76 (m, 9H).

EXAMPLE 13

2-Amino-3-cyano-7-ethylamino-4-(3,4,5-trimethoxyphenyl)-4H-chromene

The title compound was prepared from 3-ethylaminophenol and 3,4,5-trimethoxybenzaldehyde by a procedure similar to that described in Example 2A in 79% yield. $^1$H NMR (CDCl$_3$): 6.75 (d, J=8.4 Hz, 1H), 6.39 (s, 2H), 6.32 (dd, J=2.4 Hz, 1H), 6.20 (d, J=2.4 Hz, 1H), 4.58–4.56 (m, 3H), 3.82–3.81 (m, 9H), 3.67 (brs, 1H), 3.12 (q, J=7.2 Hz, 2H), 1.25 (t, J=7.2 Hz, 3H).

EXAMPLE 14

2-Amino-3-cyano-7-ethylamino-4-(3,5-dimethoxyphenyl)-4H-chromene

The title compound was prepared from 3-ethylaminophenol and 3,5-dimethoxybenzaldehyde by a procedure similar to that described in Example 2A in 28% yield. $^1$H NMR (CDCl$_3$): 6.76 (d, J=8.4 Hz, 1H), 6.35–6.28 (m, 4H), 6.18 (d, J=2.7 Hz, 1H), 4.54–4.53 (m, 3H), 3.75 (s, 6H), 3.64 (brs, 1H), 3.11 (q, J=6.9 Hz, 2H), 1.24 (t, J=6.9 Hz, 3H).

EXAMPLE 15

2-Amino-3-cyano-7-ethylamino-4-(3-methoxyphenyl)-4H-chromene

The title compound was prepared from 3-ethylaminophenol and 3-methoxybenzaldehyde by a procedure similar to that described in Example 2A in 31% yield. $^1$H NMR (CDCl$_3$): 7.21 (t, J=7.8 Hz, 1H), 6.80–6.71 (m, 4H), 6.29 (dd, J=2.4 Hz, 1H), 6.19 (d, J=2.1 Hz, 1H), 4.59 (s, 1H), 4.54 (brs, 2H), 3.77 (s, 3H), 3.64 (brs, 1H), 3.11 (q, J=7.2 Hz, 2H), 1.24 (t, J=7.2 Hz, 3H).

EXAMPLE 16

2-Amino-3-cyano-7-ethylamino-4-(3-cyanophenyl)-4H-chromene

The title compound was prepared from 3-ethylaminophenol and 3-cyanobenzaldehyde by a procedure similar to that described in Example 2A in 15% yield. $^1$H NMR (CDCl$_3$): 7.53–7.39 (m, 4H), 6.64 (d, J=9.0 Hz, 1H), 6.31 (dd, J=2.1, 1H), 6.22 (d, J=2.1 Hz, 1H), 4.67–4.64 (m, 3H), 3.72 (brs, 1H), 3.13 (q, J=7.2 Hz, 2H), 1.26 (t, J=7.2 Hz, 3H).

EXAMPLE 17

2-Amino-3-cyano-7-methoxy-4-(3-pyridyl)-4H-chromene

The title compound was prepared from 3-methoxyphenol and 3-pyridinecarboxaldehyde by a procedure similar to that described in Example 2A in 15% yield. $^1$H NMR (DMSO-d$_6$): 8.48–8.44 (m, 2H), 7.54–7.51 (m, 1H), 7.37–7.33 (m, 1H), 7.03 (brs, 2H), 6.93 (d, J=8.7 Hz, 1H), 6.69 (d, J=8.7 Hz, 1H), 6.59 (s, 1H), 4.80 (s, 1H), 3.75–3.74 (m, 3H).

EXAMPLE 18

2-Amino-3-cyano-4-(3-pyridyl)-4H-indolo[4,5-b]pyran

The title compound was prepared from 4-hydroxyindole and 3-pyridinecarboxaldehyde by a procedure similar to that described in Example 2 in 10% yield. $^1$H NMR (DMSO-d$_6$): 11.32 (s, 1H), 8.49–8.41 (m, 2H), 7.53 (d, J=8.1 Hz, 1H), 7.37–7.30 (m, 2H), 7.11 (d, J=8.4 Hz, 1H), 7.01 (brs, 2H), 6.67 (d, J=8.4 Hz, 1H), 6.47 (s, 1H), 4.88 (s, 1H).

EXAMPLE 19

2,7-Diamino-3-cyano-4-(3-bromophenyl)-4H-chromene

The title compound was prepared from 3-aminophenol and 3-bromobenzaldehyde by a procedure similar to that described in Example 2A in 56% yield. $^1$H NMR (CDCl$_3$): 7.37–7.34 (m, 1H), 7.29–7.27 (m, 1H), 7.18–7.15 (m, 2H), 6.70 (d, J=8.7 Hz, 1H), 6.39 (dd, J=2.1 Hz, 1H), 6.31 (d, J=2.1 Hz, 1H), 4.59–4.57 (m, 3H), 3.74 (s, 2H).

EXAMPLE 20

2,7-Diamino-3-cyano-4-(3-cyanophenyl)-4H-chromene

The title compound was prepared from 3-aminophenol and 3-cyanobenzaldehyde by a procedure similar to that described in Example 2A in 44% yield. $^1$H NMR (CDCl$_3$): 7.54–7.40 (m, 4H), 6.66 (d, J=8.4 Hz, 1H), 6.39 (dd, J=2.4 Hz, 1H), 6.33 (d, J=2.4 Hz, 1H), 4.67–4.64 (m, 3H), 3.78 (s, 2H).

EXAMPLE 21

2,7-Diamino-3-cyano-4-(3-methoxyphenyl)-4H-chromene

The title compound was prepared from 3-aminophenol and 3-methoxybenzaldehyde by a procedure similar to that described in Example 2A in 71% yield. $^1$H NMR (CDCl$_3$): 7.22 (t, J=7.8 Hz, 1H), 6.80–6.71 (m, 4H), 6.39–6.35 (m, 1H), 6.30 (d, J=1.8 Hz, 1H), 4.59 (s, 1H), 4.53 (brs, 2H), 3.77 (s, 3H), 3.70 (s, 2H).

EXAMPLE 22

2,7-Diamino-3-cyano-4-(3-chlorophenyl)-4H-chromene

The title compound was prepared from 3-aminophenol and 3-chlorobenzaldehyde by a procedure similar to that described in Example 2A in 34% yield. $^1$H NMR (CDCl$_3$): 7.25–7.17 (m, 2H), 7.13–7.09 (m, 2H), 6.70 (d, J=8.1 Hz, 1H), 6.38 (dd, J=2.4 Hz, 1H), 6.31 (d, J=2.7 Hz, 1H), 4.60 (s, 1H), 4.58 (brs, 2H), 3.74 (s, 2H).

EXAMPLE 23

2,7-Diamino-3-cyano-4-(3-methylphenyl)-4H-chromene

The title compound was prepared from 3-aminophenol and 3-methyl-benzaldehyde by a procedure similar to that described in Example 2A in 40% yield. $^1$H NMR (CDCl$_3$): 7.18 (t, J=7.8 Hz, 1H), 7.04–6.97 (m, 3H), 6.73 (d, J=8.4 Hz, 1H), 6.37 (dd, J=2.1 Hz, 1H), 6.31 (d, J=2.4 Hz, 1H), 4.57 (s, 1H), 4.53 (brs, 2H), 3.70 (s, 2H), 2.31 (s, 3H).

EXAMPLE 24

2,7-Diamino-3-cyano-4-(3-pyridyl)-4H-chromene

The title compound was prepared from 3-aminophenol and 3-pyridinecarboxaldehyde by a procedure similar to that described in Example 2A in 44% yield. $^1$H NMR (CDCl$_3$): 8.50–8.48 (m, 2H), 7.51–7.48 (m, 1H), 7.25–7.22 (m, 1H), 6.69 (d, J=7.2 Hz, 1H), 6.36 (dd, J=2.4 Hz, 1H), 6.32 (d, J=2.4 Hz, 1H), 4.67 (s, 1H), 4.63 (brs, 2H), 3.76 (s, 2H).

EXAMPLE 25

2,7-Diamino-3-cyano-4-(3-nitrophenyl)-4H-chromene

The title compound was prepared from 3-aminophenol and 3-nitrobenzaldehyde by a procedure similar to that described in Example 2A in 44% yield. $^1$H NMR (CDCl$_3$): 8.12–8.09 (m, 1H), 8.02 (t, J=2.1 Hz, 1H), 7.60–7.47 (m, 2H), 6.67 (d, J=8.4 Hz, 1H), 6.40–6.39 (m, 2H), 4.77 (s, 1H), 4.66 (brs, 2H), 3.79 (s, 2H).

EXAMPLE 26

2-Amino-3-cyano-7-methoxy-4-phenyl-4H-chromene

The title compound was prepared from 3-methoxyphenol and benzaldehyde by a procedure similar to that described in Example 2A in 12% yield. $^1$H NMR (CDCl$_3$): 7.34–7.29 (m, 2H), 7.25–7.17 (m, 3H), 6.87 (d, J=8.7 Hz, 1H), 6.61 (dd, J=2.7 Hz, 1H), 6.55 (d, J=2.4 Hz, 1H), 4.68 (s, 1H), 4.57 (brs, 2H), 3.78 (s, 3H).

EXAMPLE 27

2-Amino-3-cyano-7-methoxy-4-(2,4-dimethoxypyrimidinyl)-4H-chromene

The title compound was prepared from 3-methoxyphenol and 5-formyl-2,4-dimethoxypyrimidine by a procedure similar to that described in Example 2A in 12% yield. $^1$H NMR (CDCl$_3$): 7.98 (s, 1H), 6.93 (d, J=8.4 Hz, 1H), 6.62 (d, J=8.7 Hz, 1H), 6.53 (d, J=2.7 Hz, 1H), 4.85 (s, 1H), 4.62 (brs, 2H), 3.96 (s, 6H), 3.78 (s, 3H).

EXAMPLE 28

2-Amino-3-cyano-7-methoxy-4-(1,2,3,6-tetrahydrophenyl)-4H-chromene

The title compound was prepared from 3-methoxyphenol and 1,2,3,6-tetrahydrobenzaldehyde by a procedure similar to that described in Example 2A in 2.5% yield. $^1$H NMR (CDCl$_3$): 7.05–7.01 (m, 1H), 6.71–6.67 (m, 1H), 6.51 (t, J=2.7 Hz, 1H), 5.60 (d, J=2.4 Hz, 2H), 4.85 (s, 1H), 4.58 (brs, 2H), 3.79 (s, 3H), 3.48 (dd, J=3.0 Hz, 1H), 2.05–1.57 (m, 6H), 1.45–1.26 (m, 1H).

EXAMPLE 29

2-Amino-3-cyano-4-phenyl-4-H-chromene

Method A
a) 3-Cyano-2-imino-4-phenyl-2H-chromene. To a mixture of 2-hydroxybenzophenone (2.0 g, 10 mmol) and malononitrile (661 mg, 10 mmol) in ethanol (15 mL) was added piperidine (0.5 mL, 5.0 mmol). The mixture was stirred under 0–5° C. for 2 h. The solvent was evaporated and the residue was purified by chromatography on silica gel with ethyl acetate and hexane (1:2) as eluant, yielding 1.2 g (8%) of the title compound. $^1$H NMR (CDCl$_3$): 7.74–7.29 (m, 7H), 7.20–7.13 (m, 2H).
b) 2-Amino-3-cyano-4-phenyl-4H-chromene. To a mixture of 3-cyano-2-imino-4-phenyl-2H-chromene (120 mg, 0.49 mmol) in methanol (15 mL) was added NaBH$_4$ (20 mg, 0.5 mmol) under 0–5° C. The mixture was stirred at room temperature overnight, then it was neutralized by aqueous 2N HCl. The solvent was evaporated and the residue was purified by chromatography on silica gel with ethyl acetate and hexane (1:2) as eluant, yielding 5 mg (29%) of the title compound. $^1$H NMR (CDCl$_3$): 7.35–7.18 (m, 6H), 7.06–6.96 (m, 3H), 4.75 (s, 1H), 4.61 (brs, 2H).

Method B
To a solution of t-butylnitrite (0.027 g, 0.26 mmol) in anhydrous DMF was added 2,7-diamino-3-cyano-4-phenyl-4H-chromene (53 mg, 0.201 mmol) in one portion. The reaction was immediately immersed into a 65° C. oil bath. Gas evolution occurred slowly. After stirring at 65° C. for 1.5 h, the reaction was quenched with addition of water (5 mL), and extracted with EtOAc (3×10 mL). The EtOAc extracts were washed with brine (2×5 mL), dried over MgSO4, and evaporated. The red residue was purified by chromatography on silica gel with EtOAc and hexane (1:2) as eluant to yield 6 mg (12%) of the title compound as a light yellow solid. $^1$H NMR (CD$_3$Cl, 300 MHz): 7.35–7.17 (m, 6H), 7.06–6.96 (m, 3H), 4.75 (s, 1H), 4.61 (brs, 2H).

EXAMPLE 30

2-Amino-3-cyano-7-methoxy-4-(5-methyl-3-pyridyl)-4H-chromene

To a solution of 5-methylpyridine-3-carbaldehyde (120 mg, 0.99 mmol) and 3-methoxyphenol (128 mg, 1.03 mmol) in anhydrous ethanol (10 mL) were added molanonitrile (68 mg, 1.03 mmol) and piperidine (0.1 mL, 1.01 mmol). After stirring at room temperature for 2.5 h, additional 3-methoxyphenol (128 mg, 1.03 mmol) was added. The mixture was stirred for 24 h. The solvent was evaporated and the residue was purified by chromatography on silica gel with EtOAc and hexane (from 1:4 to 1:1) as eluant. One fraction (151 mg) was collected as a mixture of the product and its imine isomer (2-imino-7-methoxy-4-(5-methyl-pyridin-3-yl)-chroman-3-carbonitrile). A portion of this mixture (25 mg, 0.085 mmol) and several drops of piperidine were refluxed in anhydrous ethanol (5 mL) for 18 h. The solvent was evaporated and the residue was purified by chromatography on silica gel with EtOAc and hexane (1:1) as eluant to yield 13 mg (52%) of the product as a yellow solid. $^1$H NMR (CDCl$_3$): 8.33 (d, J=1.8 Hz, 1H), 8.29 (d, J=1.8 Hz, 1H), 7.28 (t, J=1.8 Hz, 1H), 6.82 (dd, J=8.4, 0.6 Hz, 1H), 6.63 (dd, J=8.4, 2.7 Hz, 1H), 6.56 (d, J=2.7 Hz, 1H), 4.72 (brs, 2H), 4.69 (s, 1H), 3.79 (s, 3H), 2.30 (d, J=0.6 Hz, 3H).

EXAMPLE 31

2-Amino-3-cyano-7-ethylamino-4-(5-methyl-3-pyridyl)-4H-chromene

To a solution of 5-methyl-pyridine-3-carbaldehyde (60 mg, 0.5 mmol) and molanonitrile (33 mg, 0.5 mmol) in anhydrous ethanol (5 mL) was added piperidine (0.1 mL, 1.0 mmol). After stirring at room temperature for 2.5 h, 3-ethylamino-phenol (133 mg, 0.97 mmol) was added. The mixture was stirred for 18 h and then refluxed for 0.5 h. The solvent was evaporated. The residue was purified by chromatography on silica gel with EtOAc and hexane (1:1 and 2:1) as eluant to yield 59 mg (39%) of the product as a light yellow solid. $^1$H NMR (CDCl$_3$ with drops of CD$_3$OD): 8.25 (dd, J=2.1, 0.6 Hz, 1H), 8.23 (d=2.4 Hz, 1H), 7.29 (m, 1H), 6.65 (dd, J=2.7, 0.6 Hz, 1H), 6.29 (dd, J=8.1, 2.4 Hz, 1H), 6.20 (d, J=2.4 Hz, 1H), 4.86 (s, 2H), 4.61 (s, 1H), 3.10 (q, J=7.2 Hz, 2H), 2.28 (d, J=0.6 Hz, 3H), 1.23 (t, J=7.2 Hz, 3H).

EXAMPLE 32

2-Amino-3-cyano-4-(5-bromo-3-pyridyl)-7-ethylamino-4H-chromene

From 5-bromo-pyridine-3-carbaldehyde, molanonitrile and 3-ethylamino-phenol was obtained the title compound as a yellow solid. $^1$H NMR (CDCl$_3$): 8.54 (d, J=2.1 Hz, 1H), 8.42 (d, J=2.1 Hz, 1H), 7.60 (t, J=2.1 Hz, 1H), 6.66 (dd, J=8.4, 0.6 Hz, 1H), 6.32 (dd, J=8.4, 2.4 Hz, 1H), 6.21 (d, J=2.4 Hz, 1H), 4.70 (brs, 2H), 4.65 (s, 1H), 3.13 (q, J=14.3 Hz, 2H), 1.26 (t, J=7.2 Hz, 3H).

EXAMPLE 33

2-Amino-3-cyano-4-(5-bromo-3-pyridyl)-7-methoxy-4H-chromene

From 5-bromo-pyridine-3-carbaldehyde, molanonitrile and 3-methoxyphenol was obtained the title compound as a yellow solid. $^1$H NMR (CDCl$_3$): 8.57 (m, 1H), 8.43 (m, 1H), 7.60 (d, J=2.1 Hz, 1H), 6.83 (d, J=8.4 Hz, 1H), 6.66 (dd, J=8.4, 2.4 Hz, 1H), 6.58 (d, J=2.4 Hz, 1H), 4.75 (brs, 2H), 4.72 (s, 1H), 3.80 (s, 3H).

EXAMPLE 34

2,7-Diamino-3-cyano-4-(5-methyl-3-pyridyl)-4H-chromene

From 5-methyl-pyridine-3-carbaldehyde, molanonitrile and 3-aminophenol was obtained the title compound as a yellow solid. $^1$H NMR (CDCl$_3$ and drops of CD$_3$OD): 8.21 (m, 1H), 8.18 (m, 1H), 7.28 (m, 1H), 6.63 (d, J=8.4 Hz, 1H), 6.35 (dd, J=8.4, 2.4 Hz, 1H), 6.30 (d, J=2.4 Hz, 1H), 4.58 (s, 1H), 2.27 (s, 3H).

EXAMPLE 35

2-Amino-3-cyano-4-(5-methyl-3-pyridyl)-4H-indolo[4,5-b]pyran

From 5-methyl-pyridine-3-carbaldehyde, molanonitrile and 4-hydroxyindole was obtained 156 mg (52%) of the title compound as a yellow solid. $^1$H NMR (CD$_3$OD): 8.22 (m, 2H), 7.45 (m, 1H), 7.25 (d, J=3.0 Hz, 1H), 7.10 (dd, J=8.7, 0.9 Hz, 1H), 6.64 (d, J=8.7 Hz, 1H), 6.61 (dd, J=3.3, 0.9 Hz, 1H), 4.85 (s, 1H), 2.29 (s, 3H).

EXAMPLE 36

2-Amino-3-cyano-4-(5-bromo-3-pyridyl)-4H-indolo[4,5-b]pyran

To a solution of 5-bromo-pyridine-3-carbaldehyde (94 mg, 0.505 mmol) and molanonitrile (34 mg, 0.505 mmol) in anhydrous ethanol (2.5 mL) was added 4-hydroxyindole (70 mg, 0.526 mmol) and piperidine (0.1 mL, 1.0 mmol). After stirring at room temperature for 25 h, a light yellow solid (94 mg, 51%) was collected by filtration, washed with ether (5 mL) and dried in vacuo. $^1$H NMR (CDCl$_3$ and CD$_3$OD): 8.51 (d, J=1.8, 1H), 8.44 (d, J=2.1 Hz, 1H), 7.65 (t, J=1.8 Hz, 1H), 7.24 (d, J=3.3 Hz, 1H), 7.13 (d, J=8.7 Hz, 1H), 7.64 (m, 2H), 4.87 (s, 1H).

EXAMPLE 37

2,7-Diamino-3-cyano-4-(5-bromo-3-pyridyl)-4H-chromene

The title compound was prepared from of 5-bromo-pyridine-3-carbaldehyde, 3-aminophenol and molanonitrile by a procedure similar to that described in Example 36 in 44% yield. $^1$H NMR (CDCl$_3$ and drops of CD$_3$OD): 8.47 (d, J=2.1 Hz, 1H), 8.33 (d, J=1.8 Hz, 1H), 7.58 (t, J=2.0 Hz, 1H), 6.62 (d, J=8.4 Hz, 1H), 6.36 (dd, J=8.4, 2.1 Hz, 1H), 6.30 (d, J=2.1 Hz, 1H), 4.61 (s, 1H).

EXAMPLE 38

5-Methoxypyridine-3-carboxaldehyde a) 5-Bromo-3-methoxypyridine. To a stirred solution of 2,5-dibromopyridine (2.188 g, 9.2 mmol) in anhydrous MeOH (10 mL) was added NaOMe (10 mL of 25% NaOMe in MeOH, 42 mmol). The mixture was refluxed for 3 days and then poured into a stirred cold aqueous 5% NaHCO$_3$ (75 mL). The mixture was extracted with ether (4×10 mL) and the extracts were washed with brine (3×10 mL). The organic layer was dried (Na$_2$SO$_4$, anhydrous) and evaporated. The crude was purified by chromatography on silica gel with hexane: EtOAc (4:1~2:1) as eluant, yielding 1.02 g of (61%) the title compound. $^1$H NMR (CD$_3$OD): 8.17 (s, 1H), 8.12 (s, 1H), 7.24 (s, 1H), 3.74 (s, 3H).

b) 5-Methoxypyridine-3-carboxaldehyde. To a stirred solution of 5-bromo-3-methoxypyridine (0.815 g, 4.35 mmol) in THF (15 mL) at −78° C. was added n-BuLi (4.6 mmol). After 1 h, DMF (0.64 g, 8.20 mmol) was added and stirred continuously for 30 min at −78° C. The cold mixture was poured into a stirred aqueous solution of 5% NaHCO3 (25 mL) and extracted with ether (3×15 mL). The extract was evaporated and the crude was purified by chromatography on silica gel with hexane: EtOAc (4:1~2:1) as eluant, yielding 155 mg (0.26%) of the title compound. $^1$H NMR (CD$_3$OD): 9.88 (s, 1H), 8.44 (s, 1H), 8.32 (s, 1H), 3.70 (s, 3H).

EXAMPLE 39

2,7-Diamino-3-cyano-4-(5-methoxy-3-pyridyl)-4H-chromene

To a mixture of 5-methoxypyridine-3-carboxaldehyde (69.2 mg, 0.5 mmol) and malononitrile (34 mg, 0.5 mmol) in ethanol (2.5 mL) was added piperidine (0.1 mL, 1 mmol) and 3-aminophenol (60 mg, 0.55 mmol). The mixture was stirred for 2 h under argon at room temperature. The solvent was evaporated and the residue was purified by chromatography on silica gel with hexane: EtOAc (4:1~1:1) as eluant, yielding 44 mg of (31%) the title compound. $^1$H NMR (CD$_3$OD): 8.02 (s, 1H), 7.88 (s, 1H), 6.93 (s, 1H), 6.75 (s, 1H), 6.51 (d, J=8.4 Hz, 1H), 6.18 (d, J=8.4 Hz, 1H), 6.09 (s, 1H), 5.15 (br, 1H), 4.49 (s, 1H), 3.66 (s, 3H).

EXAMPLE 40

2-Amino-3-cyano-7-methoxy-4-(5-methoxy-pyridin-3-yl)-4H-chromene

From 5-methoxy-pyridine-3-carboxaldehyde, malononitrile and 3-methoxyphenol was obtained the title compound. $^1$H NMR (CD$_3$OD): 8.17 (s, 1H), 8.13 (s, 1H), 7.15 (s, 1H), 7.0 (d, J=8.7 Hz, 1H), 6.69 (d, J=8.7 Hz, 1H), 6.60 (s, 1H), 6.26 (s, 2H), 4.80 (s, 1H), 3.84 (s, 3H), 3.80 (s, 3H).

EXAMPLE 41

2-Amino-3-cyano-4-(5-methoxy-pyridin-3-yl)-4H-indolo[4,5-b]pyran

From 5-methoxy-pyridine-3-carboxaldehyde, malononitrile and 4-hydroxyindole was obtained the title compound. $^1$H NMR (acetone-d$_6$): 10.44 (br, 1H), 8.17 (d, J=1.8 Hz, 1H), 8.15 (d, J=2.7 Hz, 1H), 7.36 (t, J=2.7 Hz, 1H), 7.17 (m, 2H), 6.76 (d, J=8.1 Hz, 1H), 6.56 (s, 1H), 6.29 (s, 3H), 4.92 (s, 1H), 3.82 (s, 3H).

EXAMPLE 42

2-Amino-3-cyano-4-(3-bromo-4,5-dimethoxyphenyl)-4H-indolo[7,6-b]pyran

To a mixture of 5-bromoveratraldehyde (245 mg, 1 mmol) and malononitrile (66 mg, 1 mmol) in ethanol (4 mL) was added piperidine (0.05 mL, 0.5 mmol) and 7-hydroxyindole (133.2 mg, 1 mmol). The mixture was stirred at room temperature overnight. The solvent was evaporated and the residue was purified by chromatography on silica gel with EtOAc and hexane (1:2) as eluant, yielding 56 mg (13%) the title compound. $^1$H NMR (CDCl$_3$): 8.39 (brs, 1H), 7.34–7.25 (m, 2H), 6.91 (d, J=2.1 Hz, 1H), 6.76 (d, J=2.1 Hz, 1H), 6.67 (d, J=8.1 Hz, 1H), 6.56 (q, J=2.1 Hz, 1H), 4.80 (s, 1H), 4.67 (brs, 2H), 3.84 (s, 3H), 3.83 (s, 3H).

EXAMPLE 43

2-Amino-3-cyano-4-(3-methoxyphenyl)-4H-indolo[7,6-b]pyran

The title compound was prepared from 7-hydroxyindole and 3-methoxybenzaldehyde by a procedure similar to that described in Example 42 in 25% yield. $^1$H NMR (CDCl$_3$): 8.38 (brs, 1H), 7.31–7.19 (m, 3H), 6.84–6.68 (m, 4H), 6.53 (q, J=2.1 Hz, 1H), 4.83 (s, 1H), 4.62 (brs, 2H), 3.76 (s, 3H).

EXAMPLE 44

3-Cyano-2,7,8-triamino-4-(3-methoxyphenyl)-4H-chromene

To a mixture of m-anisaldehyde (544 mg, 4.0 mmol) and malononitrile (264 mg, 4.0 mmol) in ethanol (10 mL) was added piperidine (0.4 mL) and 2,3-diaminophenol (496 mg, 4.0 mmol). The mixture was stirred at room temperature under argon for 2 h, then it was diluted with water (20 mL). The precipitate was filtered to yield 1.08 g (88%) of the title compound as a brown solid. $^1$H NMR (CD$_3$OD): 8.02 (s, 1H), 7.05 (t, J=7.8 Hz, 1H), 6.58–6.66 (m, 3H), 6.30 (d, J=7.8 Hz, 1H), 6.08 (d, J=7.8 Hz, 1H), 4.41 (s, 1H), 3.60 (s, 3H).

EXAMPLE 45

3-Cyano-2,7,8-triamino-4-(3-bromo-4,5-dimethoxyphenyl)-4H-chromene

To a mixture of 5-bromoveratraldehyde (980 mg, 4.0 mmol) and malononitrile (246 mg, 4.0 mmol) in ethanol (10 mL) was added piperidine (0.4 mL) and 2,3-diaminophenol (496 mg, 4.0 mmol). The mixture was stirred at room temperature under argon for 2 h then diluted with water (20 mL). The precipitate was filtered to yield brown solid, yielding 1.367 g (85%) of the title compound. $^1$H NMR (CD$_3$OD): 6.25 (s, 1H), 6.18 25 (s, 1H), 6.34 (d, J=7.8, 1H), 6.10 (d, J=7.8, 1H), 4.43 (s, 1H), 3.68 (s, 3H), 3.64 (s, 3H).

EXAMPLE 46

2-Amino-3-cyano-4-(3-methoxyphenyl)-4H-indolo[4,5-b]pyran

To a solution of 4-hydroxyindole (500 mg, 3.76 mmol), 3-methoxybenzaldehyde (511 mg, 3.76 mmol) and malononitrile (250 mg, 3.76 mmol) in ethanol (10 mL) was added piperidine (0.18 mL, 1.62 mmol). The solution was stirred at room temperature overnight and the solvent was removed in vacuo. The crude material was purified by flash column chromatography (3:1 hexane:ethyl acetate) to yield 300 mg (25%) of title compound as white solids. $^1$H NMR (CDCl$_3$): 8.26 (brs, 1H), 7.26–7.18 (m, 2H), 7.09–7.06 (m, 1H), 6.84–6.74 (m, 4H), 6.65–6.63 (m, 1H), 4.80 (s, 1H), 4.65 (brs, 2H), 3.76 (s, 3H).

EXAMPLE 47

2-Amino-6-chloro-3-cyano-7-methyl-4-phenyl-4H-chromene a) 7-Methyl-6-chloro-3-cyano-2-imino-4-phenyl-2H-chromene. To a mixture of 4-methyl-5-chloro-2-hydroxybenzophenone (500 mg, 2 mmol) and malononitrile (132 mg, 2 mmol) in ethanol (15 mL) was added piperidine (0.1 mL, 1.0 mmol). The mixture was refluxed for 2 h. The solvent was evaporated and the residue was purified by column chromatography on silica gel with ethyl acetate and hexane (1:2) as eluant, yielding 100 mg (17%) of the title compound.

b) 2-Amino-6-chloro-3-cyano-7-methyl-4-phenyl-4H-chromene. To a mixture of 7-methyl-6-chloro-3-cyano-2-imino-4-phenyl-2H-chromene (100 mg, 0.34 mmol) in methanol (5 mL) was added NaBH$_4$ (26 mg, 0.68 mmol) under 0–5° C. The mixture was stirred at room temperature for 2 h, the solvent was evaporated and the residue was dissolved in ethyl acetate. The organic layer was washed with saturated NH$_4$Cl aqueous and brine, and dried over Na$_2$SO$_4$. The solvent was removed in vacuo. The crude material was purified by column chromatography on silica gel with ethyl acetate and hexane (1:2) as eluant, yielding 3 mg (3%) of the title compound. $^1$H NMR (CDCl$_3$): 7.33–7.17 (m, 5H), 6.94–6.90 (d, J=11.4 Hz, 2H), 4.67 (s, 1H), 4.57 (brs, 2H), 2.32 (s, 3H).

EXAMPLE 48

2-Amino-4-(3-bromo-4-hydroxy-5-methoxyphenyl)-3-cyano-7-dimethylamino-4H-chromene a) 3-Bromo-4-hydroxy-5-methoxybenzylidene: To a mixture of 3-bromo-4-hydroxy-5-methoxybenzaldehyde (2.31 g, 10 mmol) and malononitrile (660 mg, 10 mmol) in 20 mL of ethanol was added piperidine (0.5 mL, 0.5 mmol). The solution was stirred at room temperature overnight and precipitates were observed. The precipitates were collected by filtration and dried to yield 2.14 g (77%) of title compound as red solids.

b) 2-Amino-4-(3-bromo-4-hydroxy-5-methoxyphenyl)-3-cyano-7-dimethylamino-4H-chromene: To a mixture of 3-bromo-4-hydroxy-5-methoxybenzylidene (279 mg, 1 mmol) and 3-dimethylaminophenol (137 mg, 1 mmol) in 10 mL of ethanol was added piperidine (0.05 mL, 0.5 mmol) and the solution was refluxed overnight. The solvent was removed in vacuo. The crude material was purified by column chromatography (2:1 hexane:ethyl acetate) to yield 35 mg (8.4%) of the title compound. $^1$H NMR (CDCl$_3$): 6.88 (d, J=2.1 Hz, 1H), 6.78 (d, J=8.7 Hz, 1H), 6.67 (d, J=2.1 Hz, 1H), 6.44 (dd, J=2.4, 8.7 Hz, 1H), 6.28 (d, J=2.4 Hz, 1H), 5.81 (s, 1H), 4.55 (brs, 3H), 3.87 (s, 3H), 2.94 (s, 6H).

EXAMPLE 49

3-Cyano-4-(3-bromo-4-hydroxy-5-methoxyphenyl)-2,7-diamino-4H-chromene

To a mixture of 3-bromo-4-hydroxy-5-methoxybenzylidene (279 mg, 1 mmol) and 3-aminophenol (109 mg, 1 mmol) in 10 mL of ethanol was added piperidine (0.05 mL, 0.5 mmol) and the solution was refluxed overnight. The solvent was removed in vacuo. The crude material was purified by column chromatography (2:1 hexane:ethyl acetate) to yield 36 mg (9.3%) of the title compound. $^1$H NMR (DMSO-d$_6$): 6.80–6.76 (m, 3H), 6.67 (d, J=8.4 Hz, 1H), 6.28 (dd, J=2.1, 8.4 Hz, 1H), 6.19 (d, J=2.4 Hz, 1H), 5.24 (brs, 2H), 4.47 (s, 1H), 3.78 (s, 3H).

EXAMPLE 50

2-Amino-4-(3-bromo-4-hydroxy-5-methoxyphenyl)-3-cyano-4H-indolo[4,5-b]pyran

The title compound was prepared from 4-hydroxyindole and 3-bromo-4-hydroxy-5-methoxybenzylidene by a procedure similar to that described in Example 49 in 2.7% yield. $^1$H NMR (CDCl$_3$): 8.27 (brs, 1H), 7.31–7.27 (m, 1H), 7.12–7.10 (m, 1H), 6.91 (d, J=2.1 Hz, 1H), 6.75–6.70 (m, 2H), 6.65 (s, 1H), 5.82 (s, 1H), 4.76 (s, 1H), 4.68 (brs, 2H), 3.86 (s, 3H).

EXAMPLE 51

2-Amino-4-(3-bromo-4-hydroxy-5-methoxyphenyl)-3-cyano-4H-indolo[7,6-b]pyran

The title compound was prepared from 7-hydroxyindole and 3-bromo-4-hydroxy-5-methoxybenzylidene by a procedure similar to that described in Example 49 in 5.3% yield. $^1$H NMR (CDCl$_3$): 8.39 (brs, 1H), 7.31 (d, J=8.7 Hz, 1H), 7.26–7.25 (m, 1H), 6.90 (d, J=2.1 Hz, 1H), 6.71–6.65 (m, 2H), 6.56–6.54 (m, 1H), 5.84 (s, 1H), 4.78 (s, 1H), 4.66 (brs, 2H), 3.87 (s, 3H).

EXAMPLE 52

2-Amino-3-cyano-4-(3,5-dimethoxyphenyl)-4H-indolo[7,6-b]pyran

The title compound was prepared from 7-hydroxyindole and 3,5-dimethoxybenzylidene by a procedure similar to that described in Example 46 in 23% yield. $^1$H NMR (CDCl$_3$): 8.39 (brs, 1H), 7.30 (d, J=8.1 Hz, 1H), 7.23–7.21 (m, 1H), 6.71 (d, J=8.4 Hz, 1H), 6.54–6.52 (m, 1H), 6.38 (d, J=2.1 Hz, 2H), 6.34–6.32 (m, 1H), 4.78 (s, 1H), 4.63 (brs, 2H), 3.75 (s, 6H).

EXAMPLE 53

2-Amino-3-cyano-4-(3-cyano-phenyl)-4H-indolo[7,6-b]pyran

The title compound was prepared from 7-hydroxyindole and 3-cyanobenzaldehyde by a procedure similar to that described in Example 46 in 35% yield. $^1$H NMR (CDCl$_3$): 8.43 (brs, 1H), 7.55–7.51 (m, 2H), 7.47–7.40 (m, 2H), 7.33 (dd, J=0.9, 8.1 Hz, 1H), 7.28–7.25 (m, 1H), 6.61–6.55 (m, 2H), 4.92 (s, 1H), 4.73 (brs, 2H).

EXAMPLE 54

2-Amino-3-cyano-4-(3-trifluromethyl-phenyl)-4H-indolo[7,6-b]pyran

The title compound was prepared from 7-hydroxyindole and 3-trifluromethyl-benzaldehyde by a procedure similar to that described in Example 46 in 26% yield. $^1$H NMR (CDCl$_3$): 8.41 (brs, 1H), 7.51–7.42 (m, 4H), 7.31 (d, J=8.4 Hz, 1H), 7.27–7.25 (m, 1H), 6.62 (dd, J=0.6, 8.4 Hz, 1H), 6.56–6.54 (m, 1H), 4.95 (s, 1H), 4.71 (brs, 2H).

EXAMPLE 55

2-Amino-3-cyano-4-(5-methyl-pyridin-3-yl)-4H-indolo[7,6-b]pyran

The title compound was prepared from 7-hydroxyindole and 5-methylpyridine-3-carbaldehyde by a procedure similar to that described in Example 46 in 45% yield. $^1$H NMR (DMSO-d$_6$): 11.24 (brs, 1H), 8.30 (dd, J=2.1, 13.5 Hz, 2H), 7.36–7.35 (m, 2H), 7.23 (d, J=8.1 Hz, 1H), 6.79 (brs, 2H), 6.57 (d, J=8.4 Hz, 1H), 6.45–6.43 (m, 1H), 4.89 (s, 1H), 2.24 (s, 3H).

EXAMPLE 56

2-Amino-3-cyano-4-phenyl-4H-indolo[4,5-b]pyran

The title compound was prepared from 4-hydroxyindole and benzaldehyde by a procedure similar to that described in Example 46 in 42% yield. $^1$H NMR (DMSO-d$_6$): 11.30 (brs, 1H), 7.37–7.08 (m, 7H), 6.90 (brs, 2H), 6.67 (d, J=8.1 Hz, 1H), 6.46 (s, 1H), 4.77 (s, 1H).

EXAMPLE 57

2-Amino-3-cyano-4-(5-cyano-pyridin-3-yl)-4H-indolo[4,5-b]pyran

To a clear solution of 5-formyl-nicotinonitrile (0.0063 g, 0.048 mmol), ethanol (0.24 mL) and malononitrile (0.0031 g, 0.0048 mmol) was added 4-hydroxyindole (0.0064 g, 0.048 mmol) and piperidine (2.4 µL, 0.024 mmol). The resultant dark green solution was stirred at room temperature for 6 h, concentrated to a gray solid and extracted with EtOAc (30 mL). The organic layer was washed with water (5 mL), dried over MgSO$_4$, filtered through sintered glass and concentrated to yield 0.012 g (80%) of a green solid. Purification by column chromatography (elution with EtOAC:hexanes, 1:2) yielded 0.006 g (40%) of the above compound as a white solid. $^1$H-NMR (Acetone-d$_6$): 10.54 (s, 1H), 8.83 (t, J=2.20, 1.65 Hz, 2H), 8.09 (t, J=2.20, 1.92 Hz, 1H), 7.39 (t, J=2.75 Hz, 1H), 7.20 (dd, J=8.24, 0.82 Hz, 1H), 6.77 (dd, J=8.24 Hz, 1H), 6.58 (m, J=2.20, 1.92, 0.82 Hz, 1H), 6.42 (s, 2H), 5.09 (s, 1H).

EXAMPLE 58

2-Amino-3-cyano-4-(6-methyl-pyrazin-2-yl)-4H-indolo[4,5-b]pyran

The title compound was prepared from 6-methyl-pyrazine-2-carbaldehyde, malononitrile and 4-hydroxyindole by a procedure similar to Example 57 in 22% yield. $^1$-NMR (DMSO-$d_6$): 11.30 (brs, 1H), 8.44 (dd, J=15.6, 1.10 Hz, 2H), 7.36 (dd, J=3.03, 0.83 Hz, 1H), 7.09 (d, J=8.51 Hz, 1H), 7.00 (s, 2H), 6.69 (d, J=8.24 Hz, 1H), 6.45 (m, J=3.03, 1.10, 0.83 Hz, 1H), 4.97 (s, 1H), 2.44 (s, 3H).

EXAMPLE 59

2-Amino-3-cyano-4-(quinoxalin-2-yl)-4H-indolo[4,5-b]pyran

The title compound was prepared from quinoxaline-2-carbaldehyde, malononitrile and 4-hydroxyindole by a procedure similar to Example 57 in 79% yield. $^1$H-NMR (Acetone-$d_6$): 10.54 (brs, 1H), 8.86 (s, 1H), 8.07 (m, 2H), 7.86 (m, 3H), 7.39 (t, J=2.74, 5.49 Hz, 1H), 7.17 (dd, J=8.51, 0.82 Hz, 1H), 6.81 (dd, J=8.51 Hz, 1H), 6.61 (m, 1H), 6.51 (s, 2H), 5.25 (s, 1H).

EXAMPLE 60

2-Amino-3-cyano-4-(5-cyano-pyridin-3-yl)-4H-indolo[7,6-b]pyran

The title compound was prepared from 5-formyl-nicotinonitrile, malononitrile and 7-hydroxyindole by a procedure similar to Example 57 in 59% yield. $^1$H-NMR (Acetone-$d_6$): 10.54 (brs, 1H), 8.84 (m, J=2.20, 1.90 Hz, 2H), 8.12 (t, J=2.20, 1.90 Hz, 1H), 7.39 (m, J=3.03 Hz, 1H), 7.32 (dd, J=8.00 Hz, 1H), 6.68 (dd, J=8.20 Hz, 1H), 6.51 (m, J=3.03 Hz, 1H), 6.22 (s, 2H), 5.13 (s, 1H).

EXAMPLE 61

2-Amino-3-cyano-4-(6-methyl-pyrazin-2-yl)-4H-indolo[7,6-b]pyran

The title compound was prepared from 6-methyl-pyrazine-2-carbaldehyde, malononitrile and 7-hydroxyindole by a procedure similar to Example 57 in 82% yield. $^1$H-NMR (DMSO-$d_6$): 10.43 (brs, 1H), 8.50 (d, J=1.37 Hz, 1H), 8.38 (d, J=0.82 Hz, 1H), 7.35 (m, J=2.47, 2.20, 1.10, 0.83 Hz, 1H), 7.27 (d, J=8.24 Hz, 1H), 6.72 (dd, J=8.24, 0.55 Hz, 1H), 6.47 (m, J=2.20, 0.55 Hz, 1H), 6.11 (brs, 2H), 5.05 (s, 1H), 2.47 (s, 3H).

EXAMPLE 62

2-Amino-7-bromo-4-(3-bromo-4,5-dimethoxy-phenyl)-3-cyano-4H-chromene a) 7-Amino-4-(3-bromo-4,5-dimethoxy-phenyl)-3-cyano-2-imino-2H-chromene: To a suspension of 4-(3-bromo-4,5-dimethoxy-phenyl)-3-cyano-2,7-diamino-4H-chromene (1.002 g, 2.49 mmol) and molecular sieves (4 Å) (1.0 g) in anhydrous $CH_2Cl_2$ (50 mL) was added 2,3-dichloro-5,6-dicyano-1,4-benzoquinone (DDQ, 0.601 g, 2.64 mmol) and the reaction mixture was stirred at room temperature for 1.5 h. The reaction mixture was diluted with EtOAc (500 mL), washed with saturated $NaHCO_3$ (250 mL), brine (50 mL), dried over $MgSO_4$, and evaporated to yield 0.978 g (98%) of the product as a yellow solid. $^1$H NMR (DMSO-$d_6$): 8.36 (brs, 1H), 7.28 (dd, J=2.4, 9.3 Hz, 1H), 7.20 (d, J=1.8 Hz, 1H), 6.79 (d, J=8.7 Hz, 1H), 6.63 (brs, 2H), 6.41 (dd, J=1.8, 8.4 Hz, 1H), 6.33 (d, J=2.1 Hz, 1H), 3.86 (s, 3H), 3.83 (d, J=0.3 Hz, 3H).

b) 7-Bromo-4-(3-bromo-4,5-dimethoxy-phenyl)-3-cyano-2-imino-2H-chromene: To a suspension of t-butyl-nitrite (34 mg, 0.33 mmol), $CuBr_2$ (68 mg, 0.30 mmol) in anhydrous acetonitrile (1.5 mL) at 0° C. was added 7-amino-3-cyano-2-imino-4-(3-bromo-4,5-dimethoxy-phenyl)-2H-chromene (100 mg, 0.25 mmol). The mixture was stirred at 0° C. for 4 h, then was diluted with EtOAc (50 mL), washed with saturated $NaHCO_3$ (25 mL), brine (10 mL), dried over $MgSO_4$, and evaporated to yield a yellow solid. The crude was purified by column chromatography (silica gel, EtOAc:hexanes, 1:2 to 1:1) to yield 50 mg (43%) of the title compound as a yellow solid. $^1$H NMR (CDCl$_3$): 7.82 (brs, 1H), 7.38 (m, 1H), 7.30 (dd, J=2.1, 8.7 Hz, 1H), 7.18 (d, J=2.1 Hz, 1H), 7.09 (d, J=9.0 Hz, 1H), 6.93 (m, 1H), 3.96 (s, 3H), 3.92 (s, 3H).

c) 2-Amino-7-bromo-4-(3-bromo-4,5-dimethoxy-phenyl)-3-cyano-4H-chromene: To a solution of 7-bromo-4-(3-bromo-4,5-dimethoxy-phenyl)-3-cyano-2-imino-2H-chromene (50 mg, 0.108 mmol) in anhydrous THF (5 mL) was added $NaBH_4$ (8 mg, 0.216 mmol). The reaction mixture was stirred at room temperature for 4 h, and the solvent was evaporated. The residue was taken up by water (10 mL), and extracted with EtOAc (2×25 mL). The EtOAc extracts were washed with brine (10 mL), dried over $MgSO_4$, evaporated to yield a white solid. The crude was purified by column chromatography (silica gel, EtOAc:hexanes, 1:2) to yield 34 mg (68%) an off-white solid. $^1$H NMR (CDCl$_3$) 7.21–7.18 (m, 2H), 6.88–6.84 (m, 2H), 6.69 (d, J=2.1 Hz, 1H), 4.67 (brs, 2H), 4.62 (s, 1H), 3.84 (s, 3H), 3.83 (s, 3H).

EXAMPLE 63

2-Amino-4-(3-bromo-4,5-dimethoxy-phenyl)-7-chloro-3-cyano-4H-chromene a) 4-(3-bromo-4,5-dimethoxy-phenyl)-7-chloro-3-cyano-2-imino-2H-chromene: The title compound was prepared from 7-amino-4-(3-bromo-4,5-dimethoxy-phenyl)-3-cyano-2-imino-2H-chromene (82 mg, 0.205 mmol), t-butyl-nitrite (0.8 mL, 6 mmol) and $CuCl_2$ (104 mg, 0.774 mmol) by a procedure similar to Example 62b and isolated as a yellow solid (16 mg). $^1$H NMR (CDCl$_3$): 7.82 (s, 1H), 7.22–7.16 (m, 4H), 6.94 (d, J=1.8 Hz, 1H), 3.96 (s, 3H), 3.92 (s, 3H).

b) 2-Amino-4-(3-bromo-4,5-dimethoxy-phenyl)-7-chloro-3-cyano-4H-chromene: The title compound was prepared from 4-(3-bromo-4,5-dimethoxy-phenyl)-7-chloro-3-cyano-2-imino-2H-chromene by a procedure similar to Example 62c in 66% yield. $^1$H NMR (CDCl$_3$): 7.07–7.04 (m, 2H), 6.92 (dd, J=0.9, 9.0 Hz, 1H), 6.88 (d, J=1.8 Hz, 1H), 6.69 (d, J=1.8 Hz, 1H), 4.70 (brs, 2H), 4.63 (s, 1H), 3.84 (s, 3H), 3.84 (s, 3H).

EXAMPLE 64

2-Amino-3-cyano-4-(3-bromo-4,5-dimethoxy-phenyl)-4H-imidazo[4,5-h]chromene

To a mixture of 2,7,8-triamino-3-cyano-4-(3-bromo-4,5-dimethoxyphenyl)-4H-chromene (0.16 mg, 0.4 mmol), 1-(3-dimethylaminopropyl)-3-ethylcarbodiimide hydrochloride (76.7 mg, 0.4 mmol) and 1-hydroxybenzotriazole hydrate (48.9 mg, 0.4 mmol) in DMF (6 mL) was added formic acid (18.5 mg, 0.4 mmol) at room temperature under argon, and the mixture was stirred overnight. The mixture was stirred at 110° C. under argon for 24 h. The solvent was evaporated under high vacuum. The residue was purified by chromatography on silica gel with hexane:EtOAc (8:2~5:5) as eluant, yielding 61.5 mg (36%) of the title compound. $^1$H NMR (CD$_3$OD): 8.03 (s, 1H), 7.34 (d, J=9.9, 1H), 6.93 (m, 1H), 6.84 (d, J=9.9 Hz, 1H), 6.75 (s, 1H).

EXAMPLE 65

2-Amino-3-cyano-4-(3-bromo-4,5-dimethoxy-phenyl)-8-methyl-4H-imidazo[4,5-h]-chromene To a mixture of 2,7,8-triamino-3-cyano-4-(3-bromo-4,5-dimethoxy-phenyl)-4H-chromene (160 mg, 0.4 mmol) in 3 mL THF was added acetic chloride (37.7 mg, 0.48 mmol) dropwise at 0° C. under argon, and the mixture was stirred for 1 h. The temperature was increased to 50° C. and the mixture was stirred for 5 h. The solvent was evaporated under high vacuum. The residue was purified by chromatography on silica gel with hexane:EtOAc (2:1) as eluant, yielding 109 mg (62%) of the title compound. $^1$H NMR (Acetone-d$_6$): 8.75 (s, 1H), 7.03 (s, 1H), 6.98 (s, 1H), 6.94 (d, J=8.1 Hz, 1H), 6.38 (d, J=8.1, 1H), 4.71 (s, 1H), 3.87 (s, 3H), 3.76 (s, 3H), 2.10 (s, 3H).

EXAMPLE 66A

2-Amino-3-cyano-7-pyrrolidine-4-(3-bromo-4,5-dimethoxyphenyl)-4H-chromene a) 1-(3-Methoxy-phenyl)-pyrrolidine. Bromoanisole (63 μL), pyrrolidine (50 μL), sodium t-butoxyde (67 mg), tris(dibenzylidene-acetone)dipalladium (1.1 mg) and R(+)-BINAP (2.33 mg) were mixed in toluene (2.5 mL) one by one at −78° C. under nitrogen. Reaction mixture was allowed to warm to room temperature then heated to 80° C. overnight. The reaction was cooled, diluted with ether, filtered and evaporated. The compound was purified using bond elute silica gel column using 0 to 2% ethyl acetate/hexane as eluant to yield 70 mg (79%) of the desired compound. $^1$H NMR (CDCl$_3$): 7.14 (t, J=8.2 Hz, 1H), 6.26–6.20 (m, 2H), 6.12 (brs, 1H), 3.81 (s, 3H), 3.30–3.27 (m, 4H), 2.01–1.97 (m, 4H).

b) 3-Pyrrolidin-1-yl-phenol. 1-(3-methoxyphenyl)-pyrrolidine (70 mg) was treated with acetic acid (1.2 mL) and hydriodic acid 47% solution in water (1.2 mL) and heated to 120° C. for 3 h. The reaction mixture was allowed to cooled to room temperature and stand overnight. The next day the reaction mixture was stirred at 120° C. for 4 h, then cooled and poured slowly into sodium bicarbonate saturated solution. The reaction mixture was extracted with ethyl acetate, washed with brine, dried and concentrated to yield 3-pyrrolidin-1-yl-phenol (60 mg). $^1$H NMR (CDCl$_3$): 7.01 (t, J=8.13 Hz, 1H), 6.18–6.09 (m, 3H), 4.70 (brs, 1H), 3.24–3.20 (m, 4H), 1.98–1.90 (m, 4H).

c) 2-Amino-3-cyano-7-pyrrolidine-4-(3-bromo-4,5-dimethoxyphenyl)-4H-chromene. The titled compound was synthesized from 3-pyrrolidin-1-yl-phenol using a procedure similar to that described in Example 2A. $^1$H NMR (DMSO-d$_6$): 6.93 (d, J=2.0 Hz, 1H), 6.87 (brs, 2H), 6.83–6.80 (m, 2H), 6.28 (dd, J=2.4, 8.6 Hz, 1H), 6.04 (d, J=2.4 Hz, 1H), 4.56 (s, 1H), 3.78 (s, 3H), 3.68 (s, 3H), 3.16 (m, 4H), 1.92–1.89 (m, 4H).

The following two compounds were synthesized using a similar procedure as described in Example 66A.

EXAMPLE 66B

2-Amino-3-cyano-7-piperazine-4-(3-bromo-4,5-dimethoxyphenyl)-4H-chromene $^1$H NMR (CD$_3$OD): 6.89–6.83 (m, 3H), 6.71 (dd, J=2.5, 8.6 Hz, 1H), 6.60 (d, J=2.5 Hz, 1H), 4.60 (s, 1H), 3.81 (s, 3H), 3.76 (s, 3H), 3.34 (s, 2H), 3.15–3.13 (m, 4H), 2.97–2.95 (m, 4H).

EXAMPLE 66C

2-Amino-3-cyano-7-N-morpholine-4-(3-bromo-4,5-dimethoxyphenyl)-4H-chromene $^1$H NMR (CD$_3$OD): 6.95 (d, J=2.0 Hz, 1H), 6.93–6.90 (m, 3H), 6.83 (d, J=2.0 Hz, 1H), 6.69 (dd, J=2.4, 8.7 Hz, 1H), 6.45 (d, J=2.4 Hz, 1H), 4.64 (s, 1H), 3.79 (s, 3H), 3.69–3.67 (m, 7H), 3.07–3.05 (m, 4H).

EXAMPLE 67

2-Amino-3-cyano-7-pyrrole-4-(3-bromo-4,5-dimethoxyphenyl)-4H-chromene

2-Amino-3-cyano-7-amino-4-(3-bromo-4,5-dimethoxyphenyl)-4H-chromene (10 mg) was dissolved in 0.5 mL of toluene and treated with acetic acid (0.3 mL) followed by 2,5-dimethoxytetrafuran (5 μL). The reaction mixture was refluxed for 15 min, then cooled and neutralised with sodium bicarbonate saturated solution. The reaction mixture was extracted with dichloromethane, washed with brine, dried and concentrated. The residue was purified by bond elute silica gel chromatography using 10% to 30% ethyl acetate/hexane to yield 5.5 mg of the desired compound. $^1$H NMR (DMSO-d$_6$): 7.37 (t, J=2.2 Hz, 1H), 7.31 (dd, J=2.4, 8.4 Hz, 1H), 7.21 (d, J=2.4 Hz, 1H), 7.16 (d, J=8.8 Hz, 1H), 7.07 (brs, 2H), 7.01 (d, J=2.1 Hz, 1H), 6.91 (d, J=2.0 Hz, 1H), 6.24 (t, J=2.2 Hz, 1H), 4.78 (s, 1H), 3.80 (s, 3H), 3.69 (s, 3H).

EXAMPLE 68A

2-Amino-3-cyano-7-dimethylamino-4-(3-bromo-4,5-dimethoxyphenyl)-4-methylchromene a) 2-Imino-3-cyano-7-dimethylamino-4-(3-bromo-4,5-dimethoxyphenyl)-chromene: 4 Å Molecular sieves (20 mg) was added to 2-amino-3-cyano-4-(3-bromo-4,5-dimethoxyphenyl)-4H-chromene (20 mg, 0.05 mmol) in dichloromethane (1 mL). The solution was stirred for 15 min. Then 2,3-dichloro-5,6-dicyano-1,4-benzoquinone (10 mg, 0.05 mmol, 1 eq.) was added and stirred continuously at room temperature for 1 h. The reaction mixture was diluted with ethyl acetate (20 mL) and washed with sodium bicarbonate saturated solution (20 mL), brine (20 mL), dried over sodium sulfate and concentrated to yield 17 mg (79%) of the desired compound. $^1$H NMR (DMSO-d$_6$): 8.33 (s, 1H), 7.28 (d, J=1.9 Hz, 1H), 7.21 (d, J=1.9 Hz, 1H), 6.87 (d, J=9.1 Hz, 1H), 6.56 (dd, J=2.5, 9.1 Hz, 1H), 6.40 (d, J=2.5 Hz, 1H), 3.84 (s, 3H), 3.82 (s, 3H), 3.03 (s, 6H).

b) 2-Amino-3-cyano-7-dimethylamino-4-(3-bromo-4,5-dimethoxyphenyl)-4-methylchromene: Copper bromide dimethyl sulfide (71 mg, 0.35 mmol, 5 eq.) was suspended in dry tetrahydro-furan (1 mL) and cooled to −78° C. Methyl lithium 0.7 M in ether (1 mL, 0.7 mmol, 10 eq.) was added to the mixture at the same temperature and was stirred for 1 h. The imino chromene (30 mg, 0.07 mmol) was dissolved into a minimal amount of tetrahydrofuran and added to the reaction mixture. The orange solution was stirred 30 min at −78° C., then quenched with ammonium chloride saturated solution (10 mL), extracted with ethyl acetate (10 mL), washed with brine (10 mL), dried over sodium sulfate and concentrated. The residue was purified over a silica gel using 30% ethyl acetate/hexane. $^1$H NMR (acetone-$d_6$): 6.92–6.84 (m, 3H), 6.50 (dd, J=2.6, 8.9 Hz, 1H), 6.26 (d, J=2.6 Hz, 1H), 5.90 (brs, 1H), 3.76 (s, 3H), 3.73 (s, 3H), 2.91 (s, 6H), 2.05 (s, 3H).

The following compound was prepared using a similar procedure as described in Example 68A.

EXAMPLE 68B

2-Amino-3-cyano-4-phenyl-4-methylchromene $^1$H NMR (CDCl$_3$): 7.31–6.97 (m, 9H), 4.54 (brs, 2H), 1.95 (s, 3H).

EXAMPLE 69

2-Amino-3-cyano-4-(3-bromo-4-phosphoric acid-dipiperidine salt-5-methoxyphenyl)-4H-indolo[4,5-b]pyran a) Phosphoric acid 2-bromo-4-formyl-6-methoxy-phenyl ester bis-(2-cyanoethyl)ester: Anhydrous dichloromethane (2 mL) was cooled to 0° C. To this was added pyridine (0.64 mL, 7.92 mmol) and stirred for 5 min. Phosphorous oxychloride (0.246 mL, 2.64 mmol) was added slowly with stirring to the solution and left to stir for 15 min. 5-Bromovanillin (412 mg, 1.78 mmol) in anhydrous dichloromethane (4 mL) was then added to the reaction mixture and stirred for 1.75 h at room temperature whereupon TLC showed complete disappearance of starting material. Pyridine (0.64 mL, 7.92 mmol) was then added along with 3-hydroxyproprionitrile (0.54 mL, 7.92 mmol) and the stirring was pursue overnight. The mixture was diluted with dichloromethane and washed 4 times with water. The organic layer was dried over sodium sulfate, evaporated and the residue was purified by chromatography eluting with ethyl acetate to yield phosphoric acid 2-bromo-4-formyl-6-methoxy-phenyl ester bis-(2-cyanoethyl) ester (465 mg, 63%) as a colorless oil. $^1$H NMR (CDCl$_3$): 9.88 (s, 1H), 7.69 (dd, J=1.0, 1.9 Hz, 1H), 7.45 (d, J=1.8 Hz, 1H), 4.48–4.54 (m, 4H), 4.00 (s, 3H), 2.84–2.87 (m, 4H).

b) 2-Amino-3-cyano-4-(3-bromo-4-phosphoric acid cyanoethyl ester-monopiperidine salt-5-methoxyphenyl)-4H-indolo[4,5-b]pyran: To 4-hydroxyindole (148 mg, 1.11 mmol), malononitrile (74 mg, 1.11 mmol), and phosphoric acid 2-bromo-4-formyl-6-methoxy-phenyl ester bis-(2-cyanoethyl) ester (465 mg, 1.11 mmol) in dry ethanol was added piperidine (0.22 mL, 2.22 mmol). The reaction was stirred overnight at room temperature. The solvent was evaporated to yield a yellow foam which was purified by flash chromatography. The column was eluted with 20% ethyl acetate/hexanes to 5% methanol/dichloromethane to remove impurities. Eluting with 15%–20% methanol/dichloromethane gave the monocyanoethyl phosphate ester piperidine salt (557 mg, 84%) (containing 20% of the bis cyanoethyl phosphate ester by $^1$H NMR). $^1$H NMR (CD$_3$OD): 7.23 (d, J=3.1 Hz, 1H), 7.09 (dd, J=5.5, 7.3 Hz, 1H), 6.93 (d, J=2.0 Hz, 1H), 6.83 (d, J=1.8 Hz, 1H), 6.71 (d, J=8.4 Hz, 1H), 6.58 (dd, J=3.1, 7.3 Hz, 1H), 4.73 (s, 1H), 4.24 (m, 2H), 3.79 (s, 3H), 3.06 (m, 4H, (piperidine salt)), 2.82 (m, 2H), 1.6–1.8 (m, 6H, (piperidine salt)).

c) 2-Amino-3-cyano-4-(3-bromo-4-phosphoric acid-di piperidine salt-5-methoxyphenyl)-4H-indolo[4,5-b]pyran: To the monocyanoethyl phosphate ester piperidine salt (27 mg. 0.04 mmol) in dry ethanol (0.5 mL) was added piperidine (0.012 mL, 0.12 mmol). The reaction was heated for 7 h at 65° C. after which TLC showed complete disappearance of starting material. The solvent was evaporated to yield a brown residue. Upon adding methanol (2 mL) a solid precipitated from solution which was filtered and dried, proving to be the desired compound as the bis-piperidine salt (15.4 mg, 80%). $^1$H NMR (D$_2$O): 7.20 (d, J=3.2 Hz, 1H), 7.03 (d, J=8.3 Hz, 1H), 6.84 (d, J=1.8 Hz, 1H), 6.60 (m, 2H), 6.47 (d, J=3.1 Hz, 1H), 4.45 (s, 1H), 3.57 (s, 3H), 2.94 (m, 8H, (piperidine salt)), 1.4–1.6 (m, 12H, (piperidine salt)).

EXAMPLE 70

2-Amino-3-cyano-7-methoxy-4-(3-methoxyphenyl)-4H-thiochromene a) 2-Hydroxy-4-methoxyphenyl-(3'-methoxyphenyl)-methanone: To a solution of 3-methoxyphenol (500 μL, 4.55 mmol) in 5 mL of toluene anhydrous was added m-anisoyl chloride (640 μL, 4.55 mmol) at 0° C. followed by boron trichloride (4.55 mL of a 1.0 M solution in xylene, 4.55 mmol). The resultant mixture was warmed and stirred at 85° C. for 24 h. It was then diluted with 40 mL of ether, washed twice with 25 ml portion of saturated aqueous solution of sodium bicarbonate, dried with sodium sulfate, concentrated and purified by flash chromatography using 20% ethyl acetate/hexanes as eluant to yield 883 mg of the title compound as a colorless oil. $^1$H NMR (CDCl$_3$): 7.53 (d, J=8.9 Hz, 1H), 7.39 (dd, J=7.5, 0.5 Hz, 1H), 7.18–7.20 (m, 1H), 7.15–7.16 (m, 1H), 7.10 (ddd, J=8.3, 2.6, 1.0 Hz, 1H), 6.52 (d, J=2.5 Hz, 1H), 6.41 (dd, J=9.0, 2.6 Hz, 1H), 3.87 (s, 3H), 3.86 (s, 3H).

b) Dimethylthiocarbamic acid O-[5-methoxy-2-(3'-methoxybenzoyl)-phenyl]ester: A mixture of (2-hydroxy-4-methoxy-phenyl)-(3'-methoxy-phenyl)-methanone (872 mg, 3.38 mmol), dimethylthiocarbamoyl chloride (835 mg, 6.76 mmol) and 1,4-diazabicyclo[2.2.2]octane (758 mg, 6.76 mmol) in 10 mL of DMF anhydrous was stirred overnight at room temperature. A portion of 100 mL of ether was added and the resultant mixture was washed twice with a saturated solution of aqueous sodium bicarbonate, dried with sodium sulfate and concentrated. Purification by flash chromatography using 15% to 20% ethyl acetate/hexanes yielded 975 mg (83%) of dimethylthiocarbamic acid O-[5-methoxy-2-(3'-methoxybenzoyl)-phenyl]ester as a pale yellow oil. $^1$H NMR (CDCl$_3$): 7.51 (d, J=8.6 Hz, 1H), 7.33–7.35 (m, 2H), 7.08–7.11 (m, 1H), 6.83 (dd, J=8.6 and 2.5 Hz, 1H), 6.41 (d, J=2.4 Hz, 1H), 3.90 (s, 3H), 3.85 (s, 3H), 3.32 (s, 3H), 3.16 (s, 3H).

c) Dimethyl-thiocarbamic acid S-[5-methoxy-2-(3'-methoxybenzoyl)-phenyl]ester: Dimethylthiocarbamic acid O-[5-methoxy-2-(3'-methoxybenzoyl)-phenyl]ester (879 mg, 2.54 mmol) was stirred in 8 mL of N,N-dimethylaniline at 215° C. for 3 h. After cooling at room temperature, a portion of 100 mL of ether was added. The resultant mixture was washed twice with a 10% solution of hydrochloric acid, once with a saturated aqueous solution of sodium bicarbonate, dried with sodium sulfate and concentrated. The crude compound was purified by flash chromatography using 20% ethyl acetate/hexanes to yield 502 mg (57%) of dimethylthiocarbamic acid S-[5-methoxy-2-(3'-methoxy-benzoyl)-phenyl]ester as a pale yellow oil. $^1$H NMR (CDCl$_3$): 7.40 (d, J=8.5 Hz, 1H), 7.30–7.34 (m, 2H), 7.19 (d, J=2.6 Hz, 1H), 7.07–7.10 (m, 1H), 6.95–6.97 (m, 1H), 3.88 (s, 3H), 3.82 (s, 3H), 2.89 (s, 6H).

d) 2-Mercapto-4-methoxy-phenyl)-(3'-methoxy-phenyl)-methanone: A mixture of dimethylthiocarbamic acid S-[5-methoxy-2-(3'-methoxybenzoyl)-phenyl]ester (164 mg, 0.475 mmol) and potassium hydroxyde (200 mg, 3.56 mmol) was stirred in 2 mL of dry methanol at 70° C. for 1.5 h. After cooling at room temperature, the solvent was removed. The crude compound obtained was purified by chromatography using 20% ethyl acetate/hexanes to yield 35 mg (27%) of (2-mercapto-4-methoxyphenyl)-(3'-methoxyphenyl)-methanone as a pale yellow oil. $^1$H NMR (CDCl$_3$): 7.50 (d, J=8.8 Hz, 1H), 7.33–7.37 (m, 1H), 7.22–7.27 (m, 2H), 7.10 (ddd, J=8.2, 2.6 and 1.0 Hz, 1H), 6.90 (d, J= 2.5 Hz, 1H), 6.65 (dd, J=8.8 and 2.5 Hz, 1H), 4.76 (s, 1H), 3.85 (s, 3H), 3.84 (s, 3H).

e) 2-Imino-3-cyano-7-methoxy-4-(3'-phenyl)-2H-thiochromene: To a mixture of (2-mercapto-4-methoxyphenyl)-(3'-methoxyphenyl)-methanone (35 mg, 0.13 mmol) and malononitrile (8.5 mg, 0.13 mmol) in 200 µL of dry ethanol was added piperidine (7.0 µL, 0.06 mmol) at 0° C. The resultant mixture was stirred at 0° C. for 2.5 h. The solvent was evaporated and the residue was purified by flash chromatography (25% ethyl acetate/hexanes) to yield 31 mg (75%) of 2-imino-3-cyano-7-methoxy-4-(3'-methoxy-phenyl)-2H-thiochromene as an orange waxy oil. $^1$H NMR (CDCl$_3$): 9.31 (brs, 1H), 7.42–7.46 (m, 1H), 7.03–7.11 (m, 2H), 6.91 (d, J=7.8 Hz, 1H), 6.85–6.86 (m, 1H), 6.80 (brs, 1H), 6.68 (dd, J=9.1 and 2.6 Hz, 1H), 3.85 (s, 3H), 3.84 (s, 3H).

f) 2-Amino-3-cyano-4-phenyl-1,4-dihydroquinoline: A solution of 2-imino-3-cyano-7-methoxy-4-(3'-methoxy-phenyl)-2H-thiochromene (25 mg, 0.077 mmol) in 2.3 mL of dry methanol was treated with sodium borohydride (5.0 mg, 0.13 mmol) at 0° C. The resultant mixture was stirred overnight at room temperature. It was then neutralized with 3 drops of a 1 N solution of hydrochloric acid, dissolved in 20 mL of ether, washed twice with 10 mL of aqueous saturated bicarbonate and dried with sodium sulfate. The solvent was evaporated and the residue was purified by flash chromatography using 25% ethyl acetate/hexanes to yield 15.9 mg (63%) of 2-amino-3-cyano-7-methoxy-4-(3-methoxyphenyl)-4H-thiochromene as a pale yellow solid. $^1$H NMR (CDCl$_3$): 7.14–7.21 (m, 2H), 6.79–6.82 (m, 3H), 6.72–6.76 (m, 2H), 4.82 (s, 1H), 4.66 (brs, 2H), 3.79 (s, 3H), 3.75 (s, 3H).

EXAMPLE 71

2-Amino-3-cyano-4-phenyl-1,4-dihydroquinoline

Sodium cyanoborohydride (10 mg) was added to 2-amino-4-phenylquinoline-3-carbonitrile (5 mg) in solution in acetic acid (0.25 mL). After stirring 85 min at room temperature, there was no more change in TLC, so sodium cyanoborohydride (15 mg) was further added. The reaction mixture was allowed to stir for another 20 min, then was neutralized with saturated sodium bicarbonate solution and extracted with ethyl acetate. The extract was washed with saturated sodium chloride solution and dried. The crude obtained after removing the solvent was passed through a bond-elute (4:1 to 7:3 hexane-ethyl acetate) yielding 2 mg of 2-amino-3-cyano-4-phenyl-1,4-dihydroquinoline. $^1$H NMR (CD$_3$OD): 7.22–7.26 (m, 2H), 7.12–7.19 (m, 3H), 7.07 (dt, J=7.8, 1.6 Hz, 1H), 6.92 (finely split doublet, J=7.8 Hz, 1H), 6.82 (dt, J=7.6, 1.2 Hz, 1H), 6.77 (dd, J=8.1, 1.2 Hz, 1H), 4.76 (s, 1H).

EXAMPLE 72

2-Amino-3-ethoxycarboxyl-4-(3-bromo-4,5-dimethoxy-phenyl)-4H-indolo[4,5-b]pyran

To a solution of hydroxyindole (528 mg, 3.97 mmol, 1 eq.), bromoveratraldehyde (973 mg, 3.97 mmol, 1 eq.) and ethyl cyanoacetate (449 mg, 3.97 mmol, 1 eq.) in dry ethanol (20 mL), was added piperidine (0.78 µL, 7.94 mmol, 2 eq.). Reaction mixture was stirred at room temperature overnight. Solvent was evaporated and the crude compound was purified by flash chromatography using 20–50% ethyl acetate/hexane to yield a foamy solid. (354 mg, 19%). $^1$H NMR (DMSO-d$_6$): 7.64 (brs, 2H), 7.33 (m, 1H), 7.08 (dd, J=8.4, 0.9 Hz, 1H), 6.94 (d, J=1.9 Hz, 1H), 6.87 (d, J=8.4 Hz, 1H), 6.76 (d, J=1.9 Hz, 1H), 6.46 (m, 1H), 4.90 (s, 1H), 4.02–3.92 (m, 2H), 3.75 (s, 3H), 3.61 (s, 3H), 1.16–1.13 (t, J=7.2 Hz, 3H).

EXAMPLE 73

2-Amino-3-methoxylcarboxyl-4-(3-bromo-4,5-dimethoxy-4H-indolo[4,5-b]pyran

To a solution of hydroxyindole (138 mg, 1.04 mmol, 1 eq.), bromoveratraldehyde (254 mg, 1.04 mmol, 1 eq.) and methyl cyanoacetate (103 mg, 1.04 mmol, 1 eq.) in dry ethanol, was added piperidine (0.20 µL, 2.08 mmol, 2 eq.). The reaction mixture was stirred at room temperature overnight. The solvent was evaporated and the crude compound was purified by flash chromatography using 30% ethyl acetate/hexane to yield a pink solid (69 mg, 14%). $^1$H NMR (CD$_3$OD): 7.21 (m, 1H), 7.08 (dd, J=0.9, 8.4 Hz, 1H), 6.91 (d, J=1.8 Hz, 1H), 6.84–6.80 (m, 2H), 6.60–6.59 (dd, J=0.9, 3.1 Hz, 1H), 4.92 (s, 1H), 3.77 (s, 3H), 3.71 (s, 3H), 3.63 (s, 3H).

EXAMPLE 74

2-Amino-3-cyano-7-amino-8-hydroxy-4-(3-bromo-4,5-dimethoxyphenyl)-4H-chromene a) 2,3-Dihydroxyaniline: 2,3-dimethoxyaniline (500 mg, 3.26 mmol) was dissolved in acetic acid (10 mL). Hydriodic acid 47% solution in water (10 mL) was added and the reaction stirred under reflux 8 h. The reaction was cooled to room temperature and stirred for 3 days. Solvent was removed in vacuo and the yellow solid dissolved in water and neutralized with sodium bicarbonate saturated aqueous solution. The aqueous layer was extracted with ethyl acetate (4×20 mL). The organic layers were combined, washed with a 10% solution of sodium thiosulfate (30 mL), water (30 mL), brine (30 mL), dried over sodium sulfate, filtered and concentrated. The crude product was purified by Biotage (cartridge 40S, SiO$_2$) using 1, 2 and 4% methanol in dichloromethane to yield 188 mg (46%) of 2,3-dihydroxyaniline as a beige solid. $^1$H NMR (CD$_3$OD): 6.47 (t, J=8.0 Hz, 1H), 6.28 (dd, J=8.0, 1.6 Hz, 1H), 6.24 (dd, J=8.0, 1.6 Hz, 1H).

b) 2-Amino-3-cyano-7-amino-8-hydroxy-4-(3-bromo-4, 5-dimethoxyphenyl)-4H-chromene: 2,3-dihydroxyaniline (80 mg, 0.64 mmol), 5-bromoveratraldehyde (157 mg, 0.64 mmol) and malononitrile (42 mg, 0.64 mmol) were dissolved in ethanol (4 mL). Piperidine (127 μL, 1.28 mmol) was added and the reaction stirred at room temperature overnight. The reaction mixture was concentrated in vacuo and the desired product isolated by Biotage flash chromatography (cartridge 12M) eluting with 2 and 5% methanol in dichloromethane to yield 97 mg (36%) of the desired 2-amino-3-cyano-7-amino-8-hydroxy-4-(3-bromo-4,5-dimethoxyphenyl)-4H-chromene as a brown foamy solid. $^1$H NMR (CD$_3$OD): 6.86 (s, 1H), 6.80 (s, 1H), 6.47 (d, J=8.0 Hz, 1H), 6.29 (d, J=8.0 Hz, 1H), 4.56 (s, 1H), 3.78 (s, 3H), 3.75 (s, 3H).

EXAMPLE 75

2-Amino-4-(3-bromo-4,5-dimethoxyphenyl)-3-cyano-9-methyl-4H-imidazo[4,5-b]chromene a) 4-Hydroxy-3H-benzimidazole: A mixture of 2,3-diaminophenol (1.242 g, 10 mmol), triethyl orthformate (1.483 g, 10 mmol) and p-toluenesulfonic acid (95 mg, 0.5 mmol) was heated at 120° C. After 1 h, TLC showed consumption of the starting material and approximately 1 mL of ethyl alcohol was collected using Dean-Stock distillation head. The reaction mixture was then evaporated and dried further in vacuo to yield a mixture of 4-hydroxy-3H-benzimidazole and 4-hydroxy-1H-benzimidazole as a dark solid. $^1$H NMR (CDCl$_3$): 9.15 (brs, 1H), 8.28 (s, 1H), 7.11 (d, J=2.1 Hz, 1H), 7.10 (s, 1H), 6.72 (d, J=3.3 Hz, 1H) and 6.71 (d, J=3.3 Hz, 1H).

b) 2-Amino-4-(3-bromo-4,5-dimethoxyphenyl)-3-cyano-9-methyl-4H-imidazo[4,5-h]chromene: To a stirred solution of 5-bromoveratraldehyde (247 mg, 1.01 mmol) and 4-hydroxy-3H-benzimidazole and 4-hydroxy-1H-benzimidazole (139 mg, 1.03 mmol) from above in absolute ethanol (10 mL) was added malononitrile (68 mg, 1.03 mmol) and piperidine (0.1 mL). The reaction mixture was stirred at room temperature overnight. The solvent was evaporated under reduced pressure and the resultant residue was purified by column chromatography (silica gel, EtOAc:hexanes, 3:1 plus 5% MeOH and 1% Et$_3$N) to yield 169 mg (38%) mixture of 2-amino-4-(3-bromo-4,5-dimethoxyphenyl)-3-cyano-9H-4H-imidazo[4,5-h]chromene and 2-amino-4-(3-bromo-4,5-dimethoxyphenyl)-3-cyano-7H-4H-imidazo[4,5-h]chromene as an off-white solid. $^1$H NMR (acetone-d$_6$): 8.23 (s, 1H), 7.31 (d, J=8.1 Hz, 1H), 7.05 (d, J=1.8 Hz, 1H), 7.02 (d, J=2.1 Hz, 1H), 6.94 (d, J=8.4 Hz, 1H), 6.40 (brs, 2H), 4.88 (s, 1H), 3.85 (s, 3H), 3.76 (s, 3H).

The above mixture (52 mg, 0.12 mmol), iodomethane (10 uL, 0.16 mmol) and cesium carbonate (24 mg, 0.074 mmol) was stirred in acteone (2 mL) at room temperature for 42 h. The solvent was evaporated under reduced pressure and the residue was dissolved in EtOAc (50 mL). Water (0.5 mL) was added to dissolve insoluble inorganic salt. The mixture was then dried over MgSO$_4$ and evaporated to yield 48 mg of a light brown solid. The solid was purified by column chromatography (silica gel, EtOAc:hexanes, 3:1 plus 5% MeOH and 1% Et$_3$N) to yield 2-amino-4-(3-bromo-4,5-dimethoxyphenyl)-3-cyano-9-methyl-4H-imidazo[4,5-h]chromene as an off-white solid. $^1$H NMR (CDCl$_3$): 7.80 (s, 1H), 7.48 (d, J=8.4 Hz, 1H), 6.89 (d, J=2.1 Hz, 1H), 6.83 (d, J=8.4 Hz, 1H), 6.77 (d, J=2.1 Hz, 1H), 4.81 (s, 1H), 4.66 (brs, 2H), 4.12 (s, 3H), 3.86 (s, 3H), 3.84 (s, 3H).

A second fraction was obtained as 2-amino-4-(3-bromo-4,5-dimethoxyphenyl)-3-cyano-7-methyl-4H-imidazo[4,5-h]chromene. $^1$H NMR (CDCl$_3$): 7.88 (s, 1H), 7.11 (d, J=8.4 Hz, 1H), 6.92 (d, J=1.8 Hz, 1H), 6.90 (d, J=8.7 Hz, 1H), 6.72 (d, J=2.1 Hz, 1H), 4.84 (brs, 2H), 4.80 (s, 1H), 3.85 (s, 3H), 3.83 (s, 3H), 3.81 (s, 1H).

EXAMPLE 76

3-Cyano-4-(3-bromo-4,5-dimethoxyphenyl)-2-methylamino-9-methyl-4H-pyrrolo[3,2-h]chromene To a solution of 2-amino-4-(3-bromo-4,5-dimethoxyphenyl)-3-cyano-4H-pyrrolo[3,2-h]chromene (200 mg, 0.47 mmol) and methyl iodide (0.12 mL, 1.88 mmol) in acetone (5 mL) was added cesium carbonate (306.3 mg, 0.94 mmol). The mixture was stirred at room temperature overnight. The solid was removed by filtration. The filtrate was concentrated in vacuo and the crude material was purified by column chromatography (1:1 hexane/ethyl acetate) to yield 50 mg (24%) of the title compound as a white solid. $^1$H NMR (CDCl$_3$): 8.43 (brs, 1H), 7.59–7.48 (m, 2H), 7.31 (d, J=2.1 Hz, 1H), 7.26–7.22 (m, 2H), 6.58–6.56 (m, 1H), 4.91 (s, 1H), 3.88–3.85 (m, 9H), 1.8 (s, 3H).

EXAMPLE 77

2-Amino-4-(3-bromo-4,5-dimethoxyphenyl)-3-cyano-9-methyl-4H-pyrrolo[3,2-h]chromene a) 1-Methyl-indol-7-ol: A mixture of 7-benzyloxyindole (300 mg, 1.34 mmol), dimethyl oxalate (317 mg, 2.68 mmol) and potassium tert-butoxide (302 mg, 2.68 mmol) in 5 mL DMF was stirred at 110° C. overnight. The solution was poured into NaHCO$_3$ saturated solution (20 mL) and extracted with EtOAc. The organic layer was separated, washed with brine and dried over Na$_2$SO$_4$. The solvent was removed in vacuo to yield 200 mg of 7-benzyloxy-1-methylindole, which was hydrogenated by 5% Pd/C in 20 mL methanol under H$_2$ (50 psi) to yield 90 mg (45.5%) of the title compound. $^1$H NMR (CDCl$_3$): 7.19–7.16 (m, 1H), 6.94 (d, J=3 Hz, 1H), 6.86 (t, J=7.5 Hz, 1H), 6.48–6.46 (m, 1H), 6.40 (d, J=3 Hz, 1H), 5.05 (s, 1H), 4.07 (s, 3H).

b) 2-Amino-4-(3-bromo-4,5-dimethoxyphenyl)-3-cyano-9-methyl-4H-pyrrolo[3,2-h]chromene: The title compound was prepared from 1-methylindol-7-ol (90 mg, 0.61 mmol), 5-bromoveratraldehyde (150 mg, 0.61 mmol), malononitrile (41 mg, 0.61 mmol) and piperidine (0.05 mL, 0.31 mmol to yield 140 mg (52%) of a white solid. $^1$H NMR (CDCl$_3$): 7.27 (d, J=8.4 Hz, 1H), 6.99 (d, J=3.3 Hz, 1H), 6.90 (d, J=1.8 Hz, 1H), 6.77 (d, J=2.4 Hz, 1H), 6.61 (d, J=8.1 Hz, 1H), 6.42 (d, J=3.0 Hz, 1H), 4.79 (s, 1H), 4.62 (brs, 2H), 4.09 (s, 3H), 3.85 (s, 3H), 3.83 (s, 3H).

EXAMPLE 78

2-Amino-3-cyano-4-(3-methoxyphenyl)-4H-pyrazino[2,3-h]chromene

To a mixture of 2,7,8-triamino-3-cyano-4-(3-methoxyphenyl)-4H-chromene (0.124 g, 0.4 mmol) in 3 mL THF was added glyoxal (0.06 mL, 40% in H$_2$O, 0.4 mmol). The mixture was stirred at room temperature under argon for 3 h, then refluxed for 3 h. The solvent was evaporated under high vacuum. The residue was purified by chromatography on silica gel with hexane: EtOAc (8:2~5:5) as eluant, yielding 0.021 g (16%) of the title compound. $^1$H NMR (CD$_3$OD): 8.90 (m, 2H), 7.79 (d, J=9.0 Hz, 1H), 7.36 (d, J=9.0 Hz, 1H), 7.26 (t, J=7.80 Hz), 6.85 (m, 2H), 6.80 (s, 1H). 4.91 (s, 1H), 3.77 (s, 3H).

EXAMPLE 79

2-Amino-3-cyano-4-(3-bromo-4,5-dimethoxy-phenyl)-4H-pyrazino[2,3-h]chromene

The title compound was prepared from 2,7,8-triamino-3-cyano-4-(3-bromo-4,5-dimethoxyphenyl)-4H-chromene and glyoxal. $^1$H NMR (CD$_3$OD): 8.93 (m, 2H), 7.83 (d, J=9.0 Hz, 1H), 7.39 (d, J=9.0 Hz, 1H), 6.97 (s, 1H), 6.77 (s, 1H), 4.88 (s, 1H), 3.84 (d, 6H).

EXAMPLE 80

2-Amino-3-cyano-4-(3-bromo-4,5-dimethoxy-phenyl)-8-oxo-4,7,8,9-tetrahydroimidazo[4,5-h]chromene To a mixture of 2,7,8-triamino-3-cyano-4-(3-bromo-4,5-dimethoxy-phenyl)-4H-chromene (112 mg, 0.3 mmol) and K$_2$CO$_3$ (207 mg, 1.5 mmol) in CH$_2$Cl$_2$ (6 mL) was added phosgene (10 mL, 20% in toluene) at 0° C. under argon, and the mixture was stirred overnight. The mixture was stirred at 110° C. under argon for 1 h. The solvent was evaporated under high vacuum. The residue was purified by chromatography on silica gel with hexane: EtOAc (2:1) as eluant, yielding 42.5 mg (32%) of the title compound. $^1$H NMR (acetone-d$_6$): 7.03 (d, J=2.2 Hz, 1H), 7.01 (d, J=2.2 Hz, 1H), 6.80 (d, J=7.5 Hz, 1H), 6.70 (d, J=7.5 Hz, 1H), 6.04 (s, 1H), 4.79 (s, 1H), 3.86 (s, 3H), 3.76 (s, 3H).

EXAMPLE 81

2-Amino-3-cyano-4-(3-methoxyphenyl)-4H-indolo[4,5-b]pyran

The title compound was prepared from 4-hydroxyindole and 3-methoxybezaldehyde by a procedure similar to that described in Example 2A in 25% yield. $^1$H NMR (CDCl$_3$): 8.26 (brs, 1H), 7.26–7.18 (m, 2H), 7.09–7.06 (m, 1H), 6.84–6.74 (m, 4H), 6.65–6.63 (m, 1H), 4.80 (s, 1H), 4.65 (brs, 2H), 3.76 (s, 3H).

EXAMPLE 82

Identification of 2-Amino-3-cyano-4-(3-bromo-4,5-dimethoxyphenyl)-4H-indolo[7,6-b]pyran and Analogs as Caspase Cascade Activators and Inducers of Apoptosis in Solid Tumor Cells Human breast cancer cell lines T-47D and ZR-75-1 were grown according to media component mixtures designated by American Type Culture Collection+10% FCS (Invitrogen Corporation), in a 5% CO$_2$-95% humidity incubator at 37° C. T-47D and ZR-75-1 cells were maintained at a cell density between 30 and 80% confluency at a cell density of 0.1 to 0.6×10$^6$ cells/ml. Cells were harvested at 600×g and resuspended at 0.65×10$^6$ cells/mL into appropriate media+ 10% FCS. An aliquot of 45 μl of cells was added to a well of a 96-well microtiter plate containing 5 μl of a 10% DMSO in RPMI-1640 media solution containing 0.16 to 10 μM of 2-amino-3-cyano-4-(3-bromo-4,5-dimethoxyphenyl)-4H-indolo[7,6-b]pyran (Example 42) or other test compound (0.016 to 1 μM final). An aliquot of 45 μl of cells was added to a well of a 96-well microtiter plate containing 5 μl of a 10% DMSO in RPMI-1640 media solution without test compound as the control sample. The samples were mixed by agitation and then incubated at 37° C. for 24 h in a 5% CO$_2$-95% humidity incubator. After incubation, the samples were removed from the incubator and 50 μl of a solution containing 20 μM of N-(Ac-DEVD)-N'-ethoxycarbonyl-R110 (SEQ ID NO: 1) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 μg/ml lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3\ h)} - Control\ RFU_{(T=0)} = Net\ RFU_{(T=3\ h)}$$

The activity of caspase cascade activation was determined by the ratio of the net RFU value for 2-amino-3-cyano-4-(3-bromo-4,5-dimethoxyphenyl)-4H-indolo[7,6-b]pyran or other test compound to that of control samples. The EC$_{50}$ (nM) was determined by a sigmoidal dose-response calculation (Prism 2.0, GraphPad Software Inc.). The caspase activity (Ratio) and potency (EC$_{50}$) are summarized in Table I:

TABLE I

Caspase Activity and Potency

| Example | T-47D Ratio | T-47D EC$_{50}$ (nM) | ZR-75-1 Ratio | ZR-75-1 EC$_{50}$ (nM) |
|---|---|---|---|---|
| 1 | 5.1 | 153 | 10.8 | 94 |
| 2A | 4.0 | 72 | 4.1 | 14 |
| 2B | 1.2 | >10,000 | 1.9 | >10,000 |
| 2C | 1.1 | >10,000 | 0.9 | >10,000 |
| 2D | 4.4 | 78 | 4.4 | 50 |
| 2E | 4.1 | 39 | 4.4 | 29 |
| 2F | 4.7 | 44 | 4.4 | 26 |
| 2G | 5.6 | 56 | 4.5 | 25 |
| 2H | 5.5 | 29 | 3.9 | 16 |
| 2I | 6.2 | 50.4 | | |
| 2J | 5.0 | 34 | 7.4 | 21 |
| 2K | 5.6 | 37 | 6.9 | 16 |
| 2L | 4.5 | 63 | 7.4 | 41 |
| 2M | 5.8 | 1,387 | 6.9 | 786 |
| 2N | 4.2 | 57 | 6.8 | 47 |
| 2O | 6.4 | 323 | 7.1 | 193 |
| 3 | 8.4 | 29 | 4.5 | 16 |
| 4 | 8.1 | 37 | 5.6 | 33 |
| 5 | 6.9 | 37 | 7.1 | 46 |
| 6 | 6.8 | 54 | 12.8 | 30 |
| 7 | 5.4 | 108 | 10.7 | 53 |
| 8 | 8.5 | 126 | 10.1 | 62 |
| 9 | 7.6 | 116 | 12.8 | 50 |
| 10 | 6.1 | 48 | 9.0 | 36 |
| 11 | 4.5 | 45 | 6.6 | 28 |
| 12 | 6.1 | 14 | 6.7 | 9 |
| 13 | 4.4 | 25 | 7.0 | 14 |
| 14 | 7 | 10 | 7.7 | 10 |
| 15 | 5.9 | 7 | 6.3 | 4 |
| 16 | 7 | 11 | 6.7 | 6 |
| 17 | 5.9 | 254 | 8.2 | 147 |
| 18 | 9.0 | 56 | 8.8 | 38 |
| 19 | 5.9 | 274 | 9.2 | 206 |
| 20 | 4.0 | 120 | 5.2 | 58 |
| 21 | 6.0 | 697 | 9.2 | 562 |
| 22 | 5.8 | 4803 | 8.0 | 2482 |
| 23 | 4.6 | 146 | 5.2 | 102 |
| 24 | <2 | >10,000 | <2 | >10,000 |

TABLE I-continued

Caspase Activity and Potency

| Example | T-47D Ratio | T-47D EC$_{50}$ (nM) | ZR-75-1 Ratio | ZR-75-1 EC$_{50}$ (nM) |
|---|---|---|---|---|
| 25 | 6.1 | 463 | 9.7 | 325 |
| 26 | 3.5 | 140 | 6.4 | 82 |
| 27 | <2 | >10,000 | <2 | >10,000 |
| 28 | 3.4 | 158 | 5.2 | 154 |
| 29 | <2 | >10,000 | <2 | >10,000 |
| 30 | 7.5 | 24 | 13.2 | 14 |
| 31 | 7.9 | 27 | 11.0 | 12 |
| 32 | 7.2 | 17 | 9.5 | 4 |
| 33 | 7.0 | 7 | 10.4 | 7 |
| 34 | 4.7 | 107 | 5.6 | 43 |
| 35 | 6.9 | 3 | 5.5 | 8 |
| 36 | 5.9 | 10 | 2.9 | :3 |
| 37 | 6.4 | 57 | 3.4 | 31 |
| 39 | 8.4 | 283 | 14 | 177 |
| 40 | 7.9 | 27.4 | 8.9 | 16.9 |
| 41 | 6.8 | 13.9 | 7.2 | 6.6 |
| 42 | 7.6 | 30 | 13.1 | 25 |
| 43 | 6.5 | 143.1 | 5.9 | 81.9 |
| 44 | 7.0 | 256.1 | 9.6 | 137.6 |
| 45 | 6.0 | 41.8 | 11.9 | 35.4 |
| 46 | 6.4 | 61.8 | 7.1 | 26.3 |
| 47 | 1.9 | >1,000 | 7.3 | 552.0 |
| 48 | 10.5 | 36.8 | 6.1 | 23.8 |
| 49 | 10.1 | 67.7 | 5.8 | 35.9 |
| 50 | 10.1 | 16.5 | 10.6 | 14.8 |
| 51 | 11.5 | 36.8 | 6.7 | 18.6 |
| 52 | 11.8 | 26.0 | 9.9 | 22.7 |
| 53 | 10.1 | 79.7 | 7.0 | 26.4 |
| 54 | 7.3 | 314.3 | 7.5 | 216.5 |
| 55 | 7.4 | 15.3 | 7.2 | 4.0 |
| 56 | 8.3 | 252.1 | 7.7 | 157.1 |
| 57 | 7.2 | 58.0 | 7.3 | 27.9 |
| 58 | 4.1 | 2898.2 | 7.0 | 1631.0 |
| 59 | 1.1 | >10,000 | 1.2 | >10,000 |
| 60 | 6.7 | 388.3 | 5.5 | 57.0 |
| 61 | 4.1 | 2,898 | 7.0 | 1,631 |
| 62 | 6.6 | 144.3 | 6.0 | 75.3 |
| 63 | 9.1 | 147.0 | 10.1 | 114.2 |
| 64 | 8.0 | 28.8 | 4.8 | 13.2 |
| 65 | 1.5 | >1000 | 6.0 | 570.1 |
| 66A | 3.7 | 110.1 | 6.0 | 79.4 |
| 66B | 5.7 | 2906.1 | 6.8 | 1471.1 |
| 66C | 10.4 | 165.9 | 7.4 | 86.8 |
| 67 | 9.2 | 348.8 | 6.9 | 148.1 |
| 68A | 6.8 | 1980.5 | 6.5 | 1472.6 |
| 68B | 1.0 | >10,000 | 1.8 | >10,000 |
| 69 | 3.5 | 582.5 | 5.6 | 283.7 |
| 70 | 9.1 | 90.7 | 6.6 | 45.3 |
| 71 | 3.1 | 7851.0 | 4.1 | 3717.0 |
| 72 | 1.2 | >1000 | 3.6 | 567.3 |
| 73 | 7.5 | 29.4 | 9.0 | 26.7 |
| 74 | 7.4 | 149.2 | 8.9 | 99.3 |
| 75 | 6.3 | 345.3 | 3.4 | 146.2 |
| 76 | 2.0 | >10,000 | 2.3 | 4101.0 |
| 77 | 4.2 | 27.7 | 3.1 | 23.9 |
| 78 | 1.8 | >1000 | 3.6 | 537.0 |
| 79 | 8.3 | 209.2 | 10.2 | 102.7 |
| 80 | 8.8 | 50.5 | 7.5 | 21.5 |
| 81 | 6.4 | 62 | 7.1 | 26 |

Thus, 2-Amino-3-cyano-4-(3-bromo-4,5-dimethoxyphenyl)-4H-indolo-[7,6-b]pyran (Example 42) and analogs are identified as potent caspase cascade activators and inducers of apoptosis in solid tumor cells.

Some additional compounds within the scope of this invention are shown in Table II:

TABLE II

Caspase Activity and Potency

| Compound | T-47D Ratio | T-47D EC$_{50}$ (nM) | ZR-75-1 Ratio | ZR-75-1 EC$_{50}$ (nM) |
|---|---|---|---|---|
| 2,7-Diamino-3-cyano-4-phenyl-4H-chromene | 6.3 | 5628 | 8.6 | 2883 |
| 2,7-Diamino-3-cyano-4-(3-iodo-phenyl)-4H-chromene | 4.8 | 33 | 5.1 | 18 |
| 2,7-Diamino-3-cyano-4-(3,4,5-trimethoxyphenyl)-4H-chromene | 4.2 | 30 | 3.5 | 15 |
| 2-Amino-3-cyano-7-hydroxy-4-(3,4,5-trimethoxyphenyl)-4H-chromene | 7.3 | 456 | 10.3 | 208 |
| 2-Amino-3-cyano-7-(2-methyl-butanoylamino)-4-(3-bromo-4,5-dimethoxyphenyl)-4H-chromene | Inactive | Inactive | Inactive | Inactive |

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound selected from the group consisting of 3-cyano-2,7,8-triamino-4-(3-bromo-4,5-dimethoxyphenyl)-4H-chromene, 3-cyano-2,7,8-triamino-4-(3-methoxyphenyl)-4H-chromene and a pharmaceutically acceptable salt thereof.

2. A compound of claim 1 selected from the group consisting of 3-cyano-2,7,8-triamino-4-(3-bromo-4,5-dimethoxyphenyl)-4H-chromene and a pharmaceutically acceptable salt thereof.

3. A compound of claim 1 selected from the group consisting of 3-cyano-2,7,8-triamino-4-(3-methoxyphenyl)-4H-chromene and a pharmaceutically acceptable salt thereof.

4. A pharmaceutical composition comprising a pharmaceutically acceptable excipient or carrier and a compound of claims 2 or 3.

5. The pharmaceutical composition of claim 4, wherein said excipient or carrier is selected from the group consisting of saccharides, starch pastes, gelatin, tragacanth, cellulose preparations, calcium phosphates and polyvinyl pyrrolidone.

6. The pharmaceutical composition of claim 5, wherein said excipient or carrier is a saccharide selected from the group consisting of lactose, sucrose, manitol and sorbitol.

7. The pharmaceutical composition of claim 4, wherein said excipient or carrier is a lipophilic solvent.

8. The pharmaceutical composition of claim 7, wherein said lipophilic solvent is selected from the group consisting of fatty oils, fatty acid esters, polyethylene glycols and paraffin hydrocarbons.

9. The pharmaceutical composition of claim 7, wherein said lipophilic solvent is selected from the group consisting of sesame oil, ethyl oleate, triglycerides, polyethylene glycol-400, cremophor and cyclodextrins.

10. The pharmaceutical composition of claim 4, wherein said excipient or carrier is selected from the group consisting of vegetable oils, mineral oils, white petrolatum, branched chain fats, branched chain oils, animal fats and high molecular weight alcohol (greater than $C_{12}$).

11. The pharmaceutical composition of claim 4, wherein said excipient or carrier is a saline solution.

* * * * *

SEQUENCE LISTING

<160> NUMBER OF SEQ ID NOS: 1

<210> SEQ ID NO 1
<211> LENGTH: 4

```
-continued
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal acetyl
<220> FEATURE:
<221> NAME/KEY: MOD_RES
<222> LOCATION: (4)..(4)
<223> OTHER INFORMATION: C-terminal N'-ethoxycarbonyl-Rhodamine 110

<400> SEQUENCE: 1

Asp Glu Val Asp
1
```